(12) United States Patent
Castro et al.

(10) Patent No.: US 11,591,339 B2
(45) Date of Patent: Feb. 28, 2023

(54) SOLID FORMS OF (R)-N-(2-(5-FLUOROPYRIDIN-3-YL)-8-ISOPROPYLPYRAZOLO[1,5-A][1,3,5]TRIAZIN-4-YL)-2,3,4,9-TETRAHYDRO-1H-CARBAZOL-3-AMINE MALEATE AS ARYL HYDROCARBON RECEPTOR (AHR) INHIBITORS

(71) Applicant: Ikena Oncology, Inc., Boston, MA (US)

(72) Inventors: Alfredo C. Castro, Somerville, MA (US); James Martin Nolan, III, Boston, MA (US); Sarah Jean Bethune, Durham, NC (US); Corinne Marie Folberth, Durham, NC (US)

(73) Assignee: IKENA ONCOLOGY, INC., Boston, MA (US)

( * ) Notice: Subject to any disclaimer, the term of this patent is extended or adjusted under 35 U.S.C. 154(b) by 112 days.

(21) Appl. No.: 17/104,237

(22) Filed: Nov. 25, 2020

(65) Prior Publication Data

US 2021/0253579 A1    Aug. 19, 2021

Related U.S. Application Data

(60) Provisional application No. 62/940,481, filed on Nov. 26, 2019.

(51) Int. Cl.
*A61K 31/53* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .............................. A61K 31/53; C07D 487/04
USPC .......................................... 514/246; 544/184
See application file for complete search history.

(56) References Cited

U.S. PATENT DOCUMENTS

| | | | |
|---|---|---|---|
| 8,906,682 B2 | 12/2014 | June et al. |
| 10,570,138 B2 | 2/2020 | Castro et al. |
| 10,689,388 B1 | 6/2020 | Castro et al. |
| 11,358,969 B2 | 6/2022 | Castro et al. |
| 2004/0009978 A1 | 1/2004 | Hayakawa et al. |
| 2004/0235877 A1 | 11/2004 | Ishizuka et al. |
| 2006/0128729 A1 | 6/2006 | Pal et al. |
| 2010/0183564 A1 | 7/2010 | Boitano et al. |
| 2011/0281863 A1 | 11/2011 | Bearss et al. |
| 2013/0274216 A1 | 10/2013 | Carlson et al. |
| 2018/0072741 A1 | 3/2018 | Vechorkin et al. |
| 2018/0298013 A1 | 10/2018 | Romero et al. |
| 2018/0327411 A1 | 11/2018 | Castro et al. |
| 2020/0331917 A1 | 10/2020 | Castro et al. |
| 2021/0253579 A1 | 8/2021 | Castro et al. |
| 2022/0144839 A1 | 5/2022 | Castro et al. |

FOREIGN PATENT DOCUMENTS

| | | |
|---|---|---|
| EP | 2697215 A1 | 2/2014 |
| WO | WO-1996040706 A1 | 12/1996 |
| WO | WO-2002049651 A1 | 6/2002 |
| WO | WO-2004022559 A1 | 3/2004 |
| WO | WO-2004026867 A2 | 4/2004 |
| WO | WO-2004092196 A2 | 10/2004 |
| WO | WO-2006029879 A2 | 3/2006 |
| WO | WO-2006105021 A2 | 10/2006 |
| WO | WO-2006122150 A1 | 11/2006 |
| WO | WO-2007005874 A2 | 1/2007 |
| WO | WO-2007075598 A2 | 7/2007 |
| WO | WO-2008036642 A2 | 3/2008 |
| WO | WO-2008036653 A2 | 3/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009077334 A1 | 6/2009 |
| WO | WO-2010019570 A2 | 2/2010 |
| WO | WO-2010077634 A1 | 7/2010 |
| WO | WO-2011028683 A1 | 3/2011 |
| WO | WO-2011056652 A1 | 5/2011 |
| WO | WO-2011070024 A1 | 6/2011 |
| WO | WO-2011107553 A1 | 9/2011 |
| WO | WO-2011109400 A2 | 9/2011 |
| WO | WO-2011131407 A1 | 10/2011 |

(Continued)

OTHER PUBLICATIONS

PCT International Search Report from PCT Application No. PCT/US2020/062197 mailed by the ISA/EP dated Jan. 26, 2021; 12 Pages.
CAS STN Abstract, RN 1779709-85-1 (Pub. Jun. 14, 2015).
"CID 22906251 Compound Summary: 2-phenyl-7H-pyrrolo[2,3-d]pyrimidine," PubChem. Created Dec. 5, 2007: https://pubchem.ncbi.nlm.nih.gov/compound/22906251.

(Continued)

*Primary Examiner* — Douglas M Willis
(74) *Attorney, Agent, or Firm* — Dechert LLP; Andrea L. C. Reid; Gang Wang

(57) ABSTRACT

The present invention provides solid forms of (R)—N-(2-(5-fluoropyridin-3-yl)-8-isopropylpyrazolo[1,5-a][1,3,5]triazin-4-yl)-2,3,4,9-tetrahydro-1H-carbazol-3-amine maleate (Compound 2) represented by the formula:

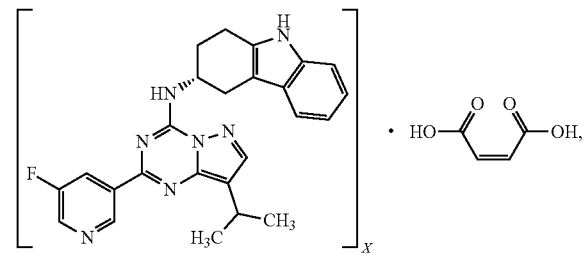

19 Claims, 25 Drawing Sheets

(56) References Cited

FOREIGN PATENT DOCUMENTS

| WO | WO-2011140249 A2 | 11/2011 |
| WO | WO-2012032433 A1 | 3/2012 |
| WO | WO-2012044562 A2 | 4/2012 |
| WO | WO-2012142237 A1 | 10/2012 |
| WO | WO-2012143144 A1 | 10/2012 |
| WO | WO-2012145493 A1 | 10/2012 |
| WO | WO-2013079174 A1 | 6/2013 |
| WO | WO-2013086436 A1 | 6/2013 |
| WO | WO-2013087699 A1 | 6/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014036357 A1 | 3/2014 |
| WO | WO-2014060112 A1 | 4/2014 |
| WO | WO-2014138485 A1 | 9/2014 |
| WO | WO-2017004405 A1 | 1/2017 |
| WO | WO-2018195397 A2 | 10/2018 |
| WO | WO-2020081636 A1 | 4/2020 |
| WO | WO-2021108469 A1 | 6/2021 |
| WO | WO-2021108528 A1 | 6/2021 |
| WO | WO-2021142180 A1 | 7/2021 |
| WO | WO-2022094567 A1 | 5/2022 |

OTHER PUBLICATIONS

"CID 53894831 Compound Summary: 5-phenyl-1H-pyrazolo[4,3-d]pyrimidine," PubChem. Created Dec. 4, 2011: https://pubchem.ncbi.nlm.nih.gov/compound/53894831.

"CID 54404831 Compound Summary," PubChem. Created Dec. 4, 2011: https://pubchem.ncbi.nlm.nih.gov/compound/54404831.

"CID 56889663 Compound Summary: N-[2-(1-methyl-1H-benzimidazol-2-yl)ethyl]-5-(4-pyridinyl)pyrazolo[1,5-a]pyrimidin-7-amine," PubChem. Created Mar. 30, 2012: https://pubchem.ncbi.nlm.nih.gov/compound/56889663.

"CID 56913247 Compound Summary: N-(2-imidazo[1,2-a]pyridin-2-ylethyl)-5-(4-pyridinyl)pyrazolo[1,5-a]pyrimidin-7-amine," PubChem. Created Mar. 30, 2012: https://pubchem.ncbi.nlm.nih.gov/compound/56913247.

"CID 71138224 Compound Summary: N,N-dimethyl-3-(5-thiophen-3-yl-1H-pyrazolo[4,3-d]pyrimidin-7-yl)aniline," PubChem. Created Mar. 21, 2013: https://pubchem.ncbi.nlm.nih.gov/compound/71138224.

Adams et al., "Big opportunities for small molecules in immuno-oncology," Nat Rev Drug Discov. 2015;14(9):603-22.

Berge et al., "Pharmaceutical Salts," Journal of Pharmaceutical Sciences. 1977;66(1):1-19.

Esser et al., "The aryl hydrocarbon receptor in immunity," Trends Immunol. 2009;30(9):447-54.

Funatake et al., "Cutting edge: activation of the aryl hydrocarbon receptor by 2,3,7,8-tetrachlorodibenzo-p-dioxin generates a population of CD4+ CD25+ cells with characteristics of regulatory T cells," J Immunol. 2005;175(7):4184-8.

Gandhi et al., "Activation of the aryl hydrocarbon receptor induces human type 1 regulatory T cell-like and Foxp3(+) regulatory T cells," Nat Immunol. 2010;11 (9):846-53.

Guastella et al., "Investigation of the aryl hydrocarbon receptor and the intrinsic tumoral component of the kynurenine pathway of tryptophan metabolism in primary brain tumors," J Neurooncol. 2018;139(2):239-249.

Head et al., "The aryl hydrocarbon receptor is a modulator of anti-viral immunity," Biochem Pharmacol. 2009;77(4):642-53.

Ide et al., "Aryl hydrocarbon receptor signaling involved in the invasiveness of LNCaP cells," Hum Cell. Apr. 2017;30(2):133-139.

Ishida et al., "Activation of Aryl Hydrocarbon Receptor Promotes Invasion of Clear Cell Renal Cell Carcinoma and is Associated With Poor Prognosis and Cigarette Smoke," Intt J Cancer. 2015;137(2):299-310.

Ishida et al., "Activation of the aryl hydrocarbon receptor pathway enhances cancer cell invasion by upregulating the MMP expression and is associated with poor prognosis in upper urinary tract urothelial cancer," Carcinogenesis. Feb. 2010;31(2):287-95.

Ishida et al., "Prognostic significance of nuclear expression of Aryl hydrocarbon receptor in urothelial carcinoma of the upper urinary tract," Eur Urol(suppl). 2009;8(4):288(abstract 670).

Jin et al., "Aryl hydrocarbon receptor activation reduces dendritic cell function during influenza virus infection," Toxicol Sci. 2010;116(2):514-22.

Jin et al., "New insights into the role of the aryl hydrocarbon receptor in the function of CD11c+ cells during respiratory viral infection," Eur J Immunol. 2014;44(6):1685-1698.

Mezrich et al., "An interaction between kynurenine and the aryl hydrocarbon receptor can generate regulatory T cells," J Immunol. 2010;185(6):3190-8.

Moon et al., "Targeting the indoleamine 2,3-dioxygenase pathway in cancer," J Immunother Cancer. 2015;3:51.

Murray et al., "Aryl hydrocarbon receptor ligands in cancer: friend and foe," Nat Rev Cancer. 2014;14(12):801-14.

Nguyen et al., "Aryl hydrocarbon receptor and kynurenine: recent advances in autoimmune disease research," Front Immunol. 2014;5:551.

Nguyen et al., "The Roles of Aryl Hydrocarbon Receptor in Immune Responses," Int Immunol. 2013;25(6):335-43.

Okazaki et al., "A rheostat for immune responses: the unique properties of PD-1 and their advantages for clinical application," 2013;14(12):121-8.

Opitz et al., "An endogenous tumour-promoting ligand of the human aryl hydrocarbon receptor," Nature. 2011;478(7368):197-203.

Patel et al., "Revealing facts behind spray dried solid dispersion technology used for solubility enhancement," Saudi Pharm J. 2015;23(4):352-65.

PCT International Search Report and Written Opinion from PCT/US2018/028532, dated Oct. 9, 2018.

PCT International Search Report and Written Opinion from PCT/US2019/056455, dated Jan. 23, 2020.

PCT International Search Report and Written Opinion from PCT/US2020/062116, dated Mar. 19, 2021.

PCT International Search Report and Written Opinion from PCT/US2021/012571, dated Apr. 23, 2021.

PCT International Search Report and Written Opinion from PCT/US2021/072065, dated Feb. 17, 2022.

Peng et al., "Aryl hydrocarbon receptor pathway activation enhances gastric cancer cell invasiveness likely through a c-Jun-dependent induction of matrix metalloproteinase-9," BMC Cell Biol. 2009;10:27.

Popowycz et al., "Pyrazolo[1,5-a]-1,3,5-triazine as a Purine Bioisostere: Access to Potent Cyclin-Dependent Kinase Inhibitor (R)-Roscovitine Analogue," J Med Chem. 2009;52(3)655-663.

Ross et al., "Bispecific T cell engager (BITE®) antibody constructs can mediate bystander tumor cell killing," PLoS ONE. 2017; 12(8): e0183390.

Su et al., "Prognostic value of nuclear translocation of aryl hydrocarbon receptor for non-small cell lung cancer," Anticancer Res. 2013;33(9):3953-61.

Talari et al., "Overexpression of aryl hydrocarbon receptor (AHR) signalling pathway in human meningioma," J Neurooncol. Apr. 2018;137(2):241-248.

Toogood, "Small molecule immuno-oncology therapeutic agents," Bioorg. Med. Chem. Lett. 2018;28(3):319-329.

Uyttenhove et al., "Evidence for a tumoral immune resistance mechanism based on tryptophan degradation by indoleamine 2,3-dioxygenase," Nat. Med. 2003;9(10):1269-74.

Vacher et al., "High AHR expression in breast tumors correlates with expression of genes from several signaling pathways namely inflammation and endogenous tryptophan metabolism," PLoS One. Jan. 10, 2018;13(1):e0190619.

Vogel et al., "Cross-talk between aryl hydrocarbon receptor and the inflammatory response: a role for nuclear factor-kB," J Biol Chem. 2014;289(3): 1866-75.

Wagage et al., "The aryl hydrocarbon receptor promotes IL-10 production by NK cells," J Immunol. 1977; 192(4):1661-70.

Zou et al., "PD-L1 (B7-H1) and PD-1 pathway blockade for cancer therapy: Mechanisms, response biomarkers, and combinations," Sci. Transl. Med. 2016;8(328):328rv4.

SOLID FORMS OF (R)-N-(2-(5-FLUOROPYRIDIN-3-YL)-8-ISOPROPYLPYRAZOLO[1,5-A][1,3,5]TRIAZIN-4-YL)-2,3,4,9-TETRAHYDRO-1H-CARBAZOL-3-AMINE MALEATE AS ARYL HYDROCARBON RECEPTOR (AHR) INHIBITORS

CROSS-REFERENCE TO RELATED APPLICATIONS

This application claims the benefit under 35 U.S.C. § 119(e) of U.S. Provisional patent Application No. 62/940,481, filed Nov. 26, 2019, the contents of which are herein incorporated by reference in their entireties.

FIELD OF THE INVENTION

This application relates to various forms and compositions, and methods, useful for treating various conditions in which the aryl hydrocarbon receptor (AHR) is implicated, by the administration of small molecule therapeutics which act as inhibitors of ABR.

BACKGROUND OF THE INVENTION

The aryl hydrocarbon receptor (AHR) is a transcription factor that without ligand exists in the inactive state in the cytoplasm bound to HSP90. Upon ligand binding, AHR translocates to the nucleus where it dimerizes with ARNT forming a functional transcription factor. AHR/ARNT binds dioxin response elements (DRE) in the promotor of many genes where it modulates gene transcription. The most well documented genes regulated by AHR are the cytochrome P450 genes Cyp1b1 and Cyp1a1, where activation of AHR greatly increases expression of these genes. Therefore, Cyp1b1 and Cyp1a1 mRNA levels are a selective readout of AHR activation (reviewed in Murray et al., 2014).

Many exogenous and endogenous agonists of AHR exist that activate the receptor. The best characterized exogenous ligand class are the dioxins. One of the first endogenous ligands to be characterized is kynurenine, generated by TDO (Opitz 2011) or IDO (Mezrich 2010). Kynurenine is a stable metabolite in the IDO/TDO pathway and is the product of tryptophan degradation. Kynurenine has been shown to activate AHR as measured by an increase in Cyp1a1 and/or Cyp1b1 mRNA levels in multiple cell types, along with other DRE-driven genes.

AHR activation has pro-tumor effects by acting directly on the tumor cells and indirectly by causing immunosuppression, therefore not allowing the body's own immune system to attack the tumor. For example, AHR activation through multiple ligands leads to increased expression of FoxP3 and results in a polarization of CD4+ T-cells toward a suppressive subset called Foxp3+ T-regulatory cells (Tregs). These T-reg cells inhibit the proliferation of activated T cells (Funatake 2005, other refs). Interestingly, kynurenine has been shown to induce immunosuppressive Tregs through AHR. Kynurenine does not affect T-reg generation in AHR-null T cells or when an AHR antagonist is added (Mezrich). In addition to T-regs, AHR activation also leads to expansion of suppressive Trl T cells (Gandhi 2010). It has also been shown that expression of IDO is regulated by AHR activation in both tumor cells and T cells, leading to increased immune suppression (Vogel). It is likely there is also a role for AHR in immune suppressive myeloid cells (Nguyen 2013). Immune suppression is often associated with high levels of anti-inflammatory cytokines and there is evidence that AHR is involved in activation of many of these cytokines, such as IL-10 (Gandhi 2010, Wagage 2014).

There remains an unmet need to develop inhibitors of AHR for treating diseases, disorders and conditions associated therewith.

SUMMARY OF THE INVENTION

It has now been found that compounds of the present invention, and compositions thereof, are useful for treating, preventing, and/or reducing a risk of a disease, disorder, or condition in which aldehyde toxicity is implicated in the pathogenesis. In general, salt forms or freebase forms, and pharmaceutically acceptable compositions thereof, are useful for treating or lessening the severity of a variety of diseases or disorders as described in detail herein. Such compounds are represented by the chemical structure below, denoted as compound A:

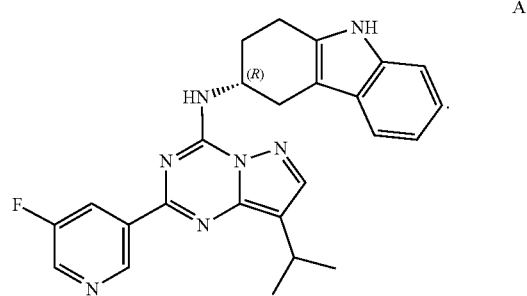

Compounds of the present invention, and pharmaceutically acceptable compositions thereof, are useful for treating a variety of diseases, disorders or conditions, associated with AHR. Such diseases, disorders, or conditions include those described herein.

Compounds provided by this invention are also useful for the study of AHR in biological and pathological phenomena; the study of intracellular signal transduction pathways; and the comparative evaluation of new AHR inhibitors in vitro or in vivo.

DETAILED DESCRIPTION OF THE INVENTION

Figure 1:
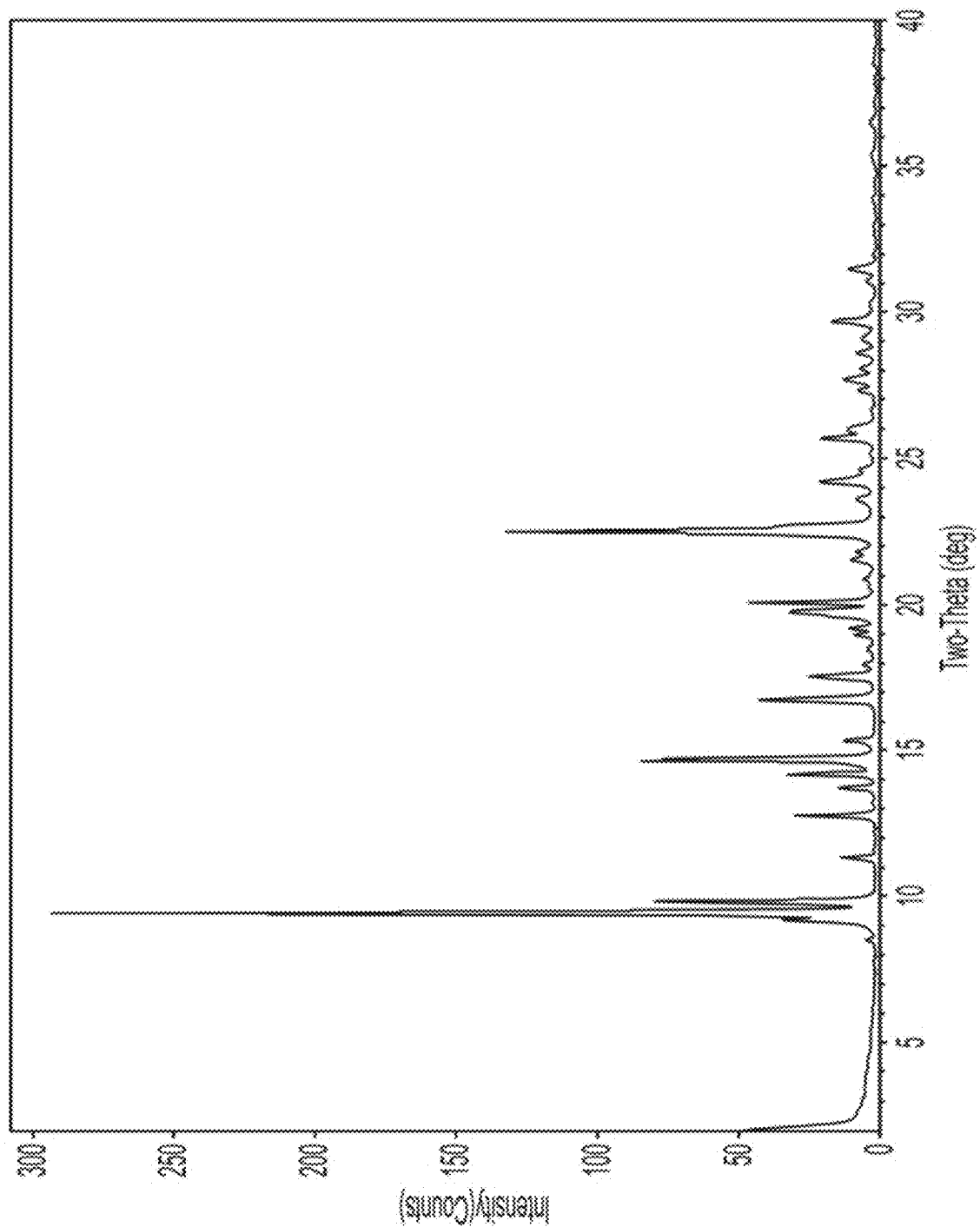
FIG. 1 depicts the XRPD pattern of Compound A, Form B.

General Description of Certain Aspects of the Invention

U.S. patent application Ser. No. 15/958,586, filed Apr. 20, 2018 and published as United States Published Patent Application No. 2018-0327411 on Nov. 15, 2018 ("the '411 publication," the entirety of which is hereby incorporated herein by reference), describes certain AHR inhibiting compounds. Such compounds include compound A:

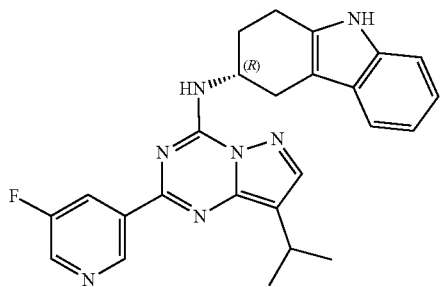

A

Compound A, (3R)—N-[2-(5-fluoro-3-pyridyl)-8-isopropyl-pyrazolo[1,5-a][1,3,5]triazin-4-yl]-2,3,4,9-tetrahydro-1H-carbazol-3-amine, is designated as compound 1-40 in the '411 publication and the synthesis of compound A is described in detail at Example 39 of the '411 publication, and is reproduced herein for ease of reference.

It would be desirable to provide a solid form of compound A (e.g., as a freebase thereof or salt thereof) that imparts characteristics such as improved aqueous solubility, stability and ease of formulation. Accordingly, the present invention provides both free base forms and salt forms of compound A:

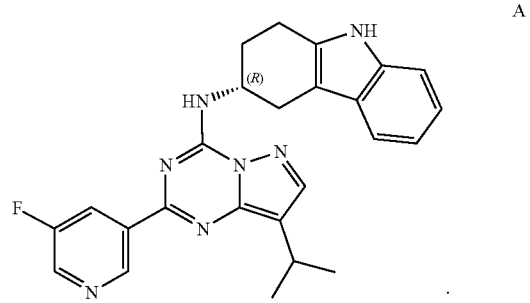

A

Free Base Forms of Compound A

It is contemplated that compound A can exist in a variety of physical forms. For example, compound A can be in solution, suspension, or in solid form. In certain embodiments, compound A is in solid form. When compound A is in solid form, said compound may be amorphous, crystalline, or a mixture thereof. Exemplary solid forms are described in more detail below.

In some embodiments, the present invention provides a form of compound A substantially free of impurities. As used herein, the term "substantially free of impurities" means that the compound contains no significant amount of extraneous matter. Such extraneous matter may include different forms of compound A, residual solvents, or any other impurities that may result from the preparation of, and/or isolation of, compound A. In certain embodiments, at least about 95% by weight of a form of compound A is present. In still other embodiments of the invention, at least about 99% by weight of a form of compound A is present.

According to one embodiment, a form of compound A is present in an amount of at least about 97, 97.5, 98.0, 98.5, 99, 99.5, 99.8 weight percent where the percentages are based on the total weight of the composition. According to another embodiment, a form of compound A contains no more than about 3.0 area percent HPLC of total organic impurities and, in certain embodiments, no more than about 1.5 area percent HPLC total organic impurities relative to the total area of the HPLC chromatogram. In other embodiments, a form of compound A contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound A is also meant to include all tautomeric forms of compound A. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound A can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound A is a crystalline solid. In other embodiments, compound A is a crystalline solid substantially free of amorphous compound A. As used herein, the term "substantially free of amorphous compound A" means that the compound contains no significant amount of amorphous compound A. In certain embodiments, at least about 95% by weight of crystalline compound A is present. In still other embodiments of the invention, at least about 99% by weight of crystalline compound A is present.

It has been found that compound A can exist in at least three distinct polymorphic forms. In certain embodiments, the present invention provides a polymorphic form of compound A referred to herein as Form A. In certain embodiments, the present invention provides a polymorphic form of compound A referred to herein as Form B. In certain embodiments, the present invention provides a mixture of Form A and Form B of compound A. In certain embodiments, the present invention provides a polymorphic form of compound A referred to herein as Form C.

In some embodiments, compound A is amorphous. In some embodiments, compound A is amorphous, and is substantially free of crystalline compound A.

Form B of Compound A

In some embodiments, Form B of compound A has at least 1, 2, 3, 4 or 5 spectral peak(s) selected from the peaks listed in Table B below.

TABLE B

XRPD Peak Positions for Form B of Compound A

| Position [°2θ][1] | d-spacing [Å] | Intensity [%] |
|---|---|---|
| 8.5 | 10.3405 | 0.8 |
| 9.2 | 9.5896 | 11 |
| 9.5 | 9.3466 | 100 |
| 9.8 | 8.9763 | 26.3 |
| 11.3 | 7.7944 | 4 |
| 12.8 | 6.907 | 9.6 |
| 13.7 | 6.4438 | 3.9 |
| 14.2 | 6.2284 | 10 |
| 14.7 | 6.0202 | 27.4 |
| 15.4 | 5.7663 | 3.5 |
| 16.8 | 5.2862 | 13.9 |
| 17.5 | 5.0495 | 7.6 |
| 17.9 | 4.9378 | 1 |
| 18.5 | 4.8002 | 0.7 |
| 19.0 | 4.6705 | 1.3 |
| 19.2 | 4.6159 | 2 |
| 19.8 | 4.485 | 9.8 |
| 20.1 | 4.4138 | 14.2 |
| 20.9 | 4.2497 | 1.1 |
| 21.6 | 4.1169 | 2.3 |
| 21.8 | 4.073 | 1.4 |
| 22.5 | 3.9481 | 44 |
| 23.6 | 3.7662 | 1.5 |
| 24.2 | 3.6729 | 5.8 |
| 24.6 | 3.6111 | 1.5 |
| 25.7 | 3.4637 | 6.2 |
| 26.0 | 3.4299 | 3.1 |
| 27.3 | 3.2589 | 1.8 |
| 27.7 | 3.2135 | 3.4 |
| 28.1 | 3.1726 | 1.4 |
| 28.6 | 3.1145 | 1.6 |
| 29.1 | 3.0612 | 1 |
| 29.7 | 3.0045 | 4.8 |
| 31.5 | 2.8379 | 3.4 |

[1]In this and all subsequent tables, the position 2θ is within ± 0.2.

In some embodiments, Form B of compound A is characterized in that it has one or more peaks in its X-ray powder diffraction pattern selected from those at about 9.5, about 9.8 and about 14.7 degrees 2-theta. In some embodiments, Form B of compound A is characterized in that it has two or more peaks in its X-ray powder diffraction pattern selected from those at about 9.5, about 9.8 and about 14.7 degrees 2-theta. In some embodiments, Form B of compound A is characterized in that it has all three peaks in its X-ray powder diffraction pattern selected from those at about 9.5, about 9.8 and about 14.7 degrees 2-theta.

In certain embodiments, the X-ray powder diffraction pattern of Form B of compound A is substantially similar to the XRPD provided in FIG. 1.

Methods for preparing Form B of compound A are described infra.

Form C of Compound A

In some embodiments, Form C of compound A has at least 1, 2, 3, 4 or 5 spectral peak(s) selected from the peaks listed in Table C below.

TABLE C

XRPD Peak Positions for Form C of Compound A

| Position [°2θ][1] | d-spacing [Å] | Intensity [%] |
|---|---|---|
| 6.02 | 14.6575 | 100 |
| 7.34 | 12.0353 | 37.5 |
| 8.45 | 10.4488 | 5.5 |
| 8.60 | 10.275 | 13.5 |
| 8.61 | 10.2605 | 39.2 |
| 9.03 | 9.7846 | 16.8 |
| 10.29 | 8.5906 | 81.2 |
| 13.27 | 6.668 | 12.9 |
| 14.28 | 6.1968 | 3 |
| 14.45 | 6.1252 | 21.4 |
| 14.86 | 5.9561 | 26 |
| 15.20 | 5.8241 | 4.8 |
| 15.53 | 5.6994 | 11.5 |
| 15.80 | 5.6027 | 3.6 |
| 16.54 | 5.3548 | 1.3 |
| 16.85 | 5.256 | 2.6 |
| 17.26 | 5.1331 | 28.9 |
| 17.69 | 5.0108 | 1.4 |
| 18.10 | 4.8972 | 8.1 |
| 18.29 | 4.8453 | 8.7 |
| 18.59 | 4.7689 | 1.4 |
| 19.09 | 4.6451 | 3.1 |
| 19.43 | 4.5653 | 6.3 |
| 19.61 | 4.5233 | 11.2 |
| 19.89 | 4.4608 | 5 |
| 20.25 | 4.3824 | 18.9 |
| 21.18 | 4.191 | 21.9 |
| 22.30 | 3.984 | 3.1 |
| 22.41 | 3.9644 | 6.2 |
| 22.90 | 3.881 | 2.5 |
| 23.53 | 3.7773 | 2.5 |
| 24.44 | 3.6389 | 1.2 |
| 24.82 | 3.5836 | 3.6 |
| 25.39 | 3.5055 | 1.3 |
| 25.66 | 3.4686 | 2.3 |
| 26.00 | 3.4238 | 9.4 |
| 26.14 | 3.4064 | 8.8 |
| 26.69 | 3.3367 | 4 |
| 27.04 | 3.2951 | 8.6 |
| 27.35 | 3.2585 | 7.9 |
| 28.02 | 3.1813 | 2 |
| 29.12 | 3.0638 | 2 |

[1]In this and all subsequent tables, the position 2θ is within ± 0.2.

In some embodiments, Form C of compound A is characterized in that it has one or more peaks in its X-ray powder diffraction pattern selected from those at about 6.02, about 8.61 and about 10.29 degrees 2-theta. In some embodiments, Form C of compound A is characterized in that it has two or more peaks in its X-ray powder diffraction pattern selected from those at about 6.02, about 8.61 and about 10.29 degrees 2-theta. In some embodiments, Form C of compound A is characterized in that it has all three peaks in its X-ray powder diffraction pattern selected from those at about 6.02, about 8.61 and about 10.29 degrees 2-theta.

Figure 3:
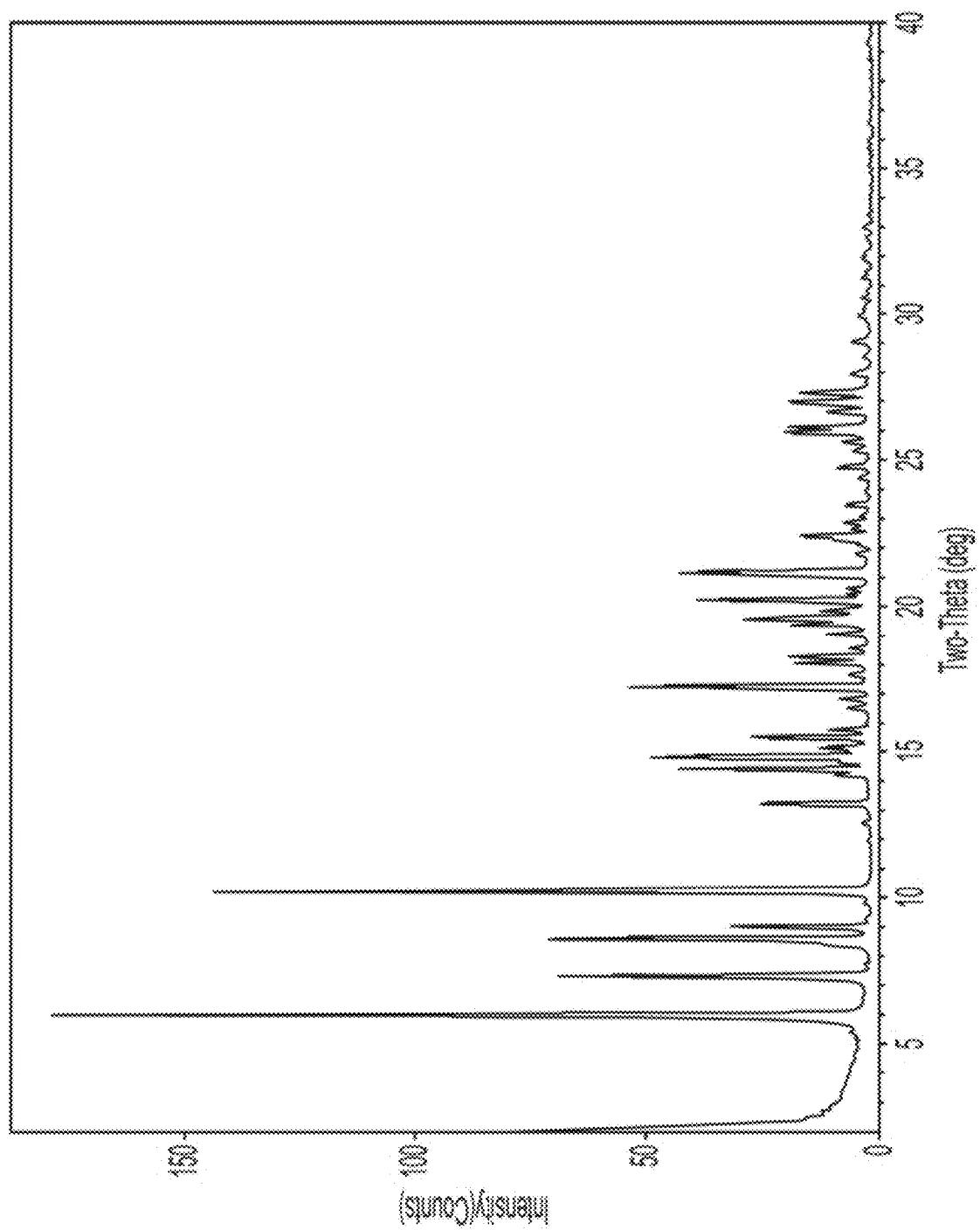
FIG. 3 depicts the XRPD pattern of Compound A, Form C.

In certain embodiments, the X-ray powder diffraction pattern of Form C of compound A is substantially similar to the XRPD provided in FIG. 3.

Methods for preparing Form C of compound A are described infra.

Mixture of Form A and Form B of Compound A

Figure 24:
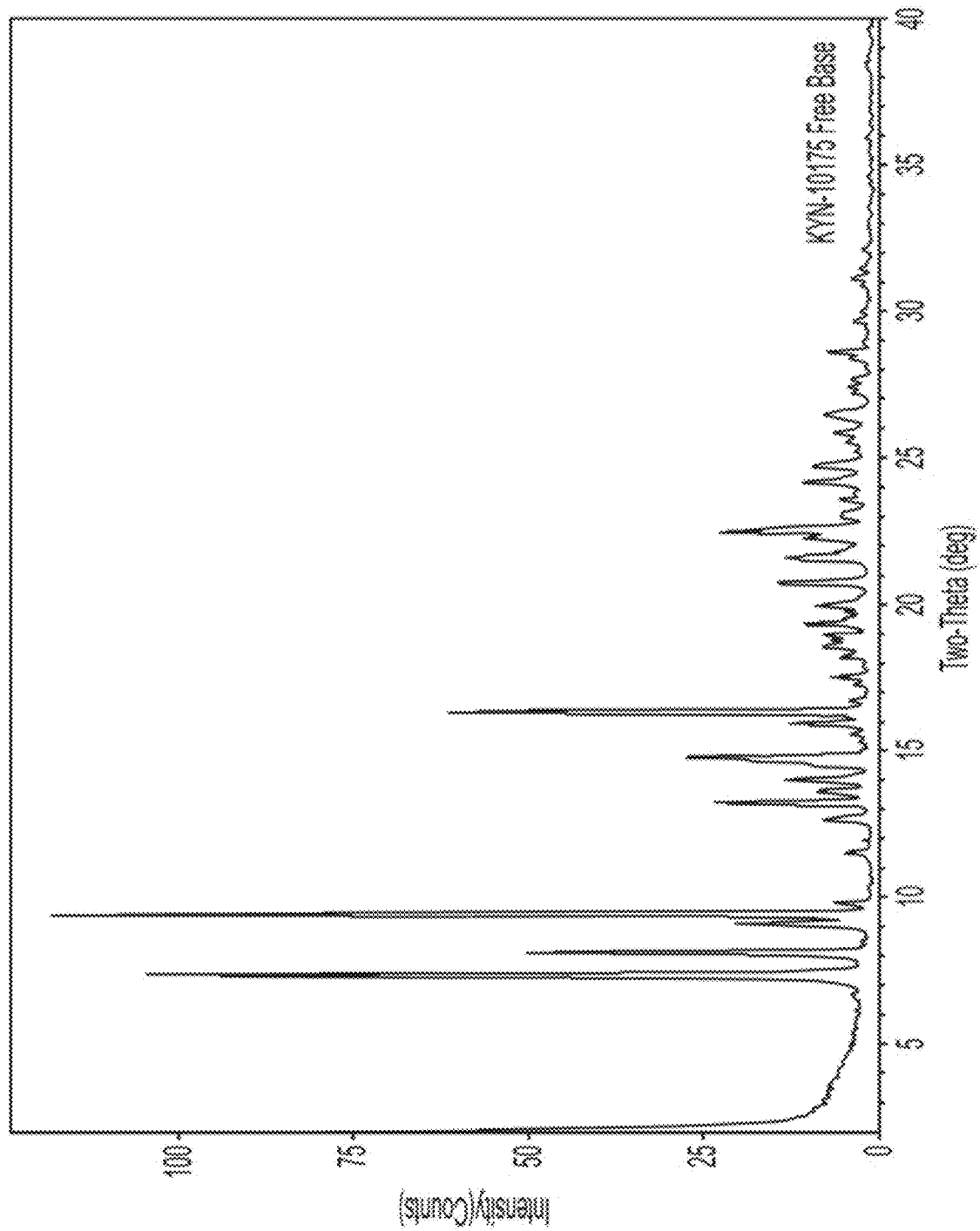
FIG. 24 depicts the XRPD pattern of a mixture of Form A and Form B Compound A.

In some embodiments, the present invention provides a mixture of Form A and Form B of compound A, which has a X-ray powder diffraction pattern substantially similar to the XRPD provided in FIG. 24.

Figure 25:
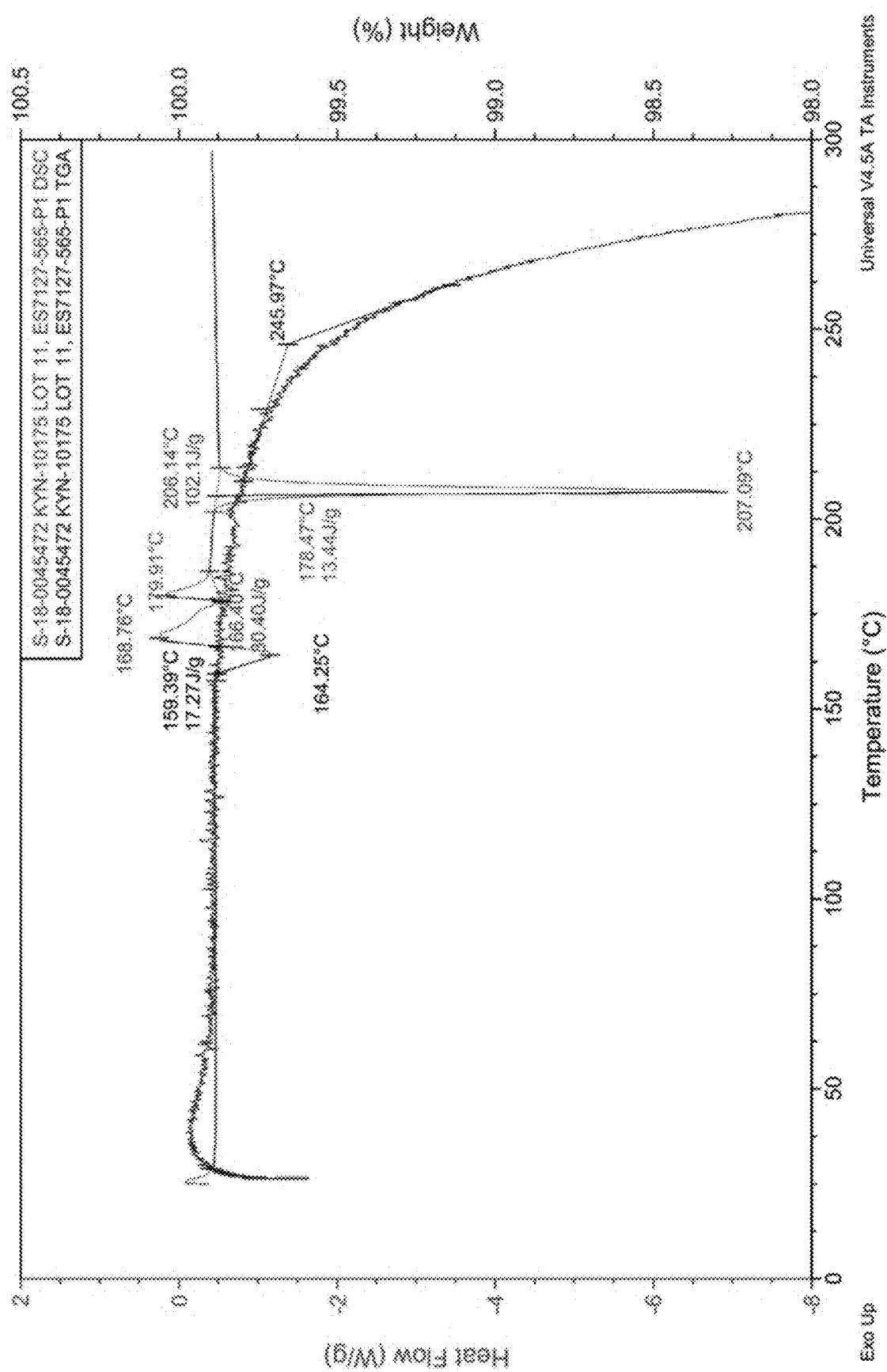
FIG. 25 depicts TGA/DSC of a mixture of Form A and Form B of Compound A.

In some embodiments, a mixture of Form A and Form B of compound A has a TGA substantially similar to the TGA provided in FIG. 25. In some embodiments, a mixture of Form A and Form B of compound A has a DSC substantially similar to the DSC provided in FIG. 25.

Methods for preparing a mixture of Form A and Form B of compound A are described infra.

In some embodiments, the present invention provides compound A:

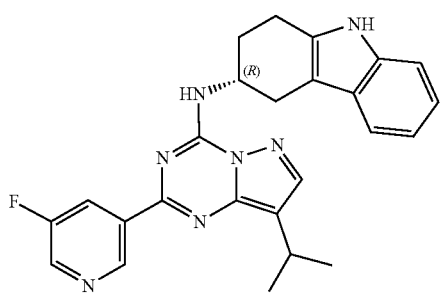

wherein said compound is crystalline.

In some embodiments, the present invention provides compound A, wherein said compound is substantially free of amorphous compound A.

In some embodiments, the present invention provides compound A, wherein said compound is substantially free of impurities.

In some embodiments, the present invention provides compound A, wherein said compound has an XRPD substantially similar to that depicted in FIG. 1.

In some embodiments, the present invention provides compound A, wherein said compound has an XRPD substantially similar to that depicted in FIG. 3.

In some embodiments, the present invention provides compound A, wherein said compound has an XRPD substantially similar to that depicted in FIG. 24.

In some embodiments, the present invention provides a composition comprising compound A and a pharmaceutically acceptable carrier or excipient.

In some embodiments, the present invention provides a method of inhibiting AHR comprising administering to said patient compound A or composition thereof. In some embodiments, the present invention provides a method of inhibiting AHR in a patient comprising administering to said patient compound A or composition thereof. In some embodiments, the present invention provides a method of treating one or more disorders associated with activity of AHR comprising administering to said patient compound A or composition thereof.

In some embodiments, the present invention provides a method for treating an AHR-mediated disorder comprising the step of administering to a patient in need thereof compound A or composition thereof. In some embodiments, the AHR-mediated disorder is a proliferative disease such as cancer or an inflammatory disorder.

Salt Forms of Compound A

In some embodiments, an acid and compound A are ionically bonded to form one of compounds 1 through 7, described below. It is contemplated that compounds 1 through 7 can exist in a variety of physical forms. For example, compounds 1 through 7 can be in solution, suspension, or in solid form. In certain embodiments, compounds 1 through 7 are in solid form. When compounds 1 through 7 are in solid form, said compounds may be amorphous, crystalline, or a mixture thereof. Exemplary such solid forms of compounds 1 through 7 are described in more detail below.

Compound 1 (Esylate Salts of Compound A)

According to one embodiment, the present invention provides an esylate salt of compound A, represented by compound 1:

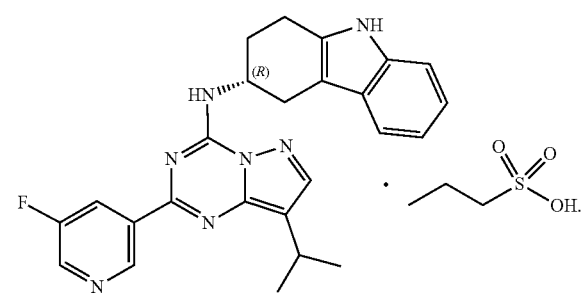

It will be appreciated by one of ordinary skill in the art that the ethanesulfonic acid and compound A are ionically bonded to form compound 1. It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present invention provides compound 1 substantially free of impurities. As used herein, the term "substantially free of impurities" means that the compound contains no significant amount of extraneous matter. Such extraneous matter may include excess methanesulfonic acid, excess compound A, residual solvents, or any other impurities that may result from the preparation of, and/or isolation of, compound 1. In certain embodiments, at least about 95% by weight of compound 1 is present. In still other embodiments of the invention, at least about 99% by weight of compound 1 is present.

According to one embodiment, compound 1 is present in an amount of at least about 97, 97.5, 98.0, 98.5, 99, 99.5, 99.8 weight percent where the percentages are based on the total weight of the composition. According to another embodiment, compound 1 contains no more than about 3.0 area percent HPLC of total organic impurities and, in certain embodiments, no more than about 1.5 area percent HPLC total organic impurities relative to the total area of the HPLC chromatogram. In other embodiments, compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 1 can exist in a variety of solid forms. Exemplary such forms include polymorphs such as those described herein.

In certain embodiments, compound 1 is a crystalline solid. In other embodiments, compound 1 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the invention, at least about 99% by weight of crystalline compound 1 is present.

It has been found that compound 1 can exist in at least one distinct polymorphic form. In some embodiments, the present invention provides a polymorphic form of Compound 1 referred to herein as Form A. In some embodiments, the present invention provides a polymorphic form of Compound 1 referred to herein as Form B.

In some embodiments, compound 1 is amorphous. In some embodiments, compound 1 is amorphous, and is substantially free of crystalline compound 1.

Form A of Compound 1

In some embodiments, Form A of compound 1 has at least 1, 2, 3, 4 or 5 spectral peak(s) selected from the peaks listed in Table 1 below.

TABLE 1

XRPD Peak Positions for Form A of Compound 1

| Position [°2θ][1] | d-spacing [Å] | Intensity [%] |
|---|---|---|
| 5.8 | 15.3556 | 100 |
| 9.0 | 9.7887 | 4.8 |
| 11.6 | 7.6552 | 50.4 |
| 12.7 | 6.9761 | 2.4 |
| 13.5 | 6.5581 | 7.2 |
| 13.9 | 6.3739 | 6.4 |
| 14.2 | 6.2271 | 20 |
| 15.0 | 5.8855 | 16 |
| 15.3 | 5.7732 | 2.3 |
| 16.2 | 5.467 | 5 |
| 16.9 | 5.2552 | 1.1 |
| 17.4 | 5.099 | 4 |
| 18.1 | 4.8971 | 2.6 |
| 18.8 | 4.7082 | 32.3 |
| 19.4 | 4.5638 | 1.8 |
| 20.7 | 4.2954 | 6.3 |
| 23.2 | 3.8286 | 2.6 |
| 23.9 | 3.716 | 1.7 |
| 24.4 | 3.6524 | 2.1 |
| 24.5 | 3.6304 | 2.1 |
| 24.9 | 3.5667 | 1.7 |
| 25.5 | 3.4859 | 12.2 |
| 25.9 | 3.4353 | 14 |
| 26.5 | 3.3649 | 0.6 |
| 27.2 | 3.2797 | 3.6 |
| 27.6 | 3.2317 | 2.6 |
| 28.1 | 3.1783 | 1.1 |
| 28.3 | 3.1519 | 4.2 |
| 28.7 | 3.1126 | 1.9 |
| 29.2 | 3.0595 | 3.8 |
| 29.5 | 3.0212 | 0.9 |
| 31.1 | 2.8721 | 0.8 |

TABLE 1-continued

XRPD Peak Positions for Form A of Compound 1

| Position [°2θ][1] | d-spacing [Å] | Intensity [%] |
|---|---|---|
| 32.8 | 2.7304 | 0.8 |
| 33.1 | 2.7026 | 0.6 |
| 35.1 | 2.5538 | 1 |
| 35.9 | 2.4998 | 1.1 |
| 39.5 | 2.282 | 0.7 |

[1]In this and all subsequent tables, the position 2θ is within ± 0.2.

In some embodiments, Form A of compound 1 is characterized in that it has one or more peaks in its X-ray powder diffraction pattern selected from those at about 5.8, about 11.6 and about 18.8 degrees 2-theta. In some embodiments, Form A of compound 1 is characterized in that it has two or more peaks in its X-ray powder diffraction pattern selected from those at about 5.8, about 11.6 and about 18.8 degrees 2-theta. In some embodiments, Form A of compound 1 is characterized in that it has all three peaks in its X-ray powder diffraction pattern selected from those at about 5.8, about 11.6 and about 18.8 degrees 2-theta.

Figure 5:
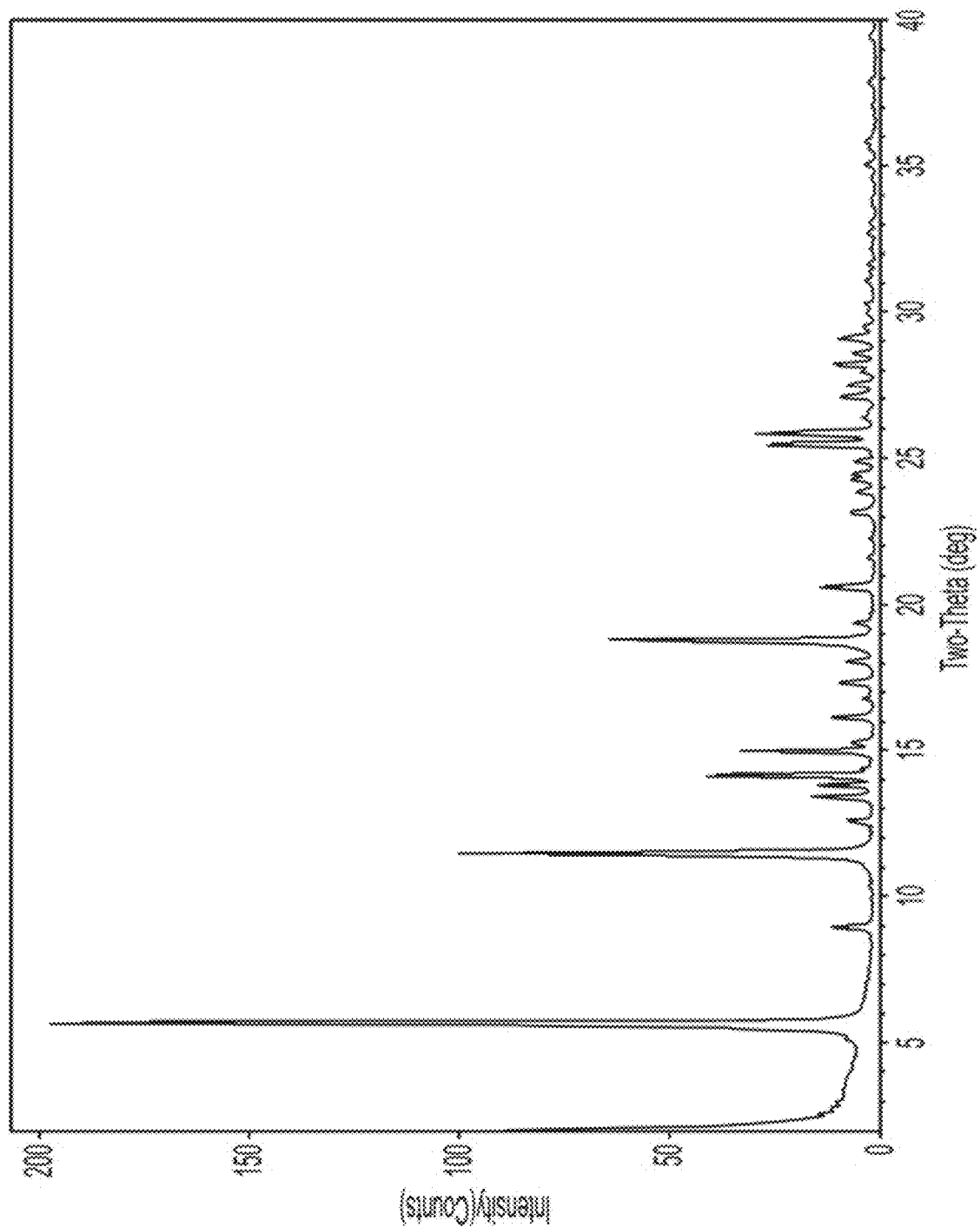
FIG. 5 depicts the XRPD pattern of Compound 1, Form A.

In certain embodiments, the X-ray powder diffraction pattern is substantially similar to the XRPD provided in FIG. 5.

Methods for preparing Form A of compound 1 are described infra.

Form B of Compound 1

In some embodiments, Form B of compound 1 has at least 1, 2, 3, 4 or 5 spectral peak(s) selected from the peaks listed in Table 2 below.

TABLE 2

XRPD Peak Positions for Form B of Compound 1

| Position [°2θ][1] | d-spacing [Å] | Intensity [%] |
|---|---|---|
| 5.1 | 17.2744 | 1.5 |
| 5.6 | 15.7493 | 100 |
| 8.9 | 9.9195 | 1.3 |
| 9.5 | 9.3413 | 1.2 |
| 9.9 | 8.965 | 0.1 |
| 10.2 | 8.7059 | 0.4 |
| 10.9 | 8.1087 | 1.8 |
| 11.2 | 7.8636 | 60 |
| 12.2 | 7.2352 | 0.1 |
| 12.8 | 6.9174 | 0 |
| 13.2 | 6.6957 | 3 |
| 14.0 | 6.3029 | 1.3 |
| 14.7 | 6.0184 | 0.3 |
| 15.0 | 5.9183 | 3.2 |
| 15.7 | 5.643 | 1 |
| 16.2 | 5.4526 | 0.1 |
| 16.9 | 5.2422 | 6.7 |
| 17.5 | 5.0508 | 0 |
| 17.9 | 4.9563 | 0.2 |
| 18.5 | 4.7908 | 1.1 |
| 19.8 | 4.4798 | 0.3 |
| 20.9 | 4.238 | 1.2 |
| 21.6 | 4.1127 | 0.1 |
| 22.0 | 4.0401 | 0.1 |
| 22.5 | 3.9459 | 0.6 |
| 23.7 | 3.7457 | 0.3 |
| 24.2 | 3.6719 | 0.1 |
| 24.6 | 3.6151 | 0.3 |
| 25.6 | 3.4774 | 1.8 |
| 26.0 | 3.4236 | 0.2 |
| 26.6 | 3.3461 | 0.8 |
| 26.8 | 3.321 | 0.2 |
| 28.4 | 3.1454 | 3.2 |
| 29.2 | 3.0548 | 0.5 |

[1]In this and all subsequent tables, the position 2θ is within ± 0.2.

In some embodiments, Form B of compound 1 is characterized in that it has one or more peaks in its X-ray powder diffraction pattern selected from those at about 5.6, about 11.2 and about 16.9 degrees 2-theta. In some embodiments, Form B of compound 1 is characterized in that it has two or more peaks in its X-ray powder diffraction pattern selected from those at about 5.6, about 11.2 and about 16.9 degrees 2-theta. In some embodiments, Form B of compound 1 is characterized in that it has all three peaks in its X-ray powder diffraction pattern selected from those at about 5.6, about 11.2 and about 16.9 degrees 2-theta.

Figure 7:
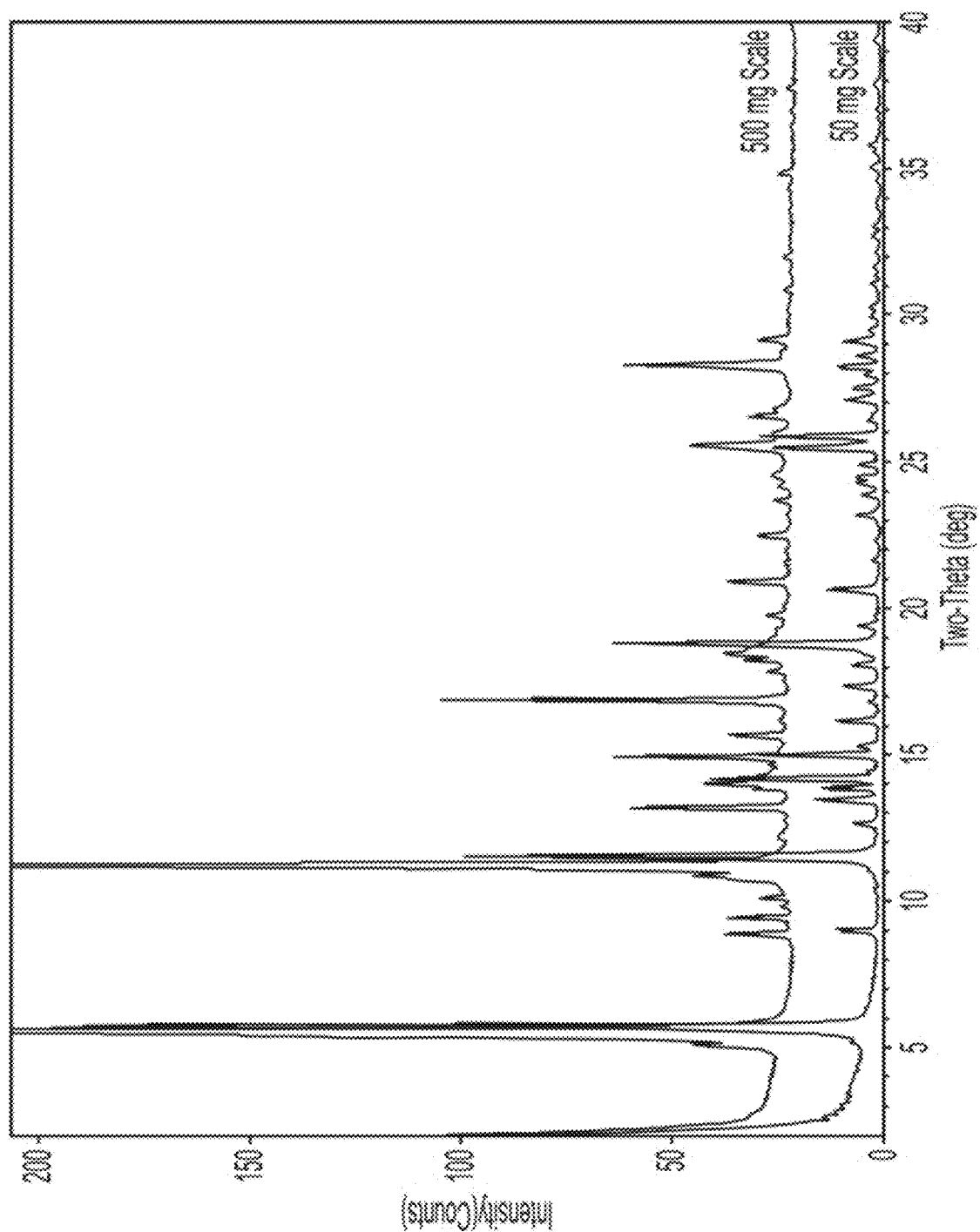
FIG. 7 depicts the XRPD pattern of Compound 1, Form B.

In certain embodiments, the X-ray powder diffraction pattern is substantially similar to the XRPD provided in FIG. 7.

Methods for preparing Form B of compound 1 are described infra.

In some embodiments, the present invention provides compound 1:

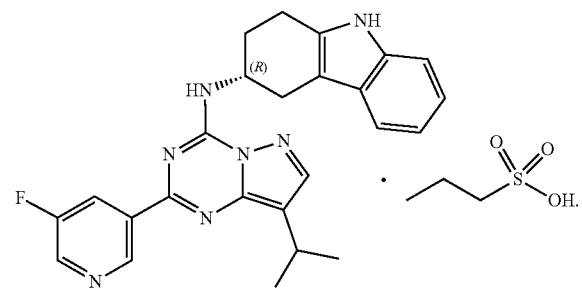

In some embodiments, the present invention provides compound 1, wherein said compound is crystalline.

In some embodiments, the present invention provides compound 1, wherein said compound is a crystalline solid substantially free of amorphous compound 1.

In some embodiments, the present invention provides compound 1, wherein said compound is substantially free of impurities.

In some embodiments, the present invention provides compound 1, wherein said compound has one or more peaks in its XRPD selected from those at 5.8, about 11.6 and about 18.8 degrees 2-theta. In some such embodiments, the present invention provides compound 1, wherein said compound has at least two peaks in its XRPD selected from those at about 5.8, about 11.6 and about 18.8 degrees 2-theta. In some such embodiments, the present invention provides compound 1, wherein said compound is of Form A.

In some embodiments, the present invention provides compound 1, wherein said compound has an XRPD substantially similar to that depicted in FIG. 5.

In some embodiments, the present invention provides compound 1, wherein said compound has one or more peaks in its XRPD selected from those at 5.6, about 11.2 and about 16.9 degrees 2-theta. In some such embodiments, the present invention provides compound 1, wherein said compound has at least two peaks in its XRPD selected from those at about 5.6, about 11.2 and about 16.9 degrees 2-theta. In some such embodiments, the present invention provides compound 1, wherein said compound is of Form B.

In some embodiments, the present invention provides compound 1, wherein said compound has an XRPD substantially similar to that depicted in FIG. 7.

In some embodiments, the present invention provides a composition comprising compound 1 and a pharmaceutically acceptable carrier or excipient.

In some embodiments, the present invention provides a method of inhibiting AHR comprising administering to said patient compound 1 or composition thereof. In some embodiments, the present invention provides a method of inhibiting AHR in a patient comprising administering to said patient compound 1 or composition thereof. In some embodiments, the present invention provides a method of treating one or more disorders associated with activity of AHR comprising administering to said patient compound 1 or composition thereof.

In some embodiments, the present invention provides a method for treating an AHR-mediated disorder comprising the step of administering to a patient in need thereof compound 1 or composition thereof. In some embodiments, the AHR-mediated disorder is a proliferative disease such as cancer or an inflammatory disorder.

Compound 2 (Maleate Salts of Compound A)

According to one embodiment, the present invention provides a maleate salt of compound A, represented by compound 2:

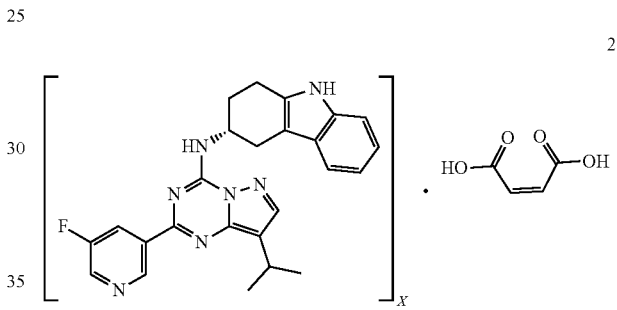

wherein about 1≤x≤about 2.

It will be appreciated by one of ordinary skill in the art that the maleic acid and compound A are ionically bonded to form compound 2. In some embodiments, compound A and maleic acid are in a ratio of about 1:1. In some embodiments, compound A and maleic acid are in a ratio of about 2:1. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In some embodiments, the present invention provides compound 2 substantially free of impurities. As used herein, the term "substantially free of impurities" means that the compound contains no significant amount of extraneous matter. Such extraneous matter may include excess benzenesulfonic acid, excess compound A, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98.0, 98.5, 99, 99.5, 99.8 weight percent where the percentages are based on the total weight of the composition. According to another embodiment, compound 2 contains no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 2 can exist in at least one distinct polymorphic form. In some embodiments, the present invention provides a polymorphic form of Compound 2 referred to herein as Form A. In some embodiments, Form A of Compound 2 comprises compound A and maleic acid in a ratio of about 2:1.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

It has been found that compound 2 can exist in at least one distinct polymorphic form. In some embodiments, the present invention provides a polymorphic form of Compound 2 referred to herein as Form A.

In some embodiments, compound 2 is amorphous. In some embodiments, compound 2 is amorphous, and is substantially free of crystalline compound 2.

Form A of Compound 2

In some embodiments, Form A of compound 2 has at least 1, 2, 3, 4 or 5 spectral peak(s) selected from the peaks listed in Table 3 below.

TABLE 3

XRPD Peak Positions for Form A of Compound 2

| Position [°2θ][1] | d-spacing [Å] | Intensity [%] |
|---|---|---|
| 5.3 | 16.6727 | 100 |
| 6.6 | 13.3333 | 3.8 |
| 8.0 | 11.0992 | 4 |
| 9.6 | 9.2459 | 3.9 |
| 10.6 | 8.3351 | 3.2 |
| 11.3 | 7.8022 | 40.9 |
| 13.3 | 6.6763 | 10.7 |
| 14.1 | 6.2596 | 1.9 |
| 14.7 | 6.0118 | 1.1 |
| 16.0 | 5.5517 | 24.5 |
| 16.8 | 5.2683 | 2 |
| 17.4 | 5.1039 | 1.3 |
| 17.8 | 4.9827 | 3.6 |
| 18.7 | 4.7433 | 1.2 |
| 19.2 | 4.6251 | 2.2 |
| 19.9 | 4.4483 | 0.6 |
| 20.7 | 4.293 | 3.4 |
| 21.3 | 4.1699 | 5.6 |
| 22.7 | 3.9225 | 2.3 |
| 24.0 | 3.7105 | 3.1 |
| 24.5 | 3.6303 | 2.4 |

TABLE 3-continued

XRPD Peak Positions for Form A of Compound 2

| Position [°2θ][1] | d-spacing [Å] | Intensity [%] |
|---|---|---|
| 26.3 | 3.3879 | 1.6 |
| 26.7 | 3.3409 | 2.1 |
| 27.1 | 3.2939 | 2 |
| 27.6 | 3.2338 | 0.6 |
| 28.1 | 3.1769 | 0.9 |
| 28.8 | 3.1015 | 0.3 |
| 29.3 | 3.0447 | 0.6 |
| 31.8 | 2.8079 | 0.5 |
| 32.2 | 2.7771 | 0.5 |

[1]In this and all subsequent tables, the position 2θ is within ± 0.2.

In some embodiments, Form A of compound 2 is characterized in that it has one or more peaks in its X-ray powder diffraction pattern selected from those at about 5.3, about 11.3 and about 16.0 degrees 2-theta. In some embodiments, Form A of compound 2 is characterized in that it has two or more peaks in its X-ray powder diffraction pattern selected from those at about 5.3, about 11.3 and about 16.0 degrees 2-theta. In some embodiments, Form A of compound 2 is characterized in that it has all three peaks in its X-ray powder diffraction pattern selected from those at about 5.3, about 11.3 and about 16.0 degrees 2-theta.

Figure 9:
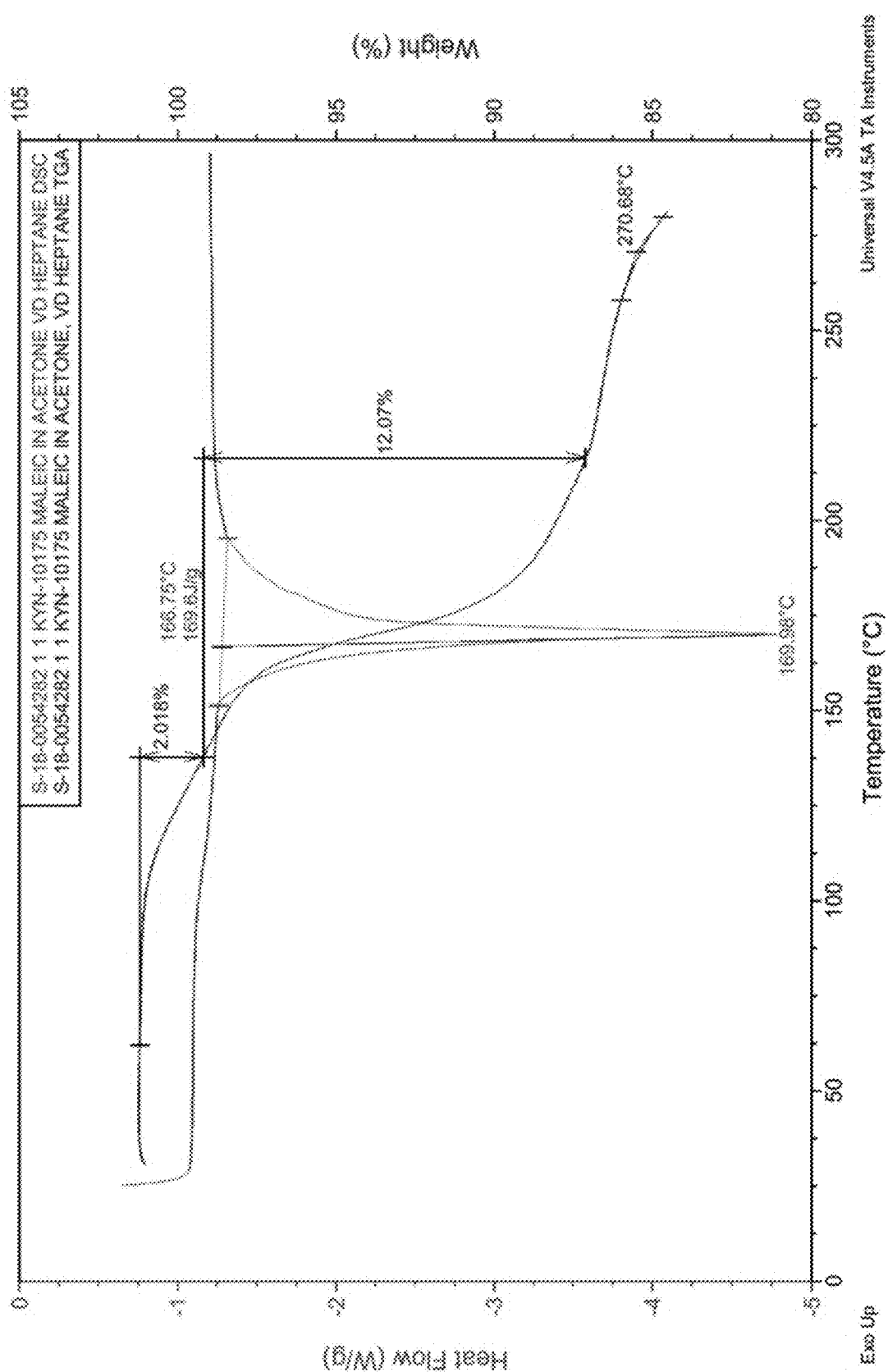
FIG. 9 depicts a TG/DTA trace of Compound 2, Form A.

In certain embodiments, the X-ray powder diffraction pattern is substantially similar to the XRPD provided in FIG. 9.

Methods for preparing Form A of compound 2 are described infra.

In some embodiments, the present invention provides compound 2:

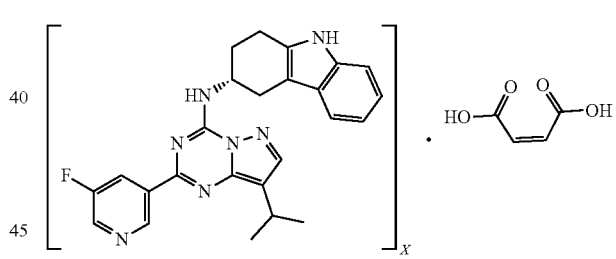

wherein about 1≤x≤about 2.

In some embodiments, the present invention provides compound 2, wherein said compound is crystalline.

In some embodiments, the present invention provides compound 2, wherein said compound is a crystalline solid substantially free of amorphous compound 2.

In some embodiments, the present invention provides compound 2, wherein said compound is substantially free of impurities.

In some embodiments, the present invention provides compound 2, wherein said compound has one or more peaks in its XRPD selected from those at about 5.3, about 11.3 and about 16.0 degrees 2-theta. In some such embodiments, the present invention provides compound 2, wherein said compound has at least two peaks in its XRPD selected from those at about 5.3, about 11.3 and about 16.0 degrees 2-theta. In some such embodiments, the present invention provides compound 2, wherein said compound is of Form A. In some embodiments, Form A of Compound 2 comprises compound A and maleic acid in a ratio of about 2:1.

In some embodiments, the present invention provides compound 2, wherein said compound has an XRPD substantially similar to that depicted in FIG. 9.

In some embodiments, the present invention provides a composition comprising compound 2 and a pharmaceutically acceptable carrier or excipient.

In some embodiments, the present invention provides a method of inhibiting AHR comprising administering to said patient compound 2 or composition thereof. In some embodiments, the present invention provides a method of inhibiting AHR in a patient comprising administering to said patient compound 2 or composition thereof. In some embodiments, the present invention provides a method of treating one or more disorders associated with activity of AHR comprising administering to said patient compound 2 or composition thereof.

In some embodiments, the present invention provides a method for treating an AHR-mediated disorder comprising the step of administering to a patient in need thereof compound 2 or composition thereof. In some embodiments, the AHR-mediated disorder is a proliferative disease such as cancer or an inflammatory disorder.

Compound 3 (Mesylate Salts of Compound A)

According to one embodiment, the present invention provides a mesylate salt of compound A, represented by compound 3:

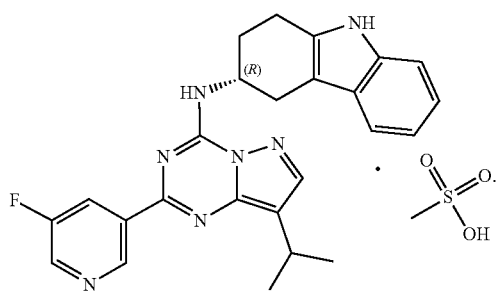

3

It will be appreciated by one of ordinary skill in the art that the methanesulfonic acid and compound A are ionically bonded to form compound 3. It is contemplated that compound 3 can exist in a variety of physical forms. For example, compound 3 can be in solution, suspension, or in solid form. In certain embodiments, compound 3 is in solid form. When compound 3 is in solid form, said compound may be amorphous, crystalline, or a mixture thereof. Exemplary solid forms are described in more detail below.

In some embodiments, the present invention provides compound 3 substantially free of impurities. As used herein, the term "substantially free of impurities" means that the compound contains no significant amount of extraneous matter. Such extraneous matter may include excess sulfuric acid, excess compound A, residual solvents, or any other impurities that may result from the preparation of, and/or isolation of, compound 3. In certain embodiments, at least about 95% by weight of compound 3 is present. In still other embodiments of the invention, at least about 99% by weight of compound 3 is present.

According to one embodiment, compound 3 is present in an amount of at least about 97, 97.5, 98.0, 98.5, 99, 99.5, 99.8 weight percent where the percentages are based on the total weight of the composition. According to another embodiment, compound 3 contains no more than about 3.0 area percent HPLC of total organic impurities and, in certain embodiments, no more than about 1.5 area percent HPLC total organic impurities relative to the total area of the HPLC chromatogram. In other embodiments, compound 3 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 3 is also meant to include all tautomeric forms of compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 3 can exist in at least two distinct polymorphic forms. In some embodiments, the present invention provides a polymorphic form of Compound 3 referred to herein as Form A. In some embodiments, the present invention provides a polymorphic form of Compound 3 referred to herein as Form B.

In certain embodiments, compound 3 is a crystalline solid. In other embodiments, compound 3 is a crystalline solid substantially free of amorphous compound 3. As used herein, the term "substantially free of amorphous compound 3" means that the compound contains no significant amount of amorphous compound 3. In certain embodiments, at least about 95% by weight of crystalline compound 3 is present. In still other embodiments of the invention, at least about 99% by weight of crystalline compound 3 is present.

In some embodiments, compound 3 is amorphous. In some embodiments, compound 3 is amorphous, and is substantially free of crystalline compound 3.

Form A of Compound 3

In some embodiments, Form A of compound 3 has at least 1, 2, 3, 4 or 5 spectral peak(s) selected from the peaks listed in Table 4 below.

TABLE 4

XRPD Peak Positions for Form A of Compound 3

| Position [°2θ][1] | d-spacing [Å] | Intensity [%] |
| --- | --- | --- |
| 5.1 | 17.2728 | 1.2 |
| 5.6 | 15.7025 | 100 |
| 9.0 | 9.7695 | 3.6 |
| 10.2 | 8.7061 | 0.3 |
| 11.0 | 8.0007 | 2.7 |
| 11.2 | 7.8648 | 35 |
| 12.1 | 7.3154 | 0.4 |
| 12.4 | 7.1465 | 0.3 |
| 13.3 | 6.6505 | 2.9 |
| 14.0 | 6.313 | 3.2 |
| 14.3 | 6.1969 | 2.1 |
| 15.3 | 5.7988 | 6.3 |
| 15.8 | 5.6164 | 1.7 |
| 16.3 | 5.4343 | 0.4 |
| 16.9 | 5.2456 | 8 |
| 18.0 | 4.9265 | 0.4 |
| 18.4 | 4.8306 | 0.6 |
| 18.7 | 4.7514 | 1.9 |
| 18.9 | 4.7028 | 1.8 |
| 19.5 | 4.5477 | 0.7 |
| 20.0 | 4.4386 | 0.4 |
| 21.0 | 4.229 | 1.2 |
| 22.0 | 4.0295 | 0.4 |
| 24.2 | 3.6743 | 0.5 |
| 25.5 | 3.4972 | 5.3 |
| 25.9 | 3.4328 | 0.7 |

TABLE 4-continued

XRPD Peak Positions for Form A of Compound 3

| Position [°2θ][1] | d-spacing [Å] | Intensity [%] |
|---|---|---|
| 26.7 | 3.3316 | 1.6 |
| 28.3 | 3.1506 | 2.5 |
| 29.2 | 3.053 | 0.5 |

[1] In this and all subsequent tables, the position 2θ is within ± 0.2.

In some embodiments, Form A of compound 3 is characterized in that it has one or more peaks in its X-ray powder diffraction pattern selected from those at about 5.6, about 11.2 and about 16.9 degrees 2-theta. In some embodiments, Form A of compound 3 is characterized in that it has two or more peaks in its X-ray powder diffraction pattern selected from those at about 5.6, about 11.2 and about 16.9 degrees 2-theta. In some embodiments, Form A of compound 3 is characterized in that it has all three peaks in its X-ray powder diffraction pattern selected from those at about 5.6, about 11.2 and about 16.9 degrees 2-theta.

Figure 11:
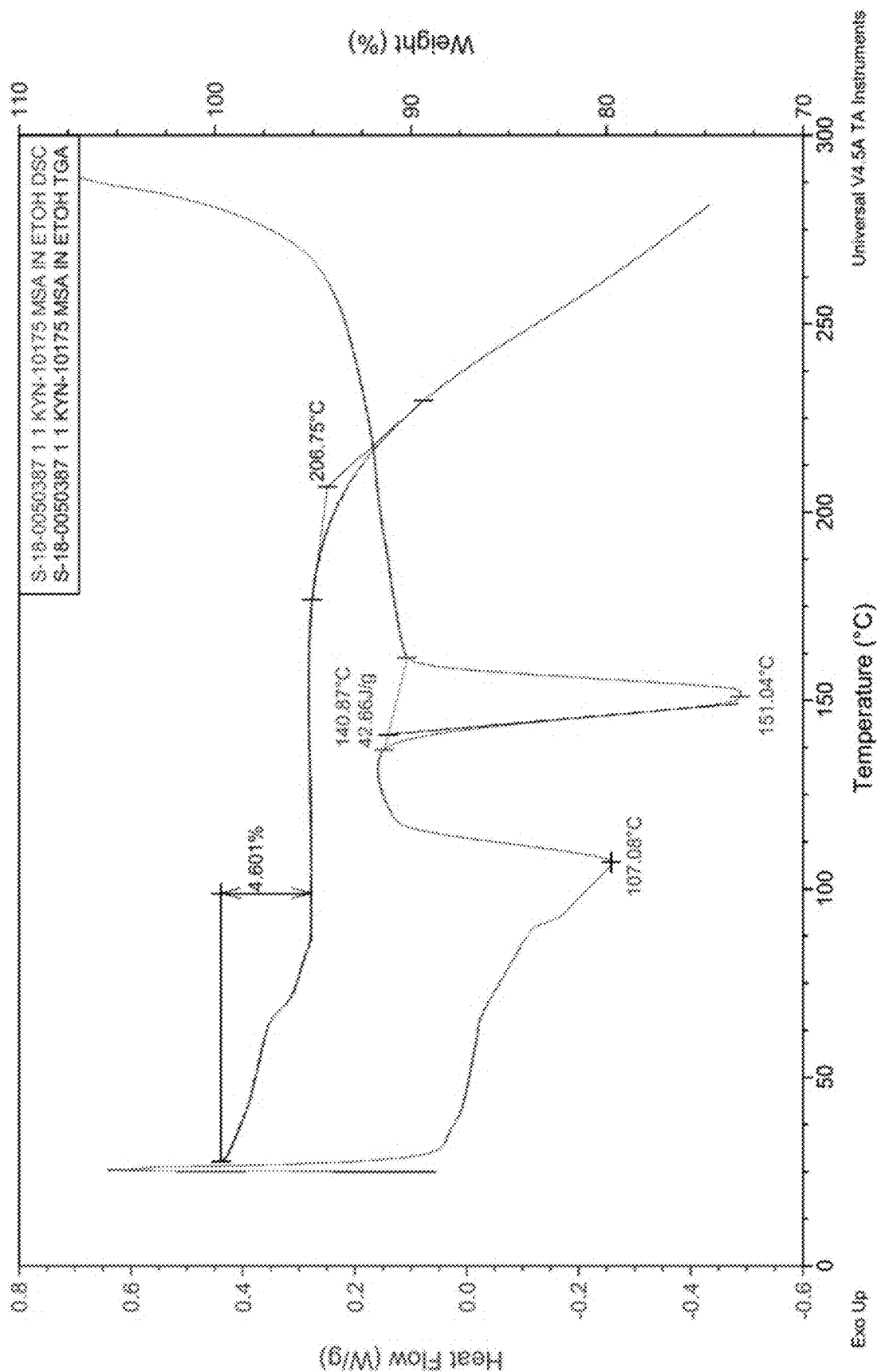
FIG. 11 depicts a TG/DTA trace of Compound 3, Form A.

In certain embodiments, the X-ray powder diffraction pattern is substantially similar to the XRPD provided in FIG. 11.

Methods for preparing Form A of compound 3 are described infra.

Form B of Compound 3

In some embodiments, Form B of compound 3 has at least 1, 2, 3, 4 or 5 spectral peak(s) selected from the peaks listed in Table 5 below.

TABLE 5

XRPD Peak Positions for Form B of Compound 3

| Position [°2θ][1] | d (Angstroms) | Intensity [%] |
|---|---|---|
| 6.0 | 14.7036 | 100 |
| 11.6 | 7.6195 | 10 |
| 12.1 | 7.3357 | 32.3 |
| 13.6 | 6.5115 | 2.1 |
| 14.6 | 6.0801 | 3.1 |
| 15.6 | 5.66 | 2 |
| 16.1 | 5.514 | 0.6 |
| 17.6 | 5.0376 | 4.5 |
| 18.1 | 4.8948 | 12.5 |
| 19.8 | 4.4702 | 1 |
| 20.1 | 4.4033 | 3.3 |
| 20.8 | 4.2687 | 0.2 |
| 21.1 | 4.2034 | 1.3 |
| 21.9 | 4.0542 | 2.2 |
| 22.2 | 4.0022 | 4.2 |
| 22.6 | 3.9386 | 0.5 |
| 23.0 | 3.8694 | 0.3 |
| 23.5 | 3.7822 | 1.2 |
| 24.3 | 3.6649 | 0.3 |
| 25.1 | 3.5465 | 1.8 |
| 26.9 | 3.3177 | 1.9 |
| 27.4 | 3.2583 | 3 |
| 28.3 | 3.1563 | 0.9 |
| 29.4 | 3.0401 | 0.9 |

[1] In this and all subsequent tables, the position 2θ is within ± 0.2.

In some embodiments, Form B of compound 3 is characterized in that it has one or more peaks in its X-ray powder diffraction pattern selected from those at about 6.0, about 12.1 and about 18.1 degrees 2-theta. In some embodiments, Form B of compound 3 is characterized in that it has two or more peaks in its X-ray powder diffraction pattern selected from those at about 6.0, about 12.1 and about 18.1 degrees 2-theta. In some embodiments, Form B of compound 3 is characterized in that it has all three peaks in its X-ray powder diffraction pattern selected from those at about 6.0, about 12.1 and about 18.1 degrees 2-theta.

Figure 13:
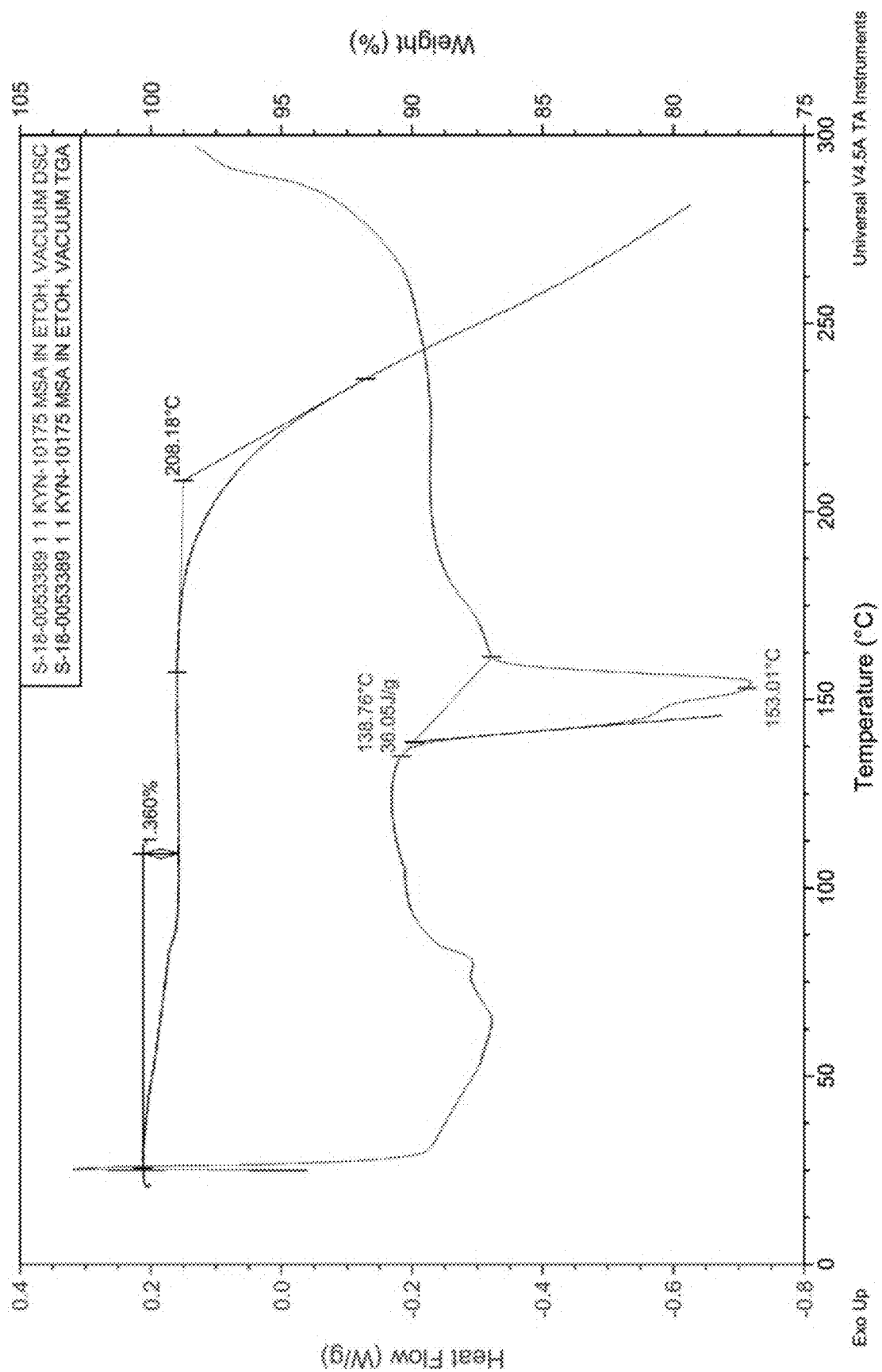
FIG. 13 depicts a TG/DTA trace of Compound 3, Form B.

In certain embodiments, the X-ray powder diffraction pattern is substantially similar to the XRPD provided in FIG. 13.

Methods for preparing Form B of compound 3 are described infra.

In some embodiments, the present invention provides compound 3:

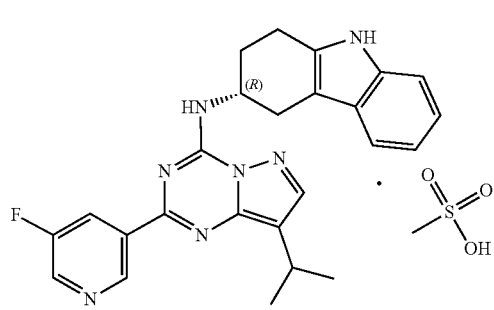

In some embodiments, the present invention provides compound 3, wherein said compound is crystalline.

In some embodiments, the present invention provides compound 3, wherein said compound is a crystalline solid substantially free of amorphous compound 3.

In some embodiments, the present invention provides compound 3, wherein said compound is substantially free of impurities.

In some embodiments, the present invention provides compound 3, wherein said compound has one or more peaks in its XRPD selected from those at about 5.6, about 11.2 and about 16.9 degrees 2-theta. In some such embodiments, the present invention provides compound 3, wherein said compound has at least two peaks in its XRPD selected from those at about 5.6, about 11.2 and about 16.9 degrees 2-theta. In some such embodiments, the present invention provides compound 3, wherein said compound is of Form A.

In some embodiments, the present invention provides compound 3, wherein said compound has an XRPD substantially similar to that depicted in FIG. 11.

In some embodiments, the present invention provides compound 3, wherein said compound has one or more peaks in its XRPD selected from those at about 6.0, about 12.1 and about 18.1 degrees 2-theta. In some such embodiments, the present invention provides compound 3, wherein said compound has at least two peaks in its XRPD selected from those at about 6.0, about 12.1 and about 18.1 degrees 2-theta. In some such embodiments, the present invention provides compound 3, wherein said compound is of Form B.

In some embodiments, the present invention provides compound 3, wherein said compound has an XRPD substantially similar to that depicted in FIG. 13.

In some embodiments, the present invention provides a composition comprising compound 3 and a pharmaceutically acceptable carrier or excipient.

In some embodiments, the present invention provides a method of inhibiting AHR comprising administering to said patient compound 3 or composition thereof. In some embodiments, the present invention provides a method of inhibiting AHR in a patient comprising administering to said patient compound 3 or composition thereof. In some embodiments, the present invention provides a method of treating one or more disorders associated with activity of AHR comprising administering to said patient compound 3 or composition thereof.

In some embodiments, the present invention provides a method for treating an AHR-mediated disorder comprising the step of administering to a patient in need thereof compound 3 or composition thereof. In some embodiments, the AHR-mediated disorder is a proliferative disease such as cancer or an inflammatory disorder.

Compound 4 (Napsylate Salts of Compound A)

According to one embodiment, the present invention provides a napsylate salt of compound A, represented by compound 4:

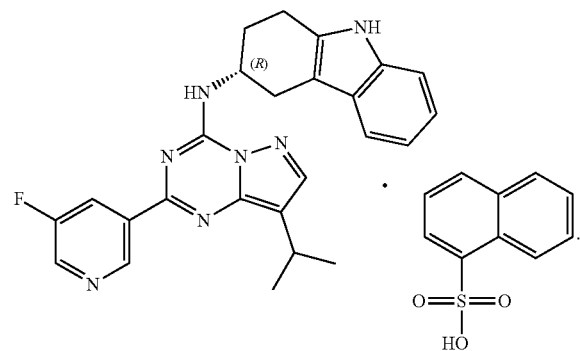

4

It will be appreciated by one of ordinary skill in the art that the napthalenesulfonic acid and compound A are ionically bonded to form compound 4. It is contemplated that compound 4 can exist in a variety of physical forms. For example, compound 4 can be in solution, suspension, or in solid form. In certain embodiments, compound 4 is in solid form. When compound 4 is in solid form, said compound may be amorphous, crystalline, or a mixture thereof. Exemplary solid forms are described in more detail below.

In some embodiments, the present invention provides compound 4 substantially free of impurities. As used herein, the term "substantially free of impurities" means that the compound contains no significant amount of extraneous matter. Such extraneous matter may include excess p-toluenesulfonic acid, excess compound A, residual solvents, or any other impurities that may result from the preparation of, and/or isolation of, compound 4. In certain embodiments, at least about 95% by weight of compound 4 is present. In still other embodiments of the invention, at least about 99% by weight of compound 4 is present.

According to one embodiment, compound 4 is present in an amount of at least about 97, 97.5, 98.0, 98.5, 99, 99.5, 99.8 weight percent where the percentages are based on the total weight of the composition. According to another embodiment, compound 4 contains no more than about 3.0 area percent HPLC of total organic impurities and, in certain embodiments, no more than about 1.5 area percent HPLC total organic impurities relative to the total area of the HPLC chromatogram. In other embodiments, compound 4 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 4 is also meant to include all tautomeric forms of compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 4 can exist in at least distinct solid form. Exemplary such forms include polymorphs such as those described herein.

It has been found that compound 4 can exist in at least one distinct polymorphic form. In some embodiments, the present invention provides a polymorphic form of Compound 4 referred to herein as Form A.

In certain embodiments, compound 4 is a crystalline solid. In other embodiments, compound 4 is a crystalline solid substantially free of amorphous compound 4. As used herein, the term "substantially free of amorphous compound 4" means that the compound contains no significant amount of amorphous compound 4. In certain embodiments, at least about 95% by weight of crystalline compound 4 is present. In still other embodiments of the invention, at least about 99% by weight of crystalline compound 4 is present.

In some embodiments, compound 4 is amorphous. In some embodiments, compound 4 is amorphous, and is substantially free of crystalline compound 4.

Form A of Compound 4

In some embodiments, Form A of compound 4 has at least 1, 2, 3, 4 or 5 spectral peak(s) selected from the peaks listed in Table 6 below.

TABLE 6

XRPD Peak Positions for Form A of Compound 4

| Position [°2θ][1] | d (Angstroms) | Intensity [%] |
|---|---|---|
| 6.8 | 13.0644 | 1.1 |
| 7.5 | 11.81 | 100 |
| 7.8 | 11.2555 | 9.4 |
| 8.4 | 10.5306 | 78.5 |
| 9.5 | 9.3437 | 5.7 |
| 9.8 | 9.0463 | 7.2 |
| 9.9 | 8.8891 | 7.5 |
| 11.1 | 7.9975 | 8.2 |
| 11.9 | 7.404 | 5.2 |
| 12.6 | 7.0284 | 1.4 |
| 12.9 | 6.8706 | 1.6 |
| 13.5 | 6.5355 | 5 |
| 13.8 | 6.4284 | 11.9 |
| 14.5 | 6.1263 | 26.4 |
| 14.7 | 6.029 | 1.2 |
| 15.1 | 5.8748 | 8.3 |
| 15.8 | 5.6186 | 10.1 |
| 16.1 | 5.5086 | 4 |
| 16.5 | 5.3844 | 20.1 |
| 16.6 | 5.3221 | 1.8 |
| 16.8 | 5.2691 | 1.7 |
| 17.3 | 5.1223 | 1.3 |
| 18.1 | 4.9044 | 11.6 |
| 19.1 | 4.6279 | 4.7 |
| 19.6 | 4.5254 | 11.4 |
| 19.7 | 4.496 | 9.8 |
| 20.1 | 4.424 | 47.9 |
| 20.6 | 4.2976 | 7.6 |
| 20.9 | 4.2364 | 2.5 |
| 21.5 | 4.1352 | 0.3 |
| 21.8 | 4.0652 | 1.1 |
| 22.0 | 4.0293 | 5.8 |
| 22.4 | 3.9624 | 28.3 |
| 22.9 | 3.8768 | 1.7 |
| 23.7 | 3.745 | 7.5 |

TABLE 6-continued

XRPD Peak Positions for Form A of Compound 4

| Position [°2θ][1] | d (Angstroms) | Intensity [%] |
|---|---|---|
| 24.6 | 3.6159 | 5.8 |
| 24.8 | 3.5884 | 3.8 |
| 25.2 | 3.5259 | 2.9 |

[1]In this and all subsequent tables, the position 2θ is within ± 0.2.

In some embodiments, Form A of compound 4 is characterized in that it has one or more peaks in its X-ray powder diffraction pattern selected from those at about 7.5, about 8.4 and about 20.1 degrees 2-theta. In some embodiments, Form A of compound 4 is characterized in that it has two or more peaks in its X-ray powder diffraction pattern selected from those at about 7.5, about 8.4 and about 20.1 degrees 2-theta. In some embodiments, Form A of compound 4 is characterized in that it has all three peaks in its X-ray powder diffraction pattern selected from those at about 7.5, about 8.4 and about 20.1 degrees 2-theta.

Figure 15:
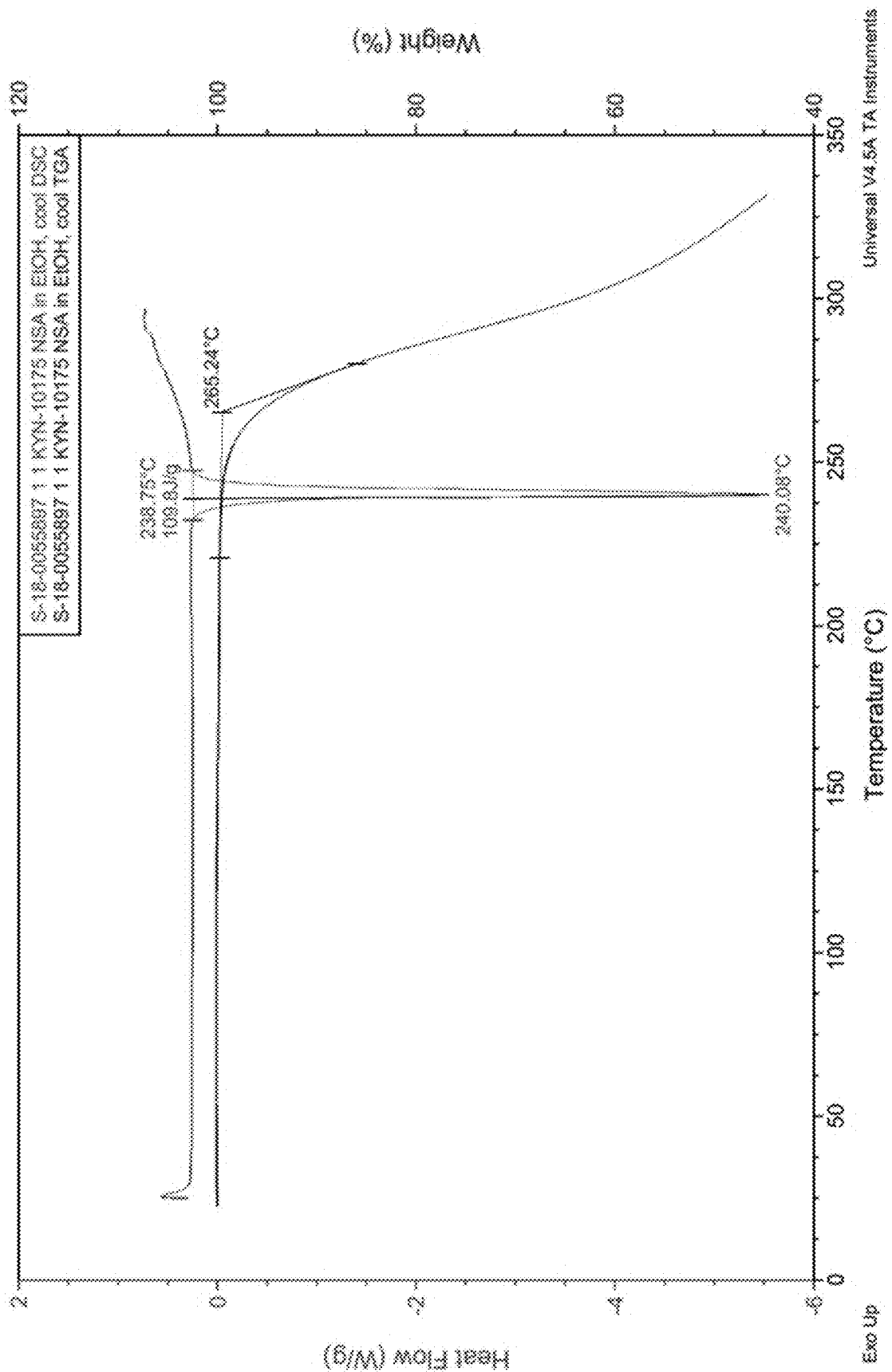
FIG. 15 depicts a TG/DTA trace of Compound 4, Form A.

In certain embodiments, the X-ray powder diffraction pattern is substantially similar to the XRPD provided in FIG. 15.

Methods for preparing Form A of compound 4 are described infra.

In some embodiments, the present invention provides compound 4:

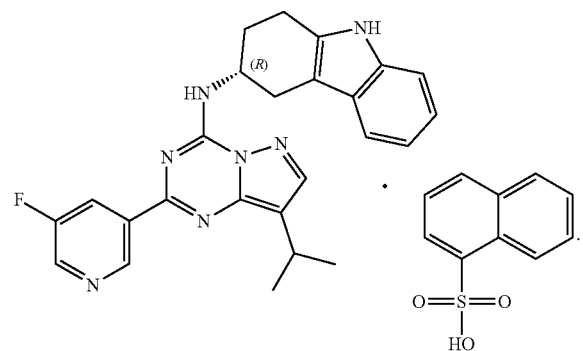

4

In some embodiments, the present invention provides compound 4, wherein said compound is crystalline.

In some embodiments, the present invention provides compound 4, wherein said compound is a crystalline solid substantially free of amorphous compound 4.

In some embodiments, the present invention provides compound 4, wherein said compound is substantially free of impurities.

In some embodiments, the present invention provides compound 4, wherein said compound has one or more peaks in its XRPD selected from those at about 7.5, about 8.4 and about 20.1 degrees 2-theta. In some such embodiments, the present invention provides compound 4, wherein said compound has at least two peaks in its XRPD selected from those at about 7.5, about 8.4 and about 20.1 degrees 2-theta. In some such embodiments, the present invention provides compound 4, wherein said compound is of Form A.

In some embodiments, the present invention provides compound 4, wherein said compound has an XRPD substantially similar to that depicted in FIG. 15.

In some embodiments, the present invention provides a composition comprising compound 4 and a pharmaceutically acceptable carrier or excipient.

In some embodiments, the present invention provides a method of inhibiting AHR comprising administering to said patient compound 4 or composition thereof. In some embodiments, the present invention provides a method of inhibiting AHR in a patient comprising administering to said patient compound 4 or composition thereof. In some embodiments, the present invention provides a method of treating one or more disorders associated with activity of AHR comprising administering to said patient compound 4 or composition thereof.

In some embodiments, the present invention provides a method for treating an AHR-mediated disorder comprising the step of administering to a patient in need thereof compound 4 or composition thereof. In some embodiments, the AHR-mediated disorder is a proliferative disease such as cancer or an inflammatory disorder.

Compound 5 (Oxalate Salts of Compound A)

According to one embodiment, the present invention provides an oxalate salt of compound A, represented by compound 5:

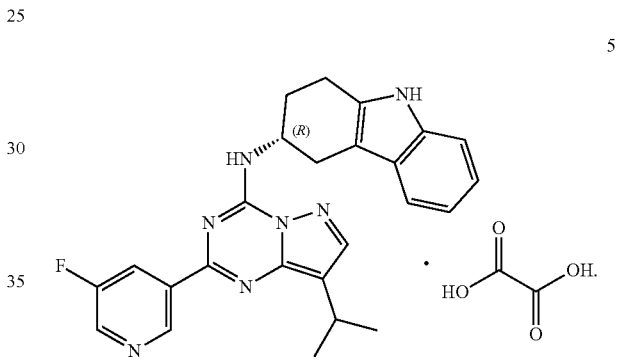

5

It will be appreciated by one of ordinary skill in the art that the oxalic acid and compound A are ionically bonded to form compound 5. It is contemplated that compound 5 can exist in a variety of physical forms. For example, compound 5 can be in solution, suspension, or in solid form. In certain embodiments, compound 5 is in solid form. When compound 5 is in solid form, said compound may be amorphous, crystalline, or a mixture thereof. Exemplary solid forms are described in more detail below.

In some embodiments, the present invention provides compound 5 substantially free of impurities. As used herein, the term "substantially free of impurities" means that the compound contains no significant amount of extraneous matter. Such extraneous matter may include excess hydrochloric acid, excess compound A, residual solvents, or any other impurities that may result from the preparation of, and/or isolation of, compound 5. In certain embodiments, at least about 95% by weight of compound 5 is present. In still other embodiments of the invention, at least about 99% by weight of compound 5 is present.

According to one embodiment, compound 5 is present in an amount of at least about 97, 97.5, 98.0, 98.5, 99, 99.5, 99.8 weight percent where the percentages are based on the total weight of the composition. According to another embodiment, compound 5 contains no more than about 3.0 area percent HPLC of total organic impurities and, in certain embodiments, no more than about 1.5 area percent HPLC total organic impurities relative to the total area of the HPLC chromatogram. In other embodiments, compound 5 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 5 is also meant to include all tautomeric forms of compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 5 can exist in at least one distinct polymorphic form. In some embodiments, the present invention provides a polymorphic form of Compound 5 referred to herein as Form A.

In certain embodiments, compound 5 is a crystalline solid. In other embodiments, compound 5 is a crystalline solid substantially free of amorphous compound 5. As used herein, the term "substantially free of amorphous compound 5" means that the compound contains no significant amount of amorphous compound 5. In certain embodiments, at least about 95% by weight of crystalline compound 5 is present. In still other embodiments of the invention, at least about 99% by weight of crystalline compound 5 is present.

In some embodiments, compound 5 is amorphous. In some embodiments, compound 5 is amorphous, and is substantially free of crystalline compound 5.

Form A of Compound 5

In some embodiments, Form A of compound 5 has at least 1, 2, 3, 4 or 5 spectral peak(s) selected from the peaks listed in Table 7 below.

TABLE 7

XRPD Peak Positions for Form A of Compound 5

| Position [°2θ][1] | d-spacing [Å] | Intensity [%] |
|---|---|---|
| 6.4 | 13.7901 | 100 |
| 7.1 | 12.4378 | 20.2 |
| 11.4 | 7.7871 | 4.9 |
| 12.7 | 6.9614 | 63.9 |
| 14.4 | 6.1639 | 6 |
| 17.5 | 5.0766 | 16.5 |
| 18.3 | 4.8405 | 3.3 |
| 19.2 | 4.6288 | 3.2 |
| 21.1 | 4.2167 | 2.7 |
| 22.3 | 3.9765 | 1.7 |
| 23.1 | 3.8472 | 8.2 |
| 27.3 | 3.2647 | 1.7 |
| 29.0 | 3.0719 | 0.9 |

[1]In this and all subsequent tables, the position 2θ is within ± 0.2.

In some embodiments, Form A of compound 5 is characterized in that it has one or more peaks in its X-ray powder diffraction pattern selected from those at about 6.4, about 7.1 and about 12.7 degrees 2-theta. In some embodiments, Form A of compound 5 is characterized in that it has two or more peaks in its X-ray powder diffraction pattern selected from those at about 6.4, about 7.1 and about 12.7 degrees 2-theta. In some embodiments, Form A of compound 5 is characterized in that it has all three peaks in its X-ray powder diffraction pattern selected from those at about 6.4, about 7.1 and about 12.7 degrees 2-theta.

Figure 17:
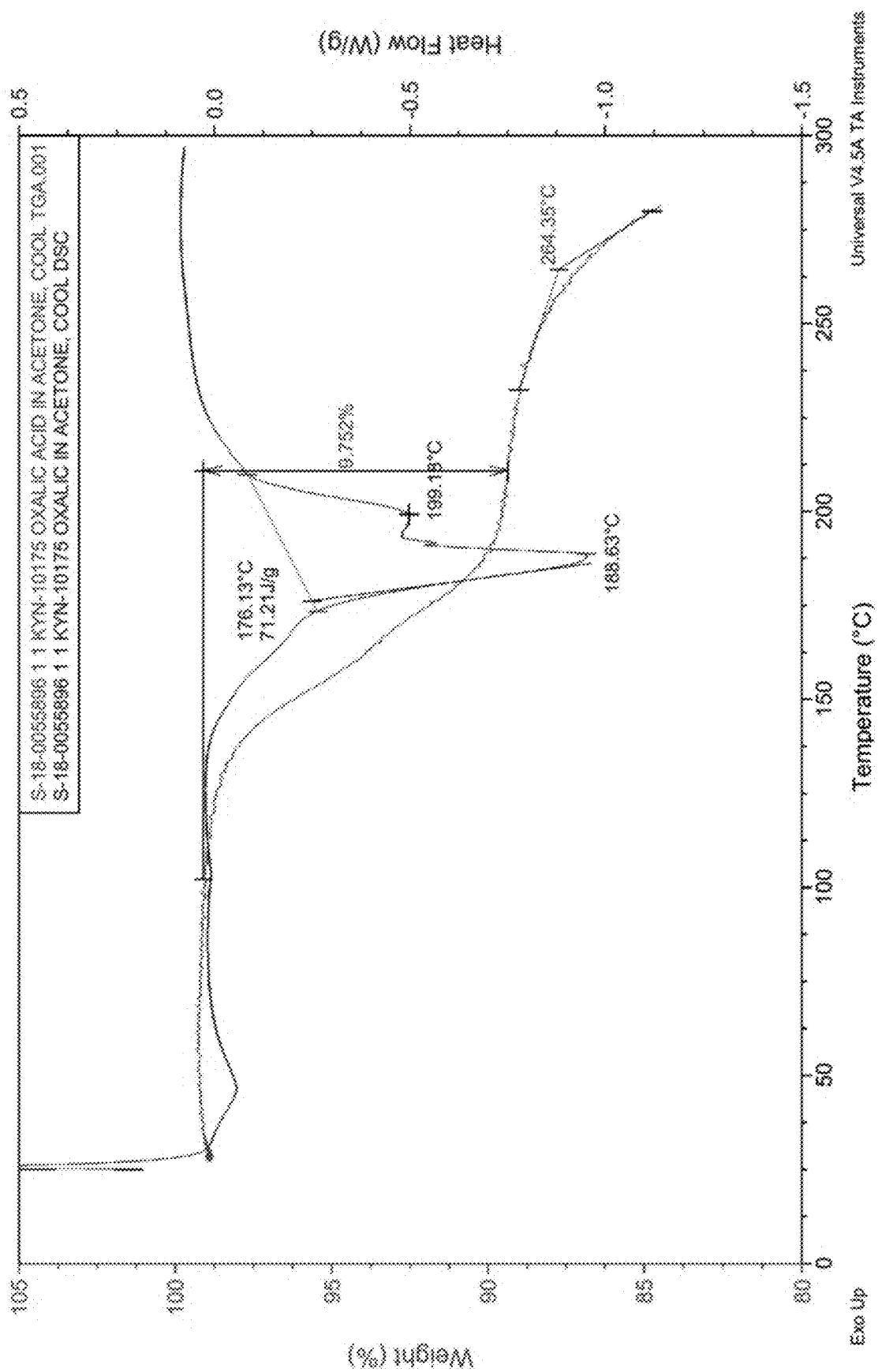
FIG. 17 depicts a TG/DTA trace of Compound 5, Form A.

In certain embodiments, the X-ray powder diffraction pattern is substantially similar to the XRPD provided in FIG. 17.

Methods for preparing Form A of compound 5 are described infra.

In some embodiments, the present invention provides compound 5:

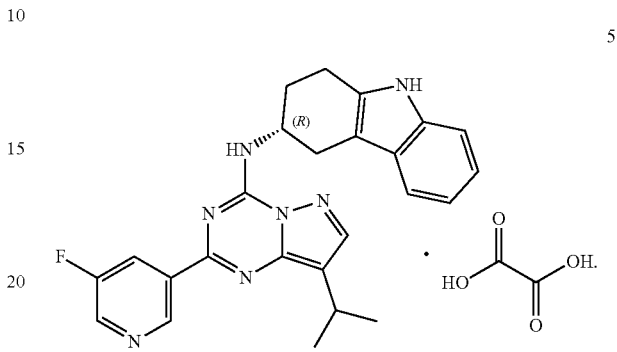

In some embodiments, the present invention provides compound 5, wherein said compound is crystalline.

In some embodiments, the present invention provides compound 5, wherein said compound is a crystalline solid substantially free of amorphous compound 5.

In some embodiments, the present invention provides compound 5, wherein said compound is substantially free of impurities.

In some embodiments, the present invention provides compound 5, wherein said compound has one or more peaks in its XRPD selected from those at about 6.4, about 7.1 and about 12.7 degrees 2-theta. In some such embodiments, the present invention provides compound 5, wherein said compound has at least two peaks in its XRPD selected from those at about 6.4, about 7.1 and about 12.7 degrees 2-theta. In some such embodiments, the present invention provides compound 5, wherein said compound is of Form A.

In some embodiments, the present invention provides compound 5, wherein said compound has an XRPD substantially similar to that depicted in FIG. 17.

In some embodiments, the present invention provides a composition comprising compound 5 and a pharmaceutically acceptable carrier or excipient.

In some embodiments, the present invention provides a method of inhibiting AHR comprising administering to said patient compound 5 or composition thereof. In some embodiments, the present invention provides a method of inhibiting AHR in a patient comprising administering to said patient compound 5 or composition thereof. In some embodiments, the present invention provides a method of treating one or more disorders associated with activity of AHR comprising administering to said patient compound 5 or composition thereof.

In some embodiments, the present invention provides a method for treating an AHR-mediated disorder comprising the step of administering to a patient in need thereof compound 5 or composition thereof. In some embodiments, the AHR-mediated disorder is a proliferative disease such as cancer or an inflammatory disorder.

Compound 6 (Tartrate Salts of Compound A)

According to one embodiment, the present invention provides an tartrate salt of compound A, represented by compound 6:

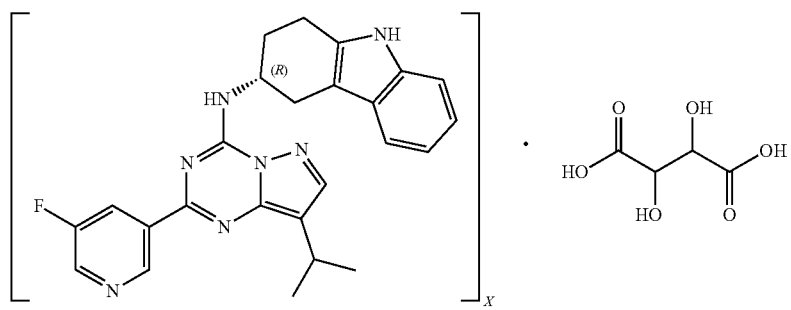

6 wherein about 1≤x≤about 2.

It will be appreciated by one of ordinary skill in the art that the tartaric acid and compound A are ionically bonded to form compound 6. In some embodiments, compound A and tartaric acid are in a ratio of about 1:1. In some embodiments, compound A and tartaric acid are in a ratio of about 2:1. It is contemplated that compound 6 can exist in a variety of physical forms. For example, compound 6 can be in solution, suspension, or in solid form. In certain embodiments, compound 6 is in solid form. When compound 6 is in solid form, said compound may be amorphous, crystalline, or a mixture thereof. Exemplary solid forms are described in more detail below.

In some embodiments, the present invention provides compound 6 substantially free of impurities. As used herein, the term "substantially free of impurities" means that the compound contains no significant amount of extraneous matter. Such extraneous matter may include excess oxalic acid, excess compound A, residual solvents, or any other impurities that may result from the preparation of, and/or isolation of, compound 6. In certain embodiments, at least about 95% by weight of compound 6 is present. In still other embodiments of the invention, at least about 99% by weight of compound 6 is present.

According to one embodiment, compound 6 is present in an amount of at least about 97, 97.5, 98.0, 98.5, 99, 99.5, 99.8 weight percent where the percentages are based on the total weight of the composition. According to another embodiment, compound 6 contains no more than about 3.0 area percent HPLC of total organic impurities and, in certain embodiments, no more than about 1.5 area percent HPLC total organic impurities relative to the total area of the HPLC chromatogram. In other embodiments, compound 6 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 6 is also meant to include all tautomeric forms of compound 6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 6 can exist in at least two distinct polymorphic forms. In some embodiments, the present invention provides a polymorphic form of Compound 6 referred to herein as Form A. In some embodiments, the present invention provides a polymorphic form of Compound 6 referred to herein as Form B. In some embodiments, Form A of Compound 6 comprises compound A and tartaric acid in a ratio of about 1:1. In some embodiments, Form B of Compound 6 comprises compound A and tartaric acid in a ratio of about 2:1.

In certain embodiments, compound 6 is a crystalline solid. In other embodiments, compound 6 is a crystalline solid substantially free of amorphous compound 6. As used herein, the term "substantially free of amorphous compound 6" means that the compound contains no significant amount of amorphous compound 6. In certain embodiments, at least about 95% by weight of crystalline compound 6 is present. In still other embodiments of the invention, at least about 99% by weight of crystalline compound 6 is present.

In some embodiments, compound 6 is amorphous. In some embodiments, compound 6 is amorphous, and is substantially free of crystalline compound 6.

Form A of Compound 6

In some embodiments, Form A of compound 6 has at least 1, 2, 3, 4 or 5 spectral peak(s) selected from the peaks listed in Table 8 below.

TABLE 8

XRPD Peak Positions for Form A of Compound 6

| Position [°2θ][1] | d-spacing [Å] | Intensity [%] |
|---|---|---|
| 5.5 | 16.1924 | 100 |
| 7.0 | 12.6864 | 1.4 |
| 8.2 | 10.8305 | 7.5 |
| 8.4 | 10.5158 | 9 |
| 9.1 | 9.6845 | 0.7 |
| 10.3 | 8.5415 | 1.6 |
| 11.1 | 7.9331 | 15.7 |
| 13.4 | 6.6022 | 1.1 |
| 14.5 | 6.1046 | 5 |
| 15.6 | 5.6633 | 4.8 |
| 16.3 | 5.4202 | 4.5 |
| 17.4 | 5.1082 | 13.5 |
| 17.6 | 5.0375 | 6.7 |
| 18.9 | 4.7033 | 17.7 |
| 20.3 | 4.371 | 4 |
| 22.3 | 3.976 | 5.8 |
| 23.1 | 3.8469 | 6.6 |
| 24.5 | 3.6371 | 4.1 |
| 26.3 | 3.3865 | 8.3 |

TABLE 8-continued

XRPD Peak Positions for Form A of Compound 6

| Position [°2θ][1] | d-spacing [Å] | Intensity [%] |
|---|---|---|
| 26.7 | 3.3422 | 5.9 |
| 27.0 | 3.2941 | 2.6 |
| 29.9 | 2.9861 | 3.4 |

[1]In this and all subsequent tables, the position 2θ is within ± 0.2.

In some embodiments, Form A of compound 6 is characterized in that it has one or more peaks in its X-ray powder diffraction pattern selected from those at about 5.5, about 11.1 and about 18.9 degrees 2-theta. In some embodiments, Form A of compound 6 is characterized in that it has two or more peaks in its X-ray powder diffraction pattern selected from those at about 5.5, about 11.1 and about 18.9 degrees 2-theta. In some embodiments, Form A of compound 6 is characterized in that it has all three peaks in its X-ray powder diffraction pattern selected from those at about 5.5, about 11.1 and about 18.9 degrees 2-theta.

Figure 19:
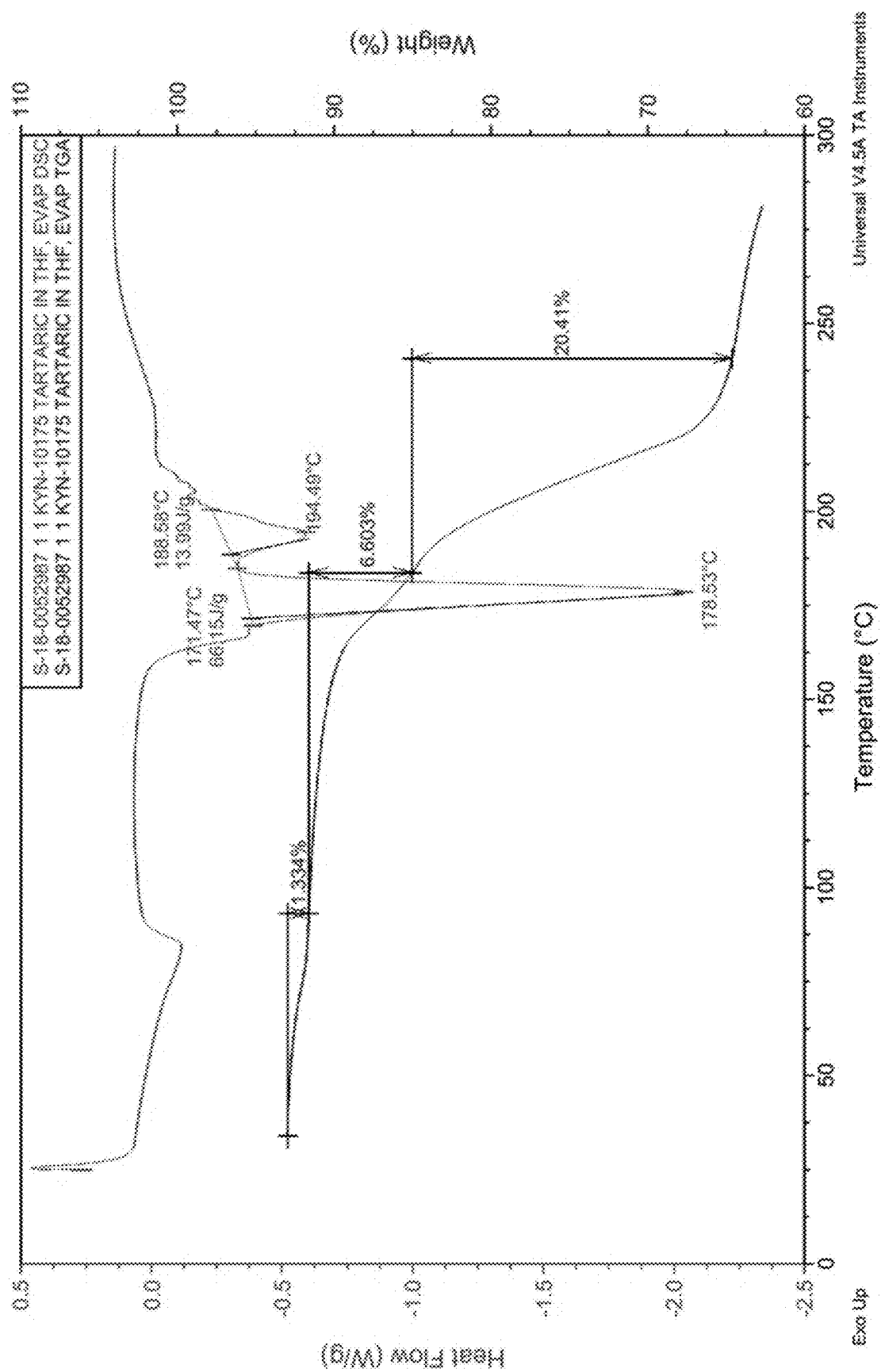
FIG. 19 depicts a TG/DTA trace of Compound 6, Form A.

In certain embodiments, the X-ray powder diffraction pattern is substantially similar to the XRPD provided in FIG. 19.

Methods for preparing Form A of compound 6 are described infra.

Form B of Compound 6

In some embodiments, Form B of compound 6 has at least 1, 2, 3, 4 or 5 spectral peak(s) selected from the peaks listed in Table 9 below.

TABLE 9

XRPD Peak Positions for Form B of Compound 6

| Position [°2θ][1] | d-spacing [Å] | Intensity [%] |
|---|---|---|
| 5.3 | 16.5046 | 1.7 |
| 6.2 | 14.2356 | 74.6 |
| 6.8 | 13.0713 | 100 |
| 7.2 | 12.183 | 2.4 |
| 8.6 | 10.2145 | 5 |
| 9.5 | 9.2819 | 0.6 |
| 10.7 | 8.2682 | 8.2 |
| 11.5 | 7.7192 | 4.5 |
| 12.4 | 7.1588 | 12.4 |
| 13.5 | 6.5301 | 24.8 |
| 14.6 | 6.0796 | 6.9 |
| 16.3 | 5.4162 | 2.1 |
| 17.1 | 5.1667 | 11.2 |
| 17.7 | 5.0058 | 3.2 |
| 18.7 | 4.7289 | 9.7 |
| 19.3 | 4.5962 | 3 |
| 20.6 | 4.3182 | 15.7 |
| 20.9 | 4.2371 | 11.5 |
| 21.8 | 4.0643 | 5.9 |

TABLE 9-continued

XRPD Peak Positions for Form B of Compound 6

| Position [°2θ][1] | d-spacing [Å] | Intensity [%] |
|---|---|---|
| 23.2 | 3.8387 | 0.8 |
| 24.3 | 3.6659 | 1.8 |
| 25.3 | 3.5112 | 1 |
| 26.1 | 3.4101 | 1.3 |

[1]In this and all subsequent tables, the position 2θ is within ± 0.2.

In some embodiments, Form B of compound 6 is characterized in that it has one or more peaks in its X-ray powder diffraction pattern selected from those at about 6.2, about 6.8 and about 13.5 degrees 2-theta. In some embodiments, Form B of compound 6 is characterized in that it has two or more peaks in its X-ray powder diffraction pattern selected from those at about 6.2, about 6.8 and about 13.5 degrees 2-theta. In some embodiments, Form B of compound 6 is characterized in that it has all three peaks in its X-ray powder diffraction pattern selected from those at about 6.2, about 6.8 and about 13.5 degrees 2-theta.

Figure 21:
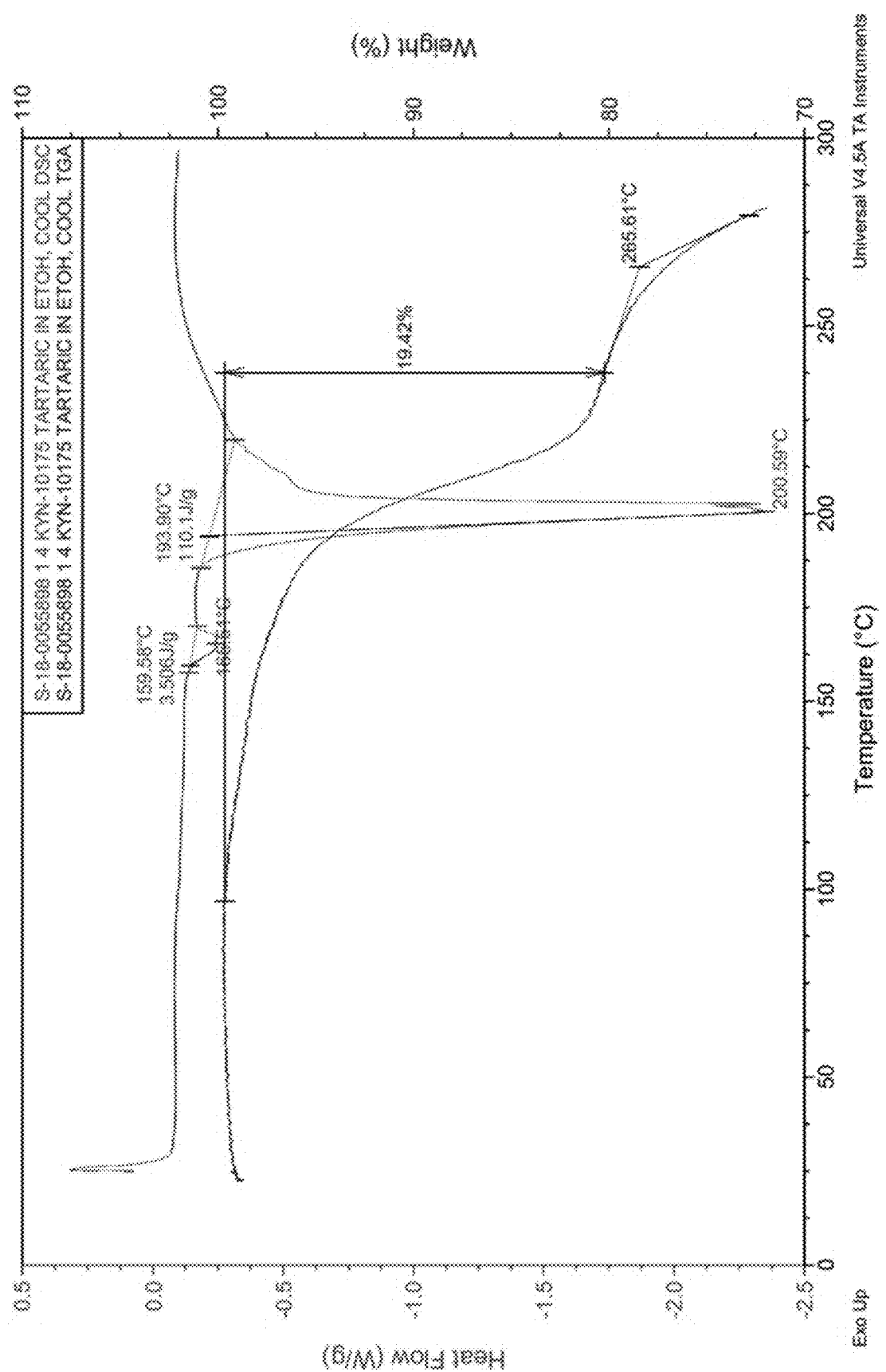
FIG. 21 depicts a TG/DTA trace of Compound 6, Form B.

In certain embodiments, the X-ray powder diffraction pattern is substantially similar to the XRPD provided in FIG. 21.

Methods for preparing Form B of compound 6 are described infra.

In some embodiments, the present invention provides compound 6:

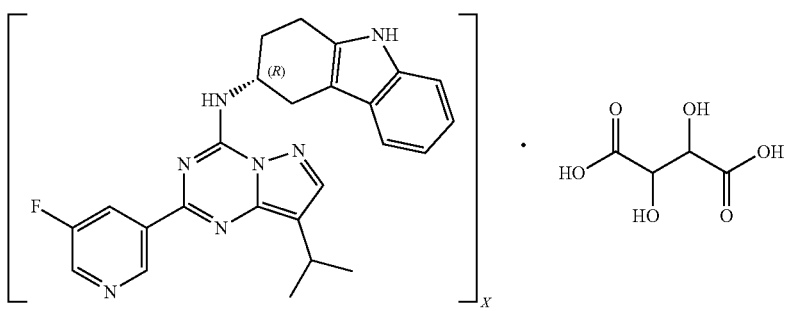

6 wherein about 1≤x≤about 2.

In some embodiments, the present invention provides compound 6, wherein said compound is crystalline.

In some embodiments, the present invention provides compound 6, wherein said compound is a crystalline solid substantially free of amorphous compound 6.

In some embodiments, the present invention provides compound 6, wherein said compound is substantially free of impurities.

In some embodiments, the present invention provides compound 6, wherein said compound has one or more peaks in its XRPD selected from those at about 5.5, about 11.1 and about 18.9 degrees 2-theta. In some such embodiments, the present invention provides compound 6, wherein said compound has at least two peaks in its XRPD selected from those at about 5.5, about 11.1 and about 18.9 degrees 2-theta. In some such embodiments, the present invention provides compound 6, wherein said compound is of Form A. In some embodiments, Form A of Compound 6 comprises compound A and tartaric acid in a ratio of about 1:1.

In some embodiments, the present invention provides compound 6, wherein said compound has an XRPD substantially similar to that depicted in FIG. 19.

In some embodiments, the present invention provides compound 6, wherein said compound has one or more peaks in its XRPD selected from those at about 6.2, about 6.8 and about 13.5 degrees 2-theta. In some such embodiments, the present invention provides compound 6, wherein said compound has at least two peaks in its XRPD selected from those at about 6.2, about 6.8 and about 13.5 degrees 2-theta. In some such embodiments, the present invention provides compound 6, wherein said compound is of Form B. In some embodiments, form B of Compound 6 comprises compound A and tartaric acid in a ratio of about 2:1.

In some embodiments, the present invention provides compound 6, wherein said compound has an XRPD substantially similar to that depicted in FIG. 21.

In some embodiments, the present invention provides a composition comprising compound 6 and a pharmaceutically acceptable carrier or excipient.

In some embodiments, the present invention provides a method of inhibiting AHR comprising administering to said patient compound 6 or composition thereof. In some embodiments, the present invention provides a method of inhibiting AHR in a patient comprising administering to said patient compound 6 or composition thereof. In some embodiments, the present invention provides a method of treating one or more disorders associated with activity of AHR comprising administering to said patient compound 6 or composition thereof.

In some embodiments, the present invention provides a method for treating an AHR-mediated disorder comprising the step of administering to a patient in need thereof compound 6 or composition thereof. In some embodiments, the AHR-mediated disorder is a proliferative disease such as cancer or an inflammatory disorder.

Compound 7 (Edisylate Salts of Compound A)

According to one embodiment, the present invention provides an edisylate salt of compound A, represented by compound 7:

may be amorphous, crystalline, or a mixture thereof. Exemplary solid forms are described in more detail below.

In some embodiments, the present invention provides compound 7 substantially free of impurities. As used herein, the term "substantially free of impurities" means that the compound contains no significant amount of extraneous matter. Such extraneous matter may include excess phosphoric acid, excess compound A, residual solvents, or any other impurities that may result from the preparation of, and/or isolation of, compound 7. In certain embodiments, at least about 95% by weight of compound 7 is present. In still other embodiments of the invention, at least about 99% by weight of compound 7 is present.

According to one embodiment, compound 7 is present in an amount of at least about 97, 97.5, 98.0, 98.5, 99, 99.5, 99.8 weight percent where the percentages are based on the total weight of the composition. According to another embodiment, compound 7 contains no more than about 3.0 area percent HPLC of total organic impurities and, in certain embodiments, no more than about 1.5 area percent HPLC total organic impurities relative to the total area of the HPLC chromatogram. In other embodiments, compound 7 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 7 is also meant to include all tautomeric forms of compound 7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 7 can exist in at least one distinct polymorphic form. In some embodiments, the present invention provides a polymorphic form of Compound 7 referred to herein as Form A. In some embodiments, Form

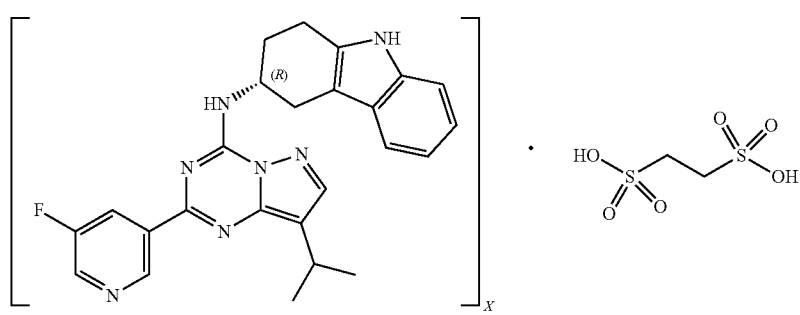

wherein about 1≤x≤about 2.

It will be appreciated by one of ordinary skill in the art that the ethanedisulfonic acid and compound A are ionically bonded to form compound 7. In some embodiments, compound A and ethanedisulfonic acid are in a ratio of about 1:1. In some embodiments, compound A and ethanedisulfonic acid are in a ratio of about 2:1. It is contemplated that compound 7 can exist in a variety of physical forms. For example, compound 7 can be in solution, suspension, or in solid form. In certain embodiments, compound 7 is in solid form. When compound 7 is in solid form, said compound A of Compound 7 comprises compound A and ethanedisulfonic acid in a ratio of about 2:1.

In certain embodiments, compound 7 is a crystalline solid. In other embodiments, compound 7 is a crystalline solid substantially free of amorphous compound 7. As used herein, the term "substantially free of amorphous compound 7" means that the compound contains no significant amount of amorphous compound 7. In certain embodiments, at least about 95% by weight of crystalline compound 7 is present. In still other embodiments of the invention, at least about 99% by weight of crystalline compound 7 is present.

In some embodiments, compound 7 is amorphous. In some embodiments, compound 7 is amorphous, and is substantially free of crystalline compound 7.

Form A of Compound 7

In some embodiments, Form A of compound 7 has at least 1, 2, 3, 4 or 5 spectral peak(s) selected from the peaks listed in Table 10 below.

TABLE 10

XRPD Peak Positions for Form A of Compound 7

| Position [°2θ][1] | d-spacing [Å] | Intensity [%] |
| --- | --- | --- |
| 6.6 | 13.4754 | 100 |
| 8.0 | 11.0262 | 0.7 |
| 10.4 | 8.5378 | 5 |
| 13.2 | 6.7031 | 7.3 |
| 16.0 | 5.5191 | 2.4 |
| 18.2 | 4.871 | 0.8 |
| 19.1 | 4.6422 | 1.8 |
| 19.3 | 4.5954 | 1.7 |
| 20.4 | 4.3516 | 0.7 |
| 22.4 | 3.9584 | 1.5 |
| 26.5 | 3.3549 | 0.6 |

[1]In this and all subsequent tables, the position 2θ is within ± 0.2.

In some embodiments, Form A of compound 7 is characterized in that it has one or more peaks in its X-ray powder diffraction pattern selected from those at about 6.6, about 10.4 and about 13.2 degrees 2-theta. In some embodiments, Form A of compound 7 is characterized in that it has two or more peaks in its X-ray powder diffraction pattern selected from those at about 6.6, about 10.4 and about 13.2 degrees 2-theta. In some embodiments, Form A of compound 7 is characterized in that it has all three peaks in its X-ray powder diffraction pattern selected from those at about 6.6, about 10.4 and about 13.2 degrees 2-theta.

Figure 23:
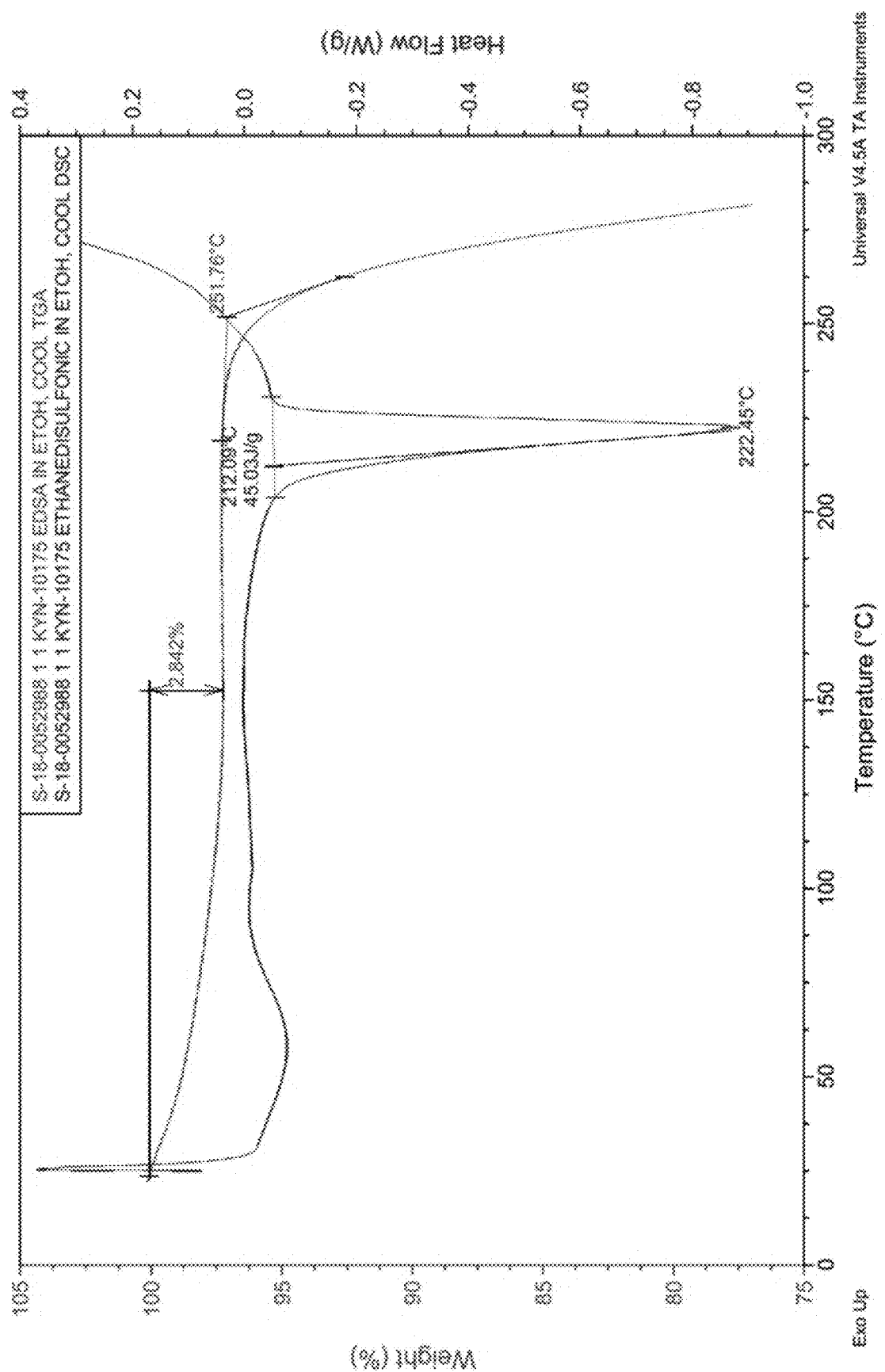
FIG. 23 depicts a TG/DTA trace of Compound 7, Form A.

In certain embodiments, the X-ray powder diffraction pattern is substantially similar to the XRPD provided in FIG. 23.

Methods for preparing Form A of compound 7 are described infra.

In some embodiments, the present invention provides compound 7:

In some embodiments, the present invention provides compound 7, wherein said compound has one or more peaks in its XRPD selected from those at about 6.6, about 10.4 and about 13.2 degrees 2-theta. In some such embodiments, the present invention provides compound 7, wherein said compound has at least two peaks in its XRPD selected from those at about 6.6, about 10.4 and about 13.2 degrees 2-theta. In some such embodiments, the present invention provides compound 7, wherein said compound is of Form A. In some embodiments, Form A of Compound 7 comprises compound A and ethanedisulfonic acid in a ratio of about 2:1.

In some embodiments, the present invention provides compound 7, wherein said compound has an XRPD substantially similar to that depicted in FIG. 23.

In some embodiments, the present invention provides a composition comprising compound 7 and a pharmaceutically acceptable carrier or excipient.

In some embodiments, the present invention provides a method of inhibiting AHR comprising administering to said patient compound 7 or composition thereof. In some embodiments, the present invention provides a method of inhibiting AHR in a patient comprising administering to said patient compound 7 or composition thereof. In some embodiments, the present invention provides a method of treating one or more disorders associated with activity of AHR comprising administering to said patient compound 7 or composition thereof.

In some embodiments, the present invention provides a method for treating an AHR-mediated disorder comprising the step of administering to a patient in need thereof compound 7 or composition thereof. In some embodiments, the AHR-mediated disorder is a proliferative disease such as cancer or an inflammatory disorder.

In some embodiments, the present invention provides a compound selected from: compound A, Form B; compound A, Form C; compound 1, Form A; compound 1, Form B; compound 2, Form A; compound 3, Form A; compound 3, Form B; compound 4, Form A; compound 5, Form A; compound 6, Form A; compound 6, Form B; and compound 7, Form A. In some such embodiments, the present invention

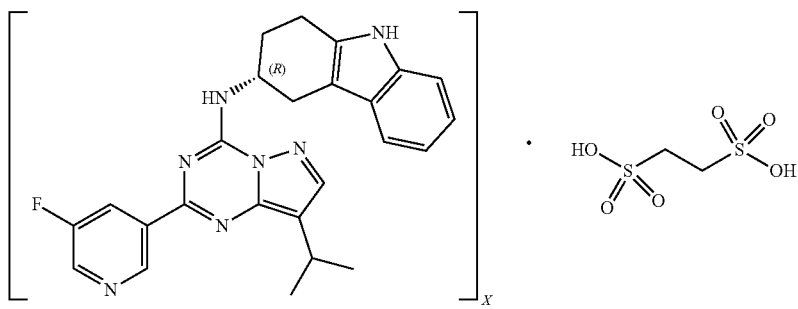

wherein about 1≤x≤about 2.

In some embodiments, the present invention provides compound 7, wherein said compound is crystalline.

In some embodiments, the present invention provides compound 7, wherein said compound is a crystalline solid substantially free of amorphous compound 7.

In some embodiments, the present invention provides compound 7, wherein said compound is substantially free of impurities.

provides a composition comprising one of the above compound forms and a pharmaceutically acceptable carrier or excipient.

In some such embodiments, the present invention provides a method of inhibiting AHR comprising administering to said patient a compound of the present invention or composition thereof. In some such embodiments, the present invention provides a method of inhibiting AHR in a patient comprising administering to said patient a compound of the present invention or composition thereof. In some such embodiments, the present invention provides a method of treating one or more disorders associated with activity of AHR comprising administering to said patient a compound of the present invention or composition thereof.

In some such embodiments, the present invention provides a method for treating an AHR-mediated disorder comprising the step of administering to a patient in need thereof a compound of the present invention or composition thereof. In some such embodiments, the AHR-mediated disorder is a proliferative disease such as cancer or an inflammatory disorder.

General Methods of Providing a Salt Compound

Compound A is prepared according to the methods described in detail in the '411 publication, the entirety of which is hereby incorporated herein by reference. Salt compounds of general formula X, which formula encompasses, inter alia, salt compounds 1 through 7, and/or particular forms thereof, are prepared from compound A, according to the general Scheme below.

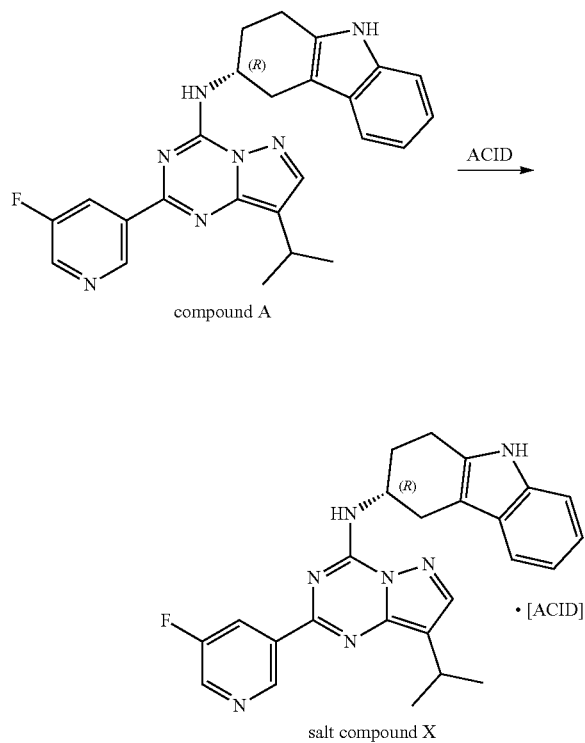

compound A

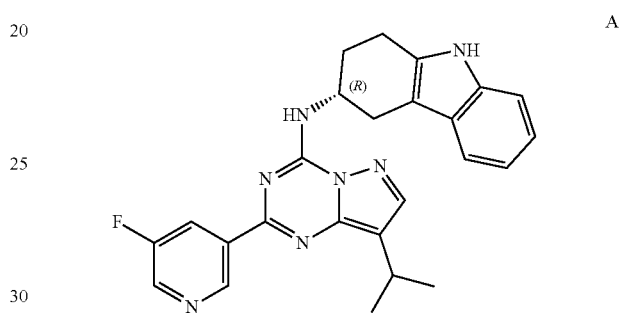

salt compound X

For instance, each of compounds 1 through 7, and forms thereof, are prepared from compound A by combining compound A with an appropriate acid to form a salt of that acid. Thus, another aspect of the present invention provides a method for preparing compounds 1 through 7, and forms thereof.

As described generally above, in some embodiments, the present invention provides a method for preparing a salt compound of the general formula X:

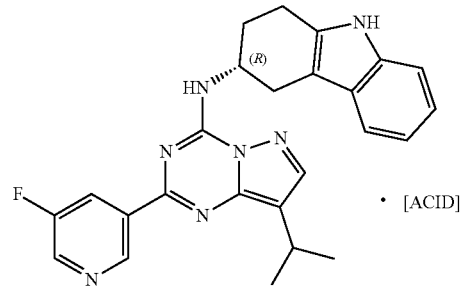

salt compound X comprising steps of:
combining compound A:

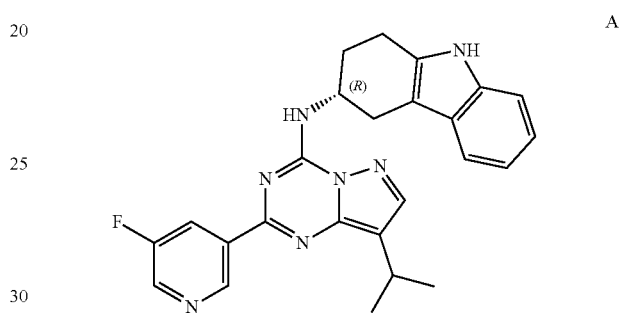

A with a suitable acid and optionally a suitable solvent under conditions suitable for forming a salt compound of general formula X.

In some embodiments, a suitable acid is ethanesulfonic acid. In some embodiments, the present invention provides a method of making a esylate salt of compound A. In certain embodiments, the esylate salt of compound A is compound 1. In certain embodiments, the esylate salt of compound A is Form A of compound 1. In certain embodiments, the esylate salt of compound A is Form B of compound 1.

In some embodiments, a suitable acid is maleic acid. In some embodiments, the present invention provides a method of making a maleate salt of compound A. In certain embodiments, the maleate salt of compound A is compound 2. In certain embodiments, the maleate salt of compound A is Form A of compound 2.

In some embodiments, a suitable acid is methanesulfonic acid. In some embodiments, the present invention provides a method of making a mesylate salt of compound A. In certain embodiments, the mesylate salt of compound A is compound 3. In certain embodiments, the mesylate salt of compound A is Form A of compound 3. In certain embodiments, the mesylate salt of compound A is Form B of compound 3.

In some embodiments, a suitable acid is naphthalenesulfonic acid. In some embodiments, the present invention provides a method of making a napsylate salt of compound A. In certain embodiments, the napsylate salt of compound A is compound 4. In certain embodiments, the napsylate salt of compound A is Form A of compound 4.

In some embodiments, a suitable acid is oxalic acid. In some embodiments, the present invention provides a method of making an oxalate salt of compound A. In certain embodiments, the oxalate salt of compound A is compound 5. In certain embodiments, the oxalate salt of compound A is Form A of compound 5.

In some embodiments, a suitable acid is tartaric acid. In some embodiments, the present invention provides a method of making a tartrate salt of compound A. In certain embodiments, the tartrate salt of compound A is compound 6. In certain embodiments, the tartrate salt of compound A is Form A of compound 6. In certain embodiments, the tartrate salt of compound A is Form B of compound 6.

In some embodiments, a suitable acid is ethanedisulfonic acid. In some embodiments, the present invention provides a method of making an edisylate salt of compound A. In certain embodiments, the edisylate salt of compound A is compound 7. In certain embodiments, the edisylate salt of compound A is Form A of compound 7.

A suitable solvent may be any solvent system (e.g., one solvent or a mixture of solvents) in which compound A and/or an acid are soluble, or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

In some embodiments, the present invention provides a method for preparing a salt compound of the general formula X, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a salt compound of the general formula X comprises one or more steps of heating or cooling a preparation.

In some embodiments, a method for preparing a salt compound of the general formula X comprises one or more steps of agitating or stirring a preparation.

In some embodiments, a method for preparing a salt compound of the general formula X comprises a step of adding a suitable acid to a solution or slurry of compound A.

In some embodiments, a method for preparing a salt compound of the general formula X comprises a step of heating.

In certain embodiments, a salt compound of formula X precipitates from the mixture. In another embodiment, a salt compound of formula X crystallizes from the mixture. In other embodiments, a salt compound of formula X crystallizes from solution following seeding of the solution (i.e., adding crystals of a salt compound of formula X to the solution).

A salt compound of formula X can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a salt compound of formula X is optionally isolated. It will be appreciated that a salt compound of formula X may be isolated by any suitable physical means known to one of ordinary skill in the art. In certain embodiments, precipitated solid salt compound of formula X is separated from the supernatant by filtration. In other embodiments, precipitated solid salt compound of formula X is separated from the supernatant by decanting the supernatant.

In certain embodiments, a salt compound of formula X is separated from the supernatant by filtration.

In certain embodiments, an isolated salt compound of formula X is dried in air. In other embodiments, isolated salt compound of formula X is dried under reduced pressure, optionally at elevated temperature.

Uses, Formulation and Administration and Pharmaceutically acceptable compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit AHR, in a biological sample or in a patient. In certain embodiments, the amount of compound in compositions of this invention is such that is effective to measurably inhibit AHR, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The activity of a compound utilized in this invention as an inhibitor of AHR may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses AHR. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of AHR are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with AHR.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses and Methods of Treatment

According to one embodiment, the invention relates to a method of inhibiting AHR in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting AHR in a patient comprising the step of administering to said patient a compound of the present invention, or a composition comprising said compound.

Provided compounds are inhibitors of AHR and are therefore useful for treating one or more disorders associated with activity of AHR. Thus, in certain embodiments, the present invention provides a method for treating an AHR-mediated disorder comprising the step of administering to a patient in need thereof a compound of the present invention, or pharmaceutically acceptable composition thereof. In some embodiments, the present invention provides a use of a compound or a solid form of the present invention, or a pharmaceutically acceptable composition thereof, for the treatment of a disease, disorder, or condition as described herein.

As used herein, the terms "AHR-mediated" disorders, diseases, and/or conditions as used herein means any disease or other deleterious condition in which AHR, or a mutant thereof, are known to play a role. Accordingly, another embodiment of the present invention relates to treating or lessening the severity of one or more diseases in which AHR, or a mutant thereof, are known to play a role.

AHR mediated disorders are well established in the art. The nexus between AHR and AHR mediated disorders diseases and/or conditions as recited herein is well established in the relevant arts. For example, see: Uyttenhove et al., "Evidence for a tumoral immune resistance mechanism based on tryptophan degradation by indoleamine 2,3-dioxygenase" *Nature Medicine,* 2003 vol. 9(10), 1038; Murray et al., "AH RECEPTOR LIGANDS IN CANCER: FRIEND AND FOE" *Nat. Rev. Cancer* December 2014, vol. 14(12), pages 801-814; Moon et al., "Targeting the indoleamine 2,3-dioxygenase pathway in cancer" *J. ImmunoTherapy of Cancer,* 2015 vol 3, page 51; Ishida et al., "Activation of aryl hydrocarbon receptor promotes invasion of clear cell renal cell carcinoma and is associated with poor prognosis and cigarette smoke" *Int. J. Cancer July* 2015 vol. 15, no. 137(2), pages 299-310; Ishida et al., "Activation of the aryl hydrocarbon receptor pathway enhances cancer cell invasion by upregulating the MMP expression and is associated with poor prognosis in upper urinary tract urothelial cancer" *Carcinogenesis* February 2010 vol. 31(2), pages 287-295. Su et al., "Prognostic value of nuclear translocation of aryl hydrocarbon receptor for non-small cell lung cancer" *Anticancer Res.* September 2013, vol. 33(9), pages 3953-3961; Peng et al., "Aryl hydrocarbon receptor pathway activation enhances gastric cancer cell invasiveness likely through a c-Jun-dependent induction of matrix metalloproteinase-9" *BMC Cell Biol.* April 2009 vol. 16; pages 10-27; Jin et al., "Aryl Hydrocarbon Receptor Activation Reduces Dendritic Cell Function during Influenza Virus Infection" Toxicol Sci. August 2010, vol. 116(2), pages 514-522; Head et al., "The aryl hydrocarbon receptor is a modulator of anti-viral immunity" *Biochem. Pharmacol.* February 2009 vol. 15; no. 77(4), pages 642-53; Jin et al., "New insights into the role of the aryl hydrocarbon receptor in the function of $CD11c^+$ cells during respiratory viral infection" *Eur. J. Immunol.* June 2014, vol. 44(6), pages 1685-98; Nguyen et al., "Aryl hydrocarbon receptor and kynurenine: recent advances in autoimmune disease research" *Front Immunol.* October 2014, vol. 29, no. 5, page 551; Esser et al., "The aryl hydrocarbon receptor in immunity" *Trends in Immunology,* Vol. 30, No. 9.

In some embodiments, the present invention provides a method for treating one or more disorders, diseases, and/or conditions wherein the disorder, disease, or condition is a proliferative disease such as cancer, an inflammatory disorder, or a viral infection.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL).

Compounds of the current invention are useful in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, Waldenström's macroglobulinemia, a mammary carcinoma, follicular carcinoma, undifferentiated carcinoma, papillary carcinoma, seminoma, melanoma, an MYD88-driven disorder, DLBCL, ABC DLBCL, an IL-1-driven disorder, Smoldering of indolent multiple myeloma, or a leukemia.

Cancer includes, in some embodiments, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (WA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CIVIL), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrom Macroglobulinemia, or Wilms Tumor.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Graves' disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, dermatomyositis, polymyositis, inclusion body myositis, myasthenia gravis, thyroiditis, Addison's disease, lichen planus, Type 1 diabetes, or Type 2 diabetes.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin-Associated Periodic Syndromes (CAPS), or osteoarthritis.

In some embodiments, the inflammatory disease which can be treated according to the methods of this invention is selected from a TH17-mediated disease. In some embodiments, the TH17-mediated disease is selected from Systemic lupus erythematosus, Multiple sclerosis, inflammatory bowel disease including Crohn's or ulcerative colitis.

In some embodiments, the inflammatory disease which can be treated according to the methods of this invention is selected from Sjogren's syndrome allergic disorders, osteoarthritis. Conditions of the eye such as ocular allergy, conjunctivitis, keratoconjunctivitis sicca, and vernal conjunctivitis, diseases affecting the nose including allergic rhinitis.

In some embodiments, the inflammatory disease which can be treated according to the methods of this invention is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus *foliaceus*, paraneoplastic pemphigus, epidermolysis bullosa acquisita, and other inflammatory or allergic conditions of the skin.

In certain embodiments, a provided compound is useful for treating a viral infection, disease, or condition. In some embodiments, the present invention provides a method of treating a viral disease selected from retroviral diseases, such as, HIV-1, HIV-2, human T-cell leukemia virus-I (HTLV-I), HTLV-II, HTLV-III, simian immunodeficiency virus (SIV), lymphadenopathy-associated virus (LAV-2), simian T-lymphotrophic virus-I (STLV-I), STLV-II, STLV-III, simian B-lymphotrophic (SBL) virus, Gibbon ape leukemia virus (GALV), bovine leukemia virus (BLV), equine infectious anemia virus (EIAV), feline leukemia virus (FELV), murine leukemia virus (MuLV), avian leukosis virus (ALV); other virus infections such as hepadnaviridae (Hepatitis B); herpesviridae (Herpes simplex I, Herpes simplex II, Varicella-Zoster, Epstein-Barr virus and cytomegalovirus); parvoviridae (human parvovirus B-19); papovaviridae (human papilloma virus types 1 to 60, JC and BK viruses); pox viruses (variola major, variola minor, vaccinia, monkey pox, cowpox, paravaccinia or milker's node virus, parapox or ORF virus, molluscum contagiosum) and cancers, lymphomas and other leukemias.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa Irinotecan, Isotretinoin, Ixabepilone, Ixempra™, Kidrolase Lanacort Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred Lomustine, L-PAM, L-Sarcolysin, Lupron Lupron Depot®, Matulane Maxidex, Mechlorethamine, Mechlorethamine Hydrochloride, Medralone Medrol Megace Megestrol, Megestrol Acetate, Melphalan, Mercaptopurine, Mesna, Mesnex™, Methotrexate, Methotrexate Sodium, Methylprednisolone, Meticorten Mitomycin, Mitomycin-C, Mitoxantrone, M-Prednisol MTC, MTX, Mustargen Mustine, Mutamycin Myleran Mylocel™, Mylotarg Navelbine Nelarabine, Neosar Neulasta™, Neumega Neupogen Nexavar Nilandron Nilotinib, Nilutamide, Nipent®, Nitrogen Mustard, Novaldex Novantrone Nplate, Octreotide, Octreotide acetate, Ofatumumab, Oncospar Oncovin Ontak Onxal™, Oprelvekin, Orapred Orasone Oxaliplatin, Paclitaxel, Paclitaxel Proteinbound, Pamidronate, Panitumumab, Panretin Paraplatin Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol Platinol-AQ Prednisolone, Prednisone, Prelone Procarbazine, PROCRIT Proleukin Prolifeprospan 20 with Carmustine Implant, Purinethol Raloxifene, Revlimid Rheumatrex Rituxan Rituximab, Roferon-A® (Interferon Alfa-2a), Romiplostim, Rubex Rubidomycin hydrochloride, Sandostatin Sandostatin LAR Sargramostim, Solu-Cortef Solu-Medrol Sorafenib, SPRYCEL™, STI-571, Streptozocin, SU11248, Sunitinib, Sutent Tamoxifen, Tarceva Targretin Tasigna Taxol Taxotere Temodar Temozolomide, Temsirolimus, Teniposide, TESPA, Thalidomide, Thalomid TheraCys Thioguanine, Thioguanine Tabloid®, Thiophosphoamide, Thioplex Thiotepa, TICE®, Toposar Topotecan, Toremifene, Torisel Tositumomab, Trastuzumab, Treanda Tretinoin, Trexall™, Trisenox TSPA, TYKERB®, VCR, Vectibix™, Velban Velcade VePesid Vesanoid Viadur™, Vidaza Vinblastine, Vinblastine Sulfate, Vincasar Pfs Vincristine, Vinorelbine, Vinorelbine tartrate, VLB, V1\4-26, Vorinostat, Votrient, VP-16, Vumon Xeloda Zanosar Zevalin™, Zinecard Zoladex Zoledronic acid, Zolinza, Zometa®, or combinations of any of the above.

In certain embodiments, an immuno-oncology agent can be administered with a compound as described herein for treatment of a proliferative disorder as described herein. As used herein, the term "an immuno-oncology agent" refers to an agent which is effective to enhance, stimulate, and/or up-regulate immune responses in a subject. In some embodiments, the administration of an immuno-oncology agent with a compound as described herein has a synergic effect in treating cancer.

In some embodiments, a compound as described herein is sequentially administered prior to administration of an immuno-oncology agent. In some embodiments, a compound as described herein is administered concurrently with an immuno-oncology agent. In some embodiments, a compound as described herein is sequentially administered after administration of an immuno-oncology agent.

In some embodiments, a compound as described herein may be co-formulated with an immuno-oncology agent.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/ Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound as described herein, and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an IDO antagonist. In some embodiments, an IDO antagonist is INCB-024360 (WO2006/122150, WO07/75598, WO08/36653, WO08/36642), indoximod, or NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, mTOR inhibitors, CPT1 inhibitors, AMPK activators, PCSK9 inhibitors, SREBP site 1 protease inhibitors, HMG CoA-reductase inhibitors, antiemetics (e.g. 5-HT3 receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

In another embodiment, the present invention provides a method of treating an inflammatory disease, disorder or condition by administering to a patient in need thereof a compound of the present invention and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphami de (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In some embodiments, a provided compound is administered in combination with an antiviral agent, including, e.g., acyclovir, pencyclovir, cidofovir, idoxuridine, zidovudine, ribavarin, amantadine, foscarnet, didanosine, acyclovir, ganciclovir, cidofovir, zalcitabine, rimantadine, calacyclovir, famiciclovir, abacavir, didanosine, emtricitabine, lamivudine, stavudine, tenofovir, zalcitabine, zidovudine, zidovudine-lamivudine, TRIZIVIR (zidovudine, lamivudine, abacavir), EPZICOM (aba-cavir-lamivudine), TRUVADA (tenofovir-emtricitabine), efavirenz, nevirapine, and delavirdine, amprenavir, atazanavir, fosamprenavir, indinavir, lopinavir-ritonavir, nelfinavir, ritonavir, saquinavir, and tipranavir. In some embodiments, the antiviral agent is anti-influenza agent including, e.g., rimantadine, amantadine, oseltamivir, and zanamivir.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the present invention, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the present invention and one or more additional therapeutic agents. The therapeutic agent may be administered together with a compound of the present invention, or may be administered prior to or following administration of a compound of the present invention. Suitable therapeutic agents are described in further detail below. In certain embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a medicament comprising at least one compound of the present invention or a pharmaceutically acceptable salt thereof and a pharmaceutically acceptable carrier.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures
X-ray Powder Diffraction (XRPD)

An X-ray diffraction system is configured for reflection Bragg-Brentano geometry using a line source X-ray beam. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, an X-ray diffraction system is operated to give peak widths of 0.1° 2θ or less. The axial divergence of the X-ray beam is controlled by 5.0-degree Soller slits in both the incident and diffracted beam paths.

Powder samples are prepared in a low background Si holder using light manual pressure to keep the sample surfaces flat and level with the reference surface of the sample holder. Each sample is analyzed from 2 to 40° 2θ using a continuous scan of 6° 2θ per minute with an effective step size of 0.02° 2θ.

Differential Scanning calorimetry (DSC)

DSC analyses are carried out using a TA instrument. The instrument temperature calibration is performed using indium. The DSC cell is kept under a nitrogen purge of ~50 mL per minute during each analysis. The sample is placed in a standard, crimped, aluminum pan and is heated from 25° C. to 350° C. at a rate of 10° C. per minute.

Thermogravimetric (TG) Analysis

The TG analysis is carried out using a TA instrument. The instrument balance is calibrated using class M weights and the temperature calibration is performed using alumel. The nitrogen purge is ~40 mL per minute at the balance and ~60 mL per minute at the furnace. Each sample is placed into a pre-tared platinum pan and heated from 20° C. to 350° C. at a rate of 10° C. per minute.

Nuclear Magnetic Resonance (NMR) Spectroscopy

Samples are prepared by dissolving material in a solvent. The solutions are filtered and placed into individual 5-mm NMR tubes for subsequent spectral acquisition.

Primary Salt Screening

Salt screening experiments were conducted using twelve (12) acid salt formers, with a variety of crystallization techniques (cooling, slurrying, evaporation, and vapor diffusion) being employed. The experimental details for each salt forming attempt are described in Table 11.

TABLE 11

| Salt Screening Experiments | | |
|---|---|---|
| Salt Former (X:Y)[1] | Crystallization Technique | Results |
| Aspartic acid (1:1) | Slurry in 1:1 acetone:water at RT. | Compound A Form B |
| Ethanesulfonic acid (1:1) | Slurry in 1:1 THF: water atRT. | Compound A Form C |
| | Dissolve in 9:1 acetone:water at 50° C. Slow cool to RT. | 1:1 Compound 1 Form A with no residual solvent by NMR |
| Ethanedisulfonic acid | Slurry in EtOH at 65° C., added EtOAc did not dissolve. Slow cool to RT. | 1:0.64 Compound 7 Form A with 0.11 equiv. EtOAc and 0.33 equiv. EtOH |
| (1:1) | Slurry in EtOH at 65° C., added EtOAc did not dissolve. Slow cool to RT. | 1:0.75 Compound 7 Form A with no EtOH by NMR |

TABLE 11-continued

Salt Screening Experiments

| Salt Former (X:Y)[1] | Crystallization Technique | Results |
|---|---|---|
| 1M Hydrochloric acid (1:1) | Dissolve in THF at RT. Vapor diffusion in heptane. | Residual oil formed. |
|  | Slurry in EtOH at 65° C. Slow cool toRT. | Free Base Form B |
|  | Slurry in acetone at RT. | Free Base Form B + peaks |
| Maleic acid (1:1) | Dissolve in acetone at RT. Vapor diffusion in heptane. | 1:0.6 Compound 2 Form A with 0.02 equiv. acetone by NMR |
|  | Dissolve in THF at RT. Vapor diffusion in heptane. | Not enough solids to collect. |
|  | Dissolve in acetone at 50° C. Slow cool to RT. Add equal volume of heptane and stir at 5° C. Partially evaporate to obtain solids. | 1:0.58 Compound 2 Form A with 0.025 equiv. acetone and 0.72 equiv. heptane by NMR |
| Methanesulfonic acid (1:1) | Slurry in EtOH at RT. | 1:1 Compound 3 Form A with 0.9 equiv. EtOH by NMR |
|  | Slurry in EtOH at RT. Vacuum dry. | 1:1 Compound 3 Form A + Form B with no EtOH by NMR |
| Naphthalenesulfonic Acid (1:1) | Dissolve in EtOH at 65° C. Slow cool to RT. | 1:1 Compound 4 Form A with 0.05 equiv. EtOH by NMR |
| Oxalic Acid (1:1) | Dissolve in acetone at 50° C. Slow cool to RT. | Compound 5 Form A Cannot confirm salt formation by NMR |
| 1M Phosphoric acid (1:1) | Slurry in EtOH at RT. | Compound A Form B |
| 1M Phosphoric acid (1:2) | Stir in water at RT. Solids remained floating. | Solids were not collected. |
| 1M Sulfuric acid (1:1) | Slurry in IPA at RT. | Compound A Form B |
|  | Slurry in EtOH at RT. | Compound A Form B |
|  | Dissolve in 9:1 acetone:water at 50° C. Slow cool to RT. | Compound A Form B |
| Tartaric acid (1:1) | Slurry in 9:1 acetone:water at RT. | Compound A Form B |
|  | Dissolve in THF at RT. Filter and fast evaporation. | 1:1 Compound 6 Form A with 0.48 equiv. THF |
|  | Dissolve in EtOH + EtOAc at 65° C. Slow cool to RT. | Compound A Form B |
| Tartaric acid (1:4) | Dissolve in EtOH + EtOAc at 65° C. Slow cool to RT. | 1:0.66 Compound 6 Form B with 0.12 equiv. EtOAc by NMR |
| Toluenesulfonic acid (1:1) | Slurry in MeOH at RT. | Compound A Form B |
|  | Dissolve in 9:1 acetone:water at 50° C. Slow cool to RT. | No solids formed. |

Secondary Salt Screening

Compound 1, Form A, Compound 2, Form A, Compound 3, Form B, and Compound 4, Form A were scaled up and the experimental details are described below in Table 12.

TABLE 12

Secondary Salt Screening Experiments

| Salt Former (X:Y)[1] | Crystallization Technique | Results |
|---|---|---|
| Ethanesulfonic Acid (1:1) | Slurry 500 mg free base in 15 mL 9:1 acetone:water at 50° C. Add 93 μL acid at 50° C. Slowly cool to RT while stirring then refrigerate at 5° C. overnight. | 1:1 Compound 1 Form B with no residual acetone |
| Methanesulfonic Acid (1:1) | Slurry 500 mg free base in 15 mL EtOH at RT. Add 74 pL acid and continue stirring overnight. Vacuum dry for 3 days at ~40° C. | 1:1 Compound 3 Form B with no residual EtOH |
| Maleic Acid (1:1) | Dissolve 500 mg free base and 132 mg acid in 7 mL acetone at 50° C. Slowly cool to RT then add equal volume of heptane (7 mL) and refrigerate at 5° C. overnight. Allow slurry to partially evaporate for 2 hours. | 1:0.54 Compound 2 Form A with 0.02 equiv. acetone |
| Naphthalenesulfonic Acid (1:1) | Slurry 500 mg free base and 236 mg acid in 10 mL EtOH at 65° C. Slowly cool to RT then refrigerate at 5° C. overnight. | 1:1 Compound 4 Form A with 0.07 equiv. EtOH |

Example A—General Preparation of Compound A

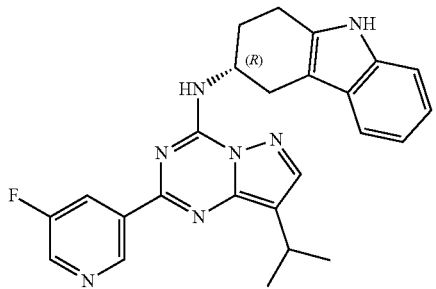

Compound A

The title compound was prepared according to the steps and intermediates (e.g., Scheme 1) described below and in the '411 publication, the entirety of which is incorporated herein by reference.

Scheme 1 - Synthesis of Compound A

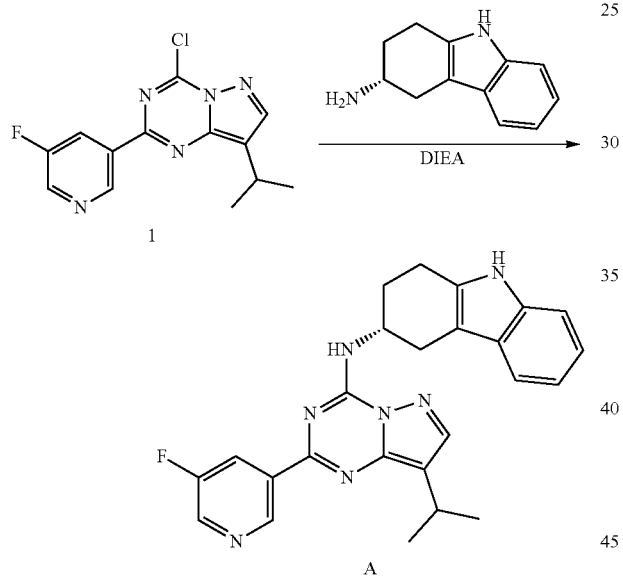

Step 1: (3R)—N-[2-(5-Fluoro-3-pyridyl)-8-isopropyl-pyrazolo[1,5-a][1,3,5]triazin-4-yl]-2,3,4,9-tetrahydro-1H-carbazol-3-amine (compound A)

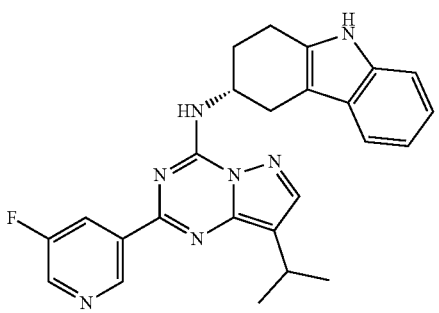 [SMILES: CC(C)c1cnn2c(N[C@@H]3CCc4[nH]c5ccccc5c4C3)nc(-c3cncc(F)c3)nc12]

A mixture of 4-chloro-2-(5-fluoro-3-pyridyl)-8-isopropyl-pyrazolo[1,5-a][1,3,5] triazine (60.00 mg, 205.68 μmol, 1 eq), (3R)-2,3,4,9-tetrahydro-1H-carbazol-3-amine (42.14 mg, 226.25 μmol, 1.1 eq), DIEA (79.75 mg, 617.05 μmol, 107.48 μL, 3 eq) in i-PrOH (4 mL) was degassed and purged with N2 for 3 times. The mixture was stirred at 55° C. for 3 h under N2 atmosphere. The reaction mixture was concentrated under reduced pressure to give a residue which was purified by preparative HPLC (column: Phenomenex Gemini 150*25 mm*10 um; mobile phase: [water (0.05% HCl)-ACN]; B %: 70%-100%, 10 min), followed by lyophilization to yield (3R)—N-[2-(5-fluoro-3-pyridyl)-8-isopropyl-pyrazolo[1,5-a][1,3,5]triazin-4-yl]-2,3,4,9-tetrahydro-1H-carbazol-3-amine (42.07 mg, 75.45 μmol, 36.7% yield, 98.8% purity, 3HCl) as a yellow solid. $^1$H NMR (400 MHz, CD$_3$OD) δ ppm 9.46 (s, 1H), 8.81 (d, J=9.3 Hz, 1H), 8.76 (s, 1H), 8.12-7.92 (m, 1H), 7.37 (d, J=7.7 Hz, 1H), 7.27 (d, J=7.9 Hz, 1H), 7.08-7.00 (m, 1H), 6.99-6.90 (m, 1H), 3.34 (s, 1H), 3.31-3.25 (m, 2H), 3.18-2.79 (m, 3H), 2.44-2.21 (m, 2H), 1.42 (d, J=7.1 Hz, 6H); ES-LCMS m/z 442.2 [M+H]$^+$.

Example 1—Preparation of Free Base Forms A, B and C of Compound A

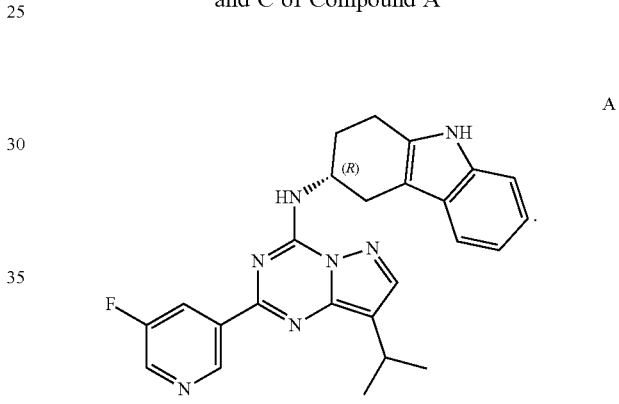

A

Form B of Compound A

Form B of compound A was prepared as described above.
Table B, supra, is reproduced below and sets forth the X-ray diffraction peaks observed for Form B of compound A.

TABLE B

XRPD Peak Positions for Form B of Compound A

| Position [°2θ]$^1$ | d-spacing [Å] | Intensity [%] |
|---|---|---|
| 8.5 | 10.3405 | 0.8 |
| 9.2 | 9.5896 | 11 |
| 9.5 | 9.3466 | 100 |
| 9.8 | 8.9763 | 26.3 |
| 11.3 | 7.7944 | 4 |
| 12.8 | 6.907 | 9.6 |
| 13.7 | 6.4438 | 3.9 |
| 14.2 | 6.2284 | 10 |
| 14.7 | 6.0202 | 27.4 |
| 15.4 | 5.7663 | 3.5 |
| 16.8 | 5.2862 | 13.9 |
| 17.5 | 5.0495 | 7.6 |
| 17.9 | 4.9378 | 1 |
| 18.5 | 4.8002 | 0.7 |
| 19.0 | 4.6705 | 1.3 |
| 19.2 | 4.6159 | 2 |
| 19.8 | 4.485 | 9.8 |
| 20.1 | 4.4138 | 14.2 |

TABLE B-continued

XRPD Peak Positions for Form B of Compound A

| Position [°2θ][1] | d-spacing [Å] | Intensity [%] |
|---|---|---|
| 20.9 | 4.2497 | 1.1 |
| 21.6 | 4.1169 | 2.3 |
| 21.8 | 4.073 | 1.4 |
| 22.5 | 3.9481 | 44 |
| 23.6 | 3.7662 | 1.5 |
| 24.2 | 3.6729 | 5.8 |
| 24.6 | 3.6111 | 1.5 |
| 25.7 | 3.4637 | 6.2 |
| 26.0 | 3.4299 | 3.1 |
| 27.3 | 3.2589 | 1.8 |
| 27.7 | 3.2135 | 3.4 |
| 28.1 | 3.1726 | 1.4 |
| 28.6 | 3.1145 | 1.6 |
| 29.1 | 3.0612 | 1 |
| 29.7 | 3.0045 | 4.8 |
| 31.5 | 2.8379 | 3.4 |

[1]In this and all subsequent tables, the position 2θ is within ± 0.2.

FIG. 1 depicts an XRPD pattern of Form B of compound A.

Figure 2:
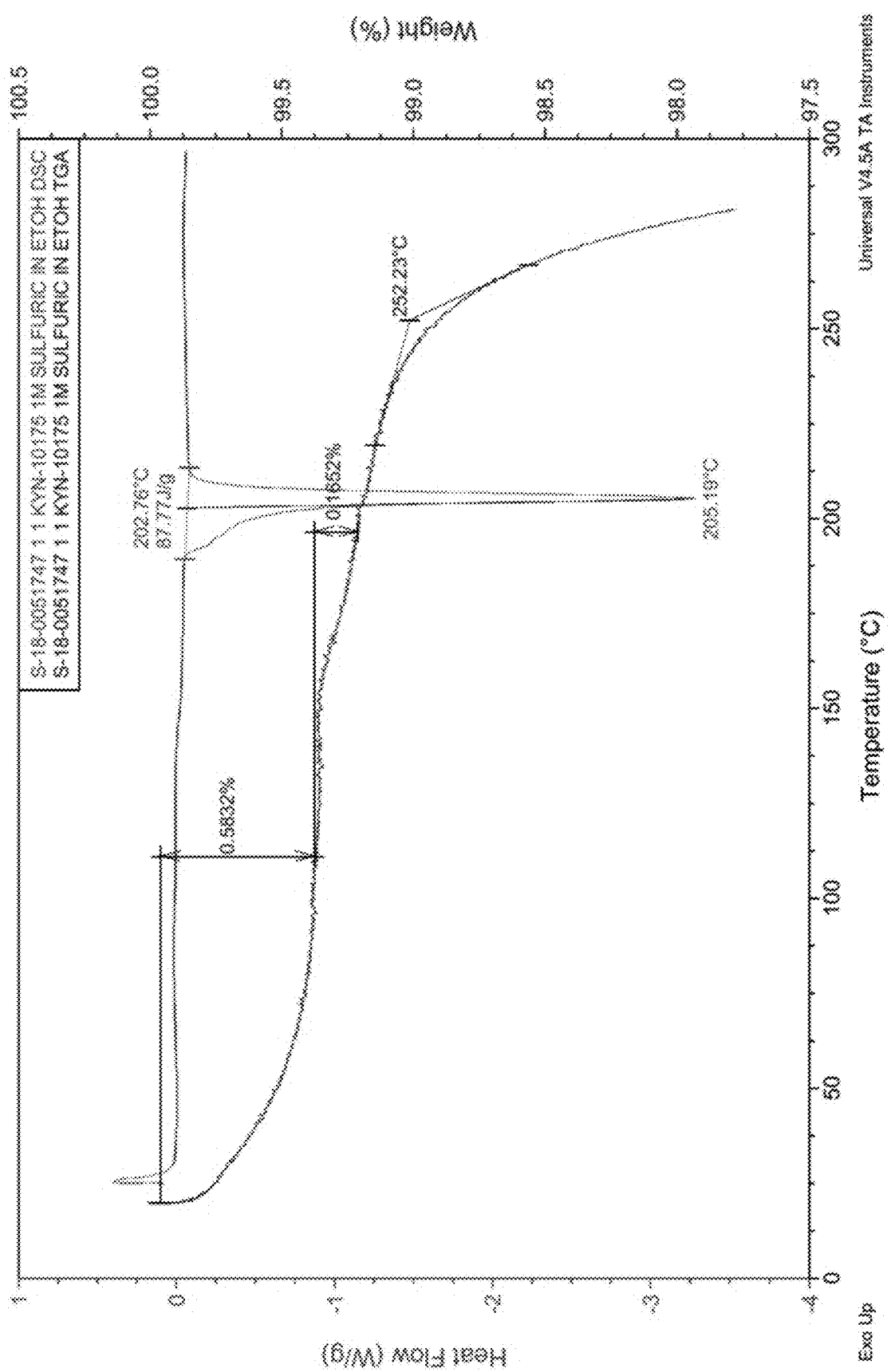
FIG. 2 depicts a TG/DTA trace of Compound A, Form B.

FIG. 2 depicts a TG/DTA trace of Form B of compound A.

Form C of Compound A

Form C of compound A was prepared as described above.

Table C, supra, is reproduced below and sets forth the X-ray diffraction peaks observed for Form C of compound A.

TABLE C

XRPD Peak Positions for Form C of Compound A

| Position [°2θ][1] | d-spacing [Å] | Intensity [%] |
|---|---|---|
| 6.02 | 14.6575 | 100 |
| 7.34 | 12.0353 | 37.5 |
| 8.45 | 10.4488 | 5.5 |
| 8.60 | 10.275 | 13.5 |
| 8.61 | 10.2605 | 39.2 |
| 9.03 | 9.7846 | 16.8 |
| 10.29 | 8.5906 | 81.2 |
| 13.27 | 6.668 | 12.9 |
| 14.28 | 6.1968 | 3 |
| 14.45 | 6.1252 | 21.4 |
| 14.86 | 5.9561 | 26 |
| 15.20 | 5.8241 | 4.8 |
| 15.53 | 5.6994 | 11.5 |
| 15.80 | 5.6027 | 3.6 |
| 16.54 | 5.3548 | 1.3 |
| 16.85 | 5.256 | 2.6 |
| 17.26 | 5.1331 | 28.9 |
| 17.69 | 5.0108 | 1.4 |
| 18.10 | 4.8972 | 8.1 |
| 18.29 | 4.8453 | 8.7 |
| 18.59 | 4.7689 | 1.4 |
| 19.09 | 4.6451 | 3.1 |
| 19.43 | 4.5653 | 6.3 |
| 19.61 | 4.5233 | 11.2 |
| 19.89 | 4.4608 | 5 |
| 20.25 | 4.3824 | 18.9 |
| 21.18 | 4.191 | 21.9 |
| 22.30 | 3.984 | 3.1 |
| 22.41 | 3.9644 | 6.2 |
| 22.90 | 3.881 | 2.5 |
| 23.53 | 3.7773 | 2.5 |
| 24.44 | 3.6389 | 1.2 |
| 24.82 | 3.5836 | 3.6 |
| 25.39 | 3.5055 | 1.3 |
| 25.66 | 3.4686 | 2.3 |
| 26.00 | 3.4238 | 9.4 |
| 26.14 | 3.4064 | 8.8 |
| 26.69 | 3.3367 | 4 |
| 27.04 | 3.2951 | 8.6 |

TABLE C-continued

XRPD Peak Positions for Form C of Compound A

| Position [°2θ][1] | d-spacing [Å] | Intensity [%] |
|---|---|---|
| 27.35 | 3.2585 | 7.9 |
| 28.02 | 3.1813 | 2 |
| 29.12 | 3.0638 | 2 |

[1]In this and all subsequent tables, the position 2θ is within ± 0.2.

FIG. 3 depicts an XRPD pattern of Form C of compound A.

Figure 4:
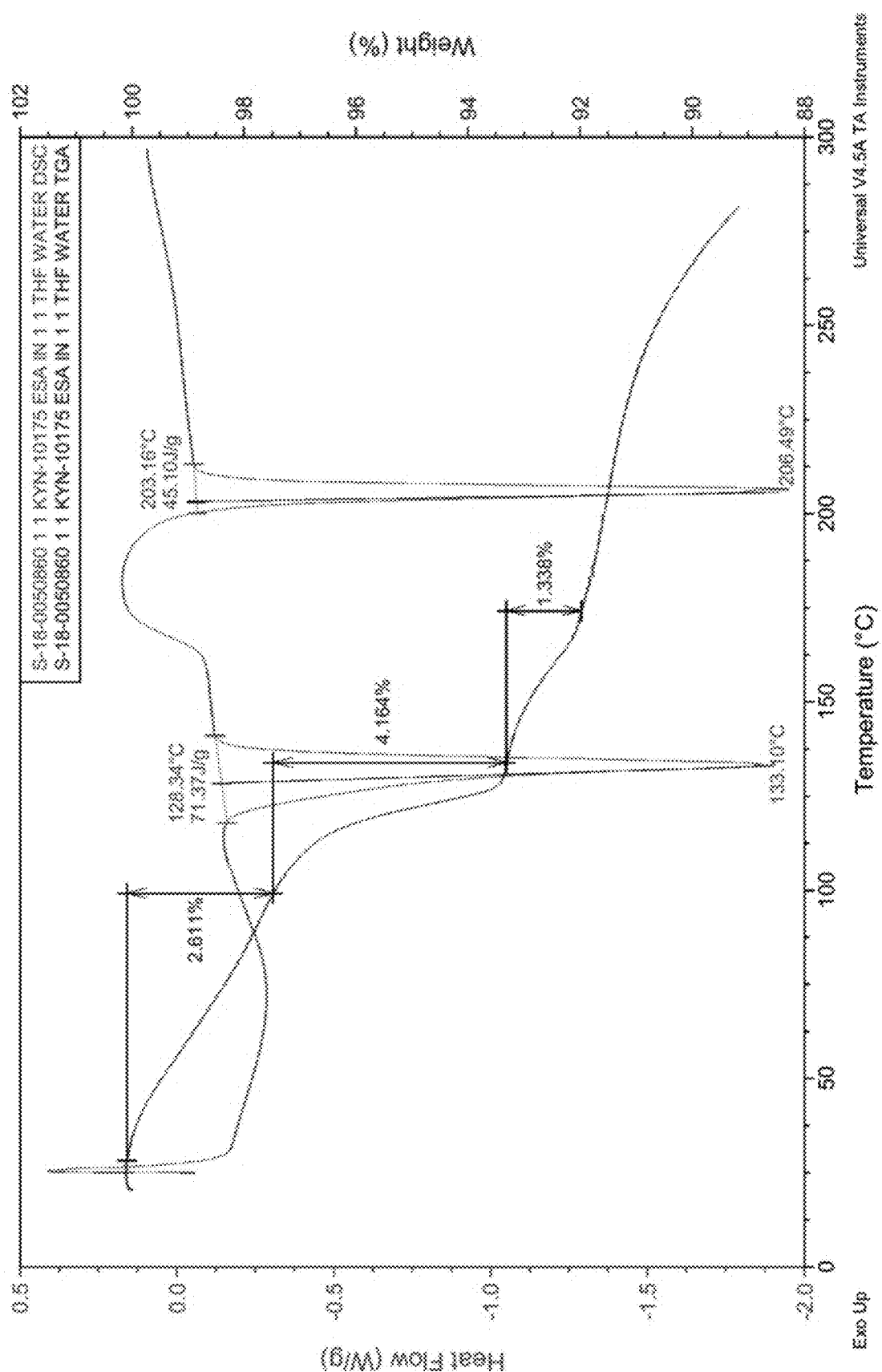
FIG. 4 depicts a TG/DTA trace of Compound A, Form C.

FIG. 4 depicts a TG/DTA trace of Form C of compound A.

Mixture of Form A and Form B of Compound A

Compound A hydrochloride salt (7.0 g) was dissolved in the mixture of EtOAc (150 mL) and saturated $NaHCO_3$ solution (200 mL) and stirred at 28° C. for 30 min. The mixture was extracted with EtOAc (150 mL×3). The combined organic layers were washed with brine (200 mL×2), dried over $Na_2SO_4$ and concentrated to yield a residue which was added to MeOH (150 mL) and stirred for 30 min. The mixture was filtered and the filtered cake was concentrated to yield the desired product which was lyophilized to yield a mixture of Form A and Form B of compound A (6.7 g) as a solid.

FIG. 24 depicts an XRPD pattern of a mixture of Form A and Form B of compound A.

FIG. 25 depicts TGA/DSC of a mixture of Form A and Form B of compound A.

Example 2—Preparation of Form A of Compound 1

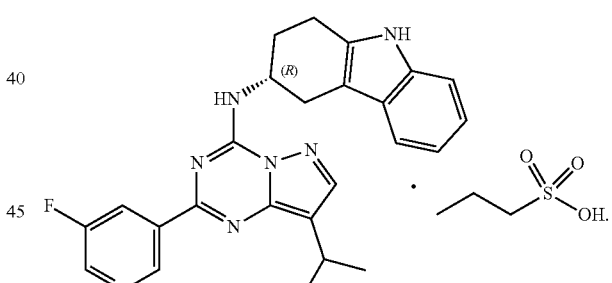

1

Form A of Compound 1

Form A of compound 1 was prepared as described above.

Table 1, supra, is reproduced below and sets forth the X-ray diffraction peaks observed for Form A of compound 1.

TABLE 1

XRPD Peak Positions for Form A of Compound 1

| Position [°2θ] | d-spacing [Å] | Intensity [%] |
|---|---|---|
| 5.8 | 15.3556 | 100 |
| 9.0 | 9.7887 | 4.8 |
| 11.6 | 7.6552 | 50.4 |
| 12.7 | 6.9761 | 2.4 |
| 13.5 | 6.5581 | 7.2 |
| 13.9 | 6.3739 | 6.4 |
| 14.2 | 6.2271 | 20 |

TABLE 1-continued

XRPD Peak Positions for Form A of Compound 1

| Position [°2θ] | d-spacing [Å] | Intensity [%] |
|---|---|---|
| 15.0 | 5.8855 | 16 |
| 15.3 | 5.7732 | 2.3 |
| 16.2 | 5.467 | 5 |
| 16.9 | 5.2552 | 1.1 |
| 17.4 | 5.099 | 4 |
| 18.1 | 4.8971 | 2.6 |
| 18.8 | 4.7082 | 32.3 |
| 19.4 | 4.5638 | 1.8 |
| 20.7 | 4.2954 | 6.3 |
| 23.2 | 3.8286 | 2.6 |
| 23.9 | 3.716 | 1.7 |
| 24.4 | 3.6524 | 2.1 |
| 24.5 | 3.6304 | 2.1 |
| 24.9 | 3.5667 | 1.7 |
| 25.5 | 3.4859 | 12.2 |
| 25.9 | 3.4353 | 14 |
| 26.5 | 3.3649 | 0.6 |
| 27.2 | 3.2797 | 3.6 |
| 27.6 | 3.2317 | 2.6 |
| 28.1 | 3.1783 | 1.1 |
| 28.3 | 3.1519 | 4.2 |
| 28.7 | 3.1126 | 1.9 |
| 29.2 | 3.0595 | 3.8 |
| 29.5 | 3.0212 | 0.9 |
| 31.1 | 2.8721 | 0.8 |
| 32.8 | 2.7304 | 0.8 |
| 33.1 | 2.7026 | 0.6 |
| 35.1 | 2.5538 | 1 |
| 35.9 | 2.4998 | 1.1 |
| 39.5 | 2.282 | 0.7 |

FIG. 5 depicts an XRPD pattern of Form A of compound 1.

Figure 6:
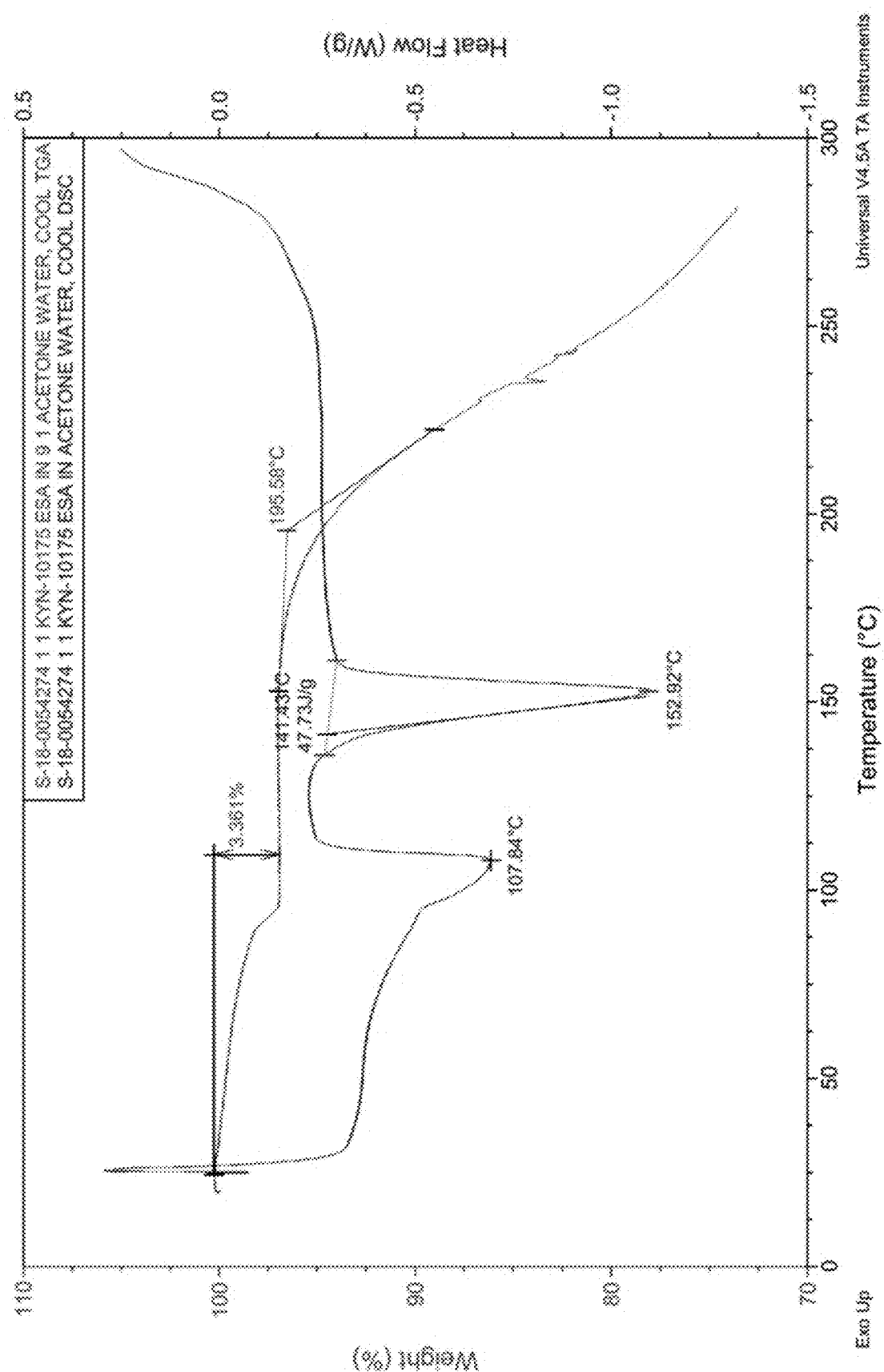
FIG. 6 depicts a TG/DTA trace of Compound 1, Form A.

FIG. 6 depicts a TG/DTA trace of Form A of compound 1.

Form B of Compound 1

Form B of compound 1 was prepared as described above. Table 2, supra, is reproduced below and sets forth the X-ray diffraction peaks observed for Form B of compound 1.

TABLE 2

XRPD Peak Positions for Form B of Compound 1

| Position [°2θ] | d-spacing [Å] | Intensity [%] |
|---|---|---|
| 5.1 | 17.2744 | 1.5 |
| 5.6 | 15.7493 | 100 |
| 8.9 | 9.9195 | 1.3 |
| 9.5 | 9.3413 | 1.2 |
| 9.9 | 8.965 | 0.1 |
| 10.2 | 8.7059 | 0.4 |
| 10.9 | 8.1087 | 1.8 |
| 11.2 | 7.8636 | 60 |
| 12.2 | 7.2352 | 0.1 |
| 12.8 | 6.9174 | 0 |
| 13.2 | 6.6957 | 3 |
| 14.0 | 6.3029 | 1.3 |
| 14.7 | 6.0184 | 0.3 |
| 15.0 | 5.9183 | 3.2 |
| 15.7 | 5.643 | 1 |
| 16.2 | 5.4526 | 0.1 |
| 16.9 | 5.2422 | 6.7 |
| 17.5 | 5.0508 | 0 |
| 17.9 | 4.9563 | 0.2 |
| 18.5 | 4.7908 | 1.1 |
| 19.8 | 4.4798 | 0.3 |
| 20.9 | 4.238 | 1.2 |
| 21.6 | 4.1127 | 0.1 |
| 22.0 | 4.0401 | 0.1 |
| 22.5 | 3.9459 | 0.6 |
| 23.7 | 3.7457 | 0.3 |

TABLE 2-continued

XRPD Peak Positions for Form B of Compound 1

| Position [°2θ] | d-spacing [Å] | Intensity [%] |
|---|---|---|
| 24.2 | 3.6719 | 0.1 |
| 24.6 | 3.6151 | 0.3 |
| 25.6 | 3.4774 | 1.8 |
| 26.0 | 3.4236 | 0.2 |
| 26.6 | 3.3461 | 0.8 |
| 26.8 | 3.321 | 0.2 |
| 28.4 | 3.1454 | 3.2 |
| 29.2 | 3.0548 | 0.5 |

FIG. 7 depicts an XRPD pattern of Form B of compound 1.

Example 3—Preparation of Form A of Compound 2

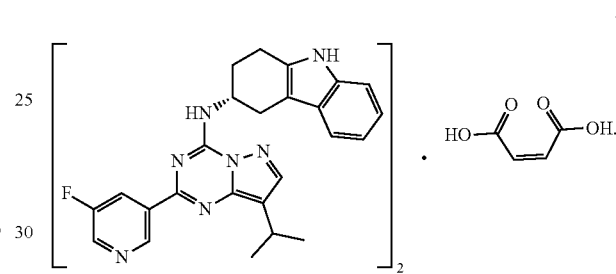

Form A of Compound 2

Form A of compound 2 was prepared as described above. Table 3, supra, is reproduced below and sets forth the X-ray diffraction peaks observed for Form A of compound 2.

TABLE 3

XRPD Peak Positions for Form A of Compound 2

| Position [°2θ] | d-spacing [Å] | Intensity [%] |
|---|---|---|
| 5.3 | 16.6727 | 100 |
| 6.6 | 13.3333 | 3.8 |
| 8.0 | 11.0992 | 4 |
| 9.6 | 9.2459 | 3.9 |
| 10.6 | 8.3351 | 3.2 |
| 11.3 | 7.8022 | 40.9 |
| 13.3 | 6.6763 | 10.7 |
| 14.1 | 6.2596 | 1.9 |
| 14.7 | 6.0118 | 1.1 |
| 16.0 | 5.5517 | 24.5 |
| 16.8 | 5.2683 | 2 |
| 17.4 | 5.1039 | 1.3 |
| 17.8 | 4.9827 | 3.6 |
| 18.7 | 4.7433 | 1.2 |
| 19.2 | 4.6251 | 2.2 |
| 19.9 | 4.4483 | 0.6 |
| 20.7 | 4.293 | 3.4 |
| 21.3 | 4.1699 | 5.6 |
| 22.7 | 3.9225 | 2.3 |
| 24.0 | 3.7105 | 3.1 |
| 24.5 | 3.6303 | 2.4 |
| 26.3 | 3.3879 | 1.6 |
| 26.7 | 3.3409 | 2.1 |
| 27.1 | 3.2939 | 2 |
| 27.6 | 3.2338 | 0.6 |
| 28.1 | 3.1769 | 0.9 |
| 28.8 | 3.1015 | 0.3 |
| 29.3 | 3.0447 | 0.6 |

TABLE 3-continued

| XRPD Peak Positions for Form A of Compound 2 |||
| --- | --- | --- |
| Position [°2θ] | d-spacing [Å] | Intensity [%] |
| 31.8 | 2.8079 | 0.5 |
| 32.2 | 2.7771 | 0.5 |

Figure 8:
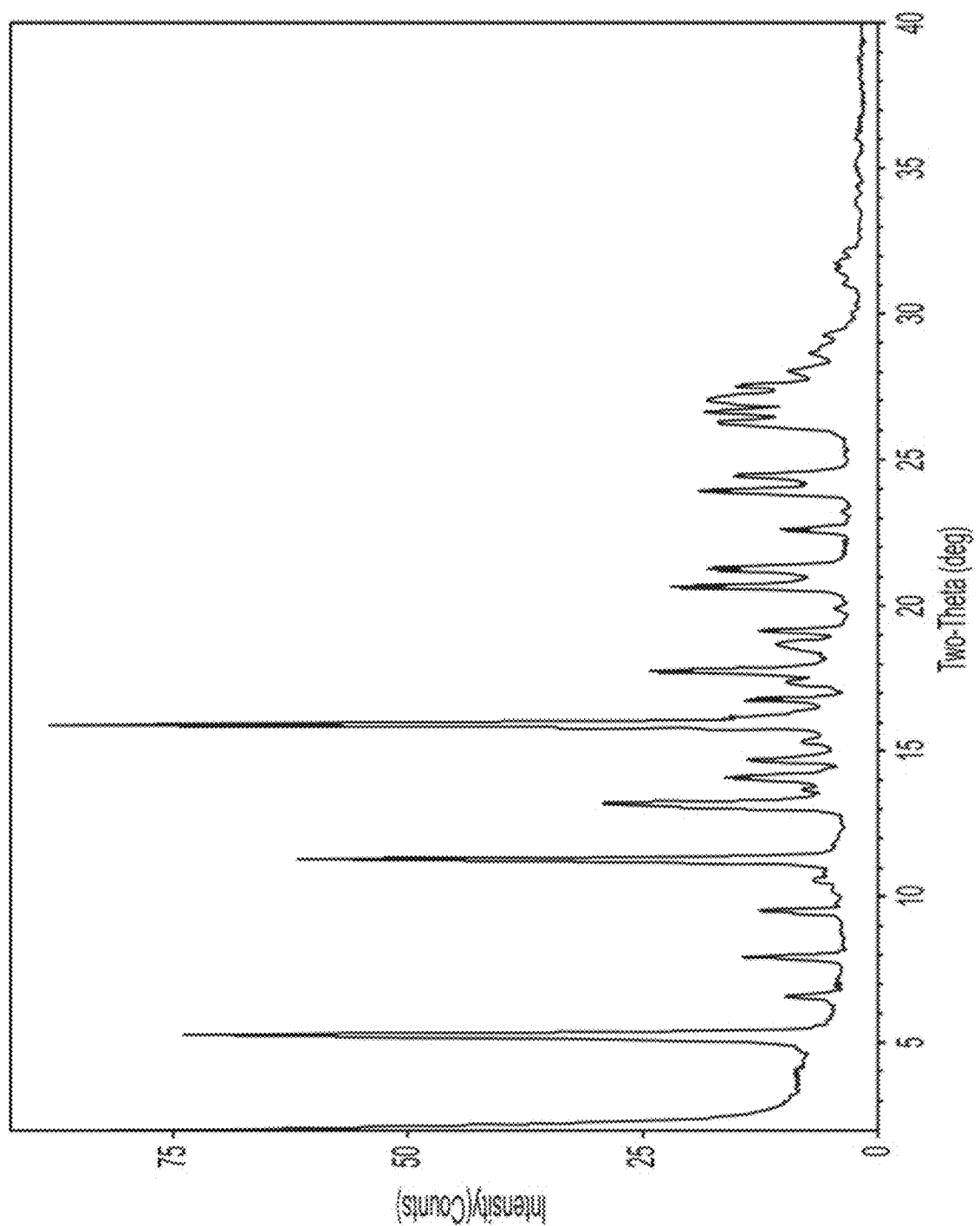
FIG. 8 depicts the XRPD pattern of Compound 2, Form A.

FIG. 8 depicts an XRPD pattern of Form A of compound 2.

FIG. 9 depicts a TG/DTA trace of Form A of compound 2.

Example 4—Preparation of Form A of Compound 3

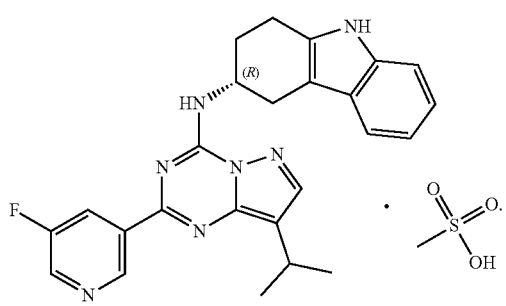

3

Form A of Compound 3

Form A of compound 3 was prepared as described above.
Table 4, supra, is reproduced below and sets forth the X-ray diffraction peaks observed for Form A of compound 3.

TABLE 4

| XRPD Peak Positions for Form A of Compound 3 |||
| --- | --- | --- |
| Position [°2θ] | d-spacing [Å] | Intensity [%] |
| 5.1 | 17.2728 | 1.2 |
| 5.6 | 15.7025 | 100 |
| 9.0 | 9.7695 | 3.6 |
| 10.2 | 8.7061 | 0.3 |
| 11.0 | 8.0007 | 2.7 |
| 11.2 | 7.8648 | 35 |
| 12.1 | 7.3154 | 0.4 |
| 12.4 | 7.1465 | 0.3 |
| 13.3 | 6.6505 | 2.9 |
| 14.0 | 6.313 | 3.2 |
| 14.3 | 6.1969 | 2.1 |
| 15.3 | 5.7988 | 6.3 |
| 15.8 | 5.6164 | 1.7 |
| 16.3 | 5.4343 | 0.4 |
| 16.9 | 5.2456 | 8 |
| 18.0 | 4.9265 | 0.4 |
| 18.4 | 4.8306 | 0.6 |
| 18.7 | 4.7514 | 1.9 |
| 18.9 | 4.7028 | 1.8 |
| 19.5 | 4.5477 | 0.7 |
| 20.0 | 4.4386 | 0.4 |
| 21.0 | 4.229 | 1.2 |
| 22.0 | 4.0295 | 0.4 |
| 24.2 | 3.6743 | 0.5 |
| 25.5 | 3.4972 | 5.3 |
| 25.9 | 3.4328 | 0.7 |
| 26.7 | 3.3316 | 1.6 |
| 28.3 | 3.1506 | 2.5 |
| 29.2 | 3.053 | 0.5 |

Figure 10:
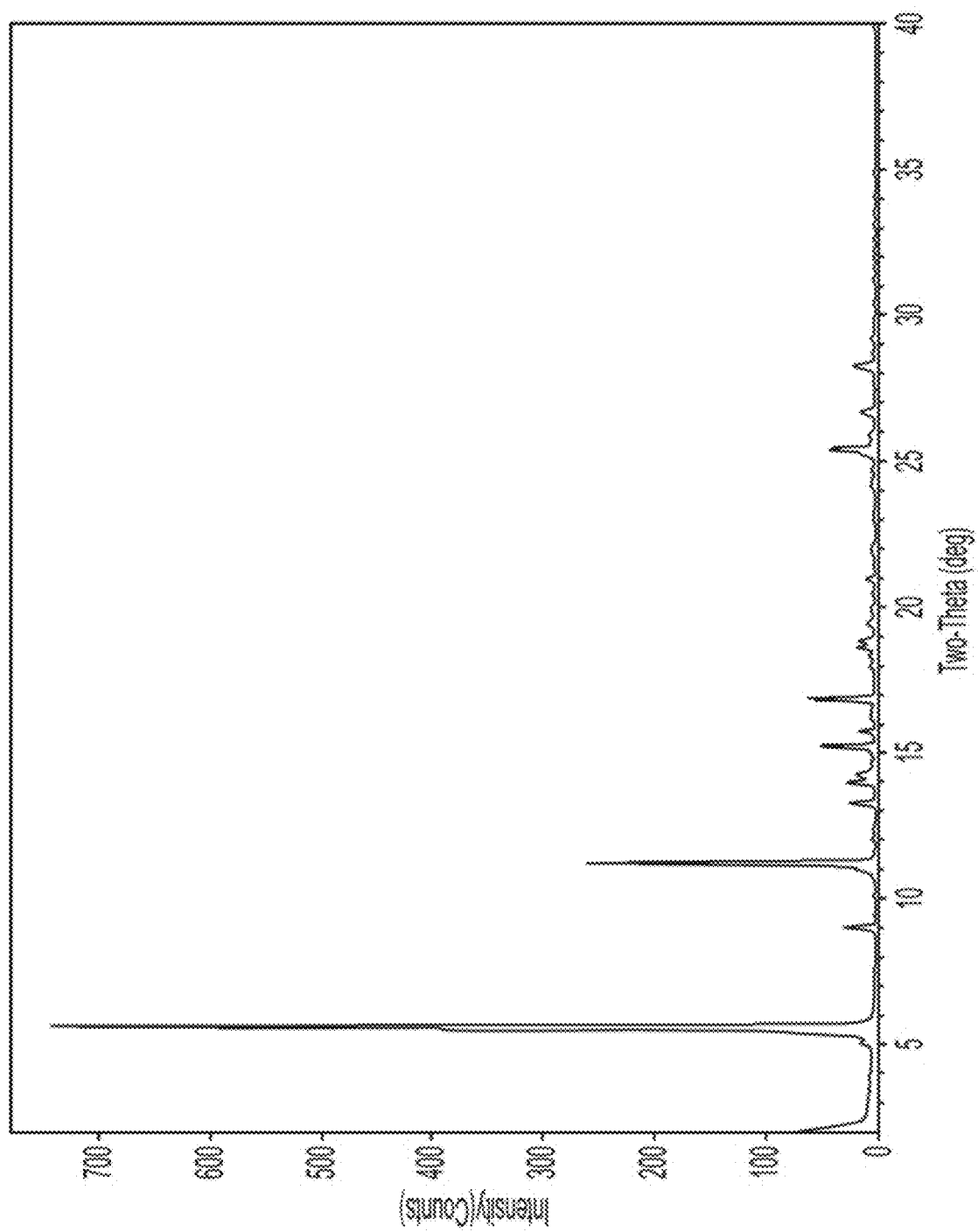
FIG. 10 depicts the XRPD pattern of Compound 3, Form A.

FIG. 10 depicts an XRPD pattern of Form A of compound 3.

FIG. 11 depicts a TG/DTA trace of Form A of compound 3.

Form B of Compound 3

Form B of compound 3 was prepared as described above.
Table 5, supra, is reproduced below and sets forth the X-ray diffraction peaks observed for Form B of compound 3.

TABLE 5

| XRPD Peak Positions for Form B of Compound 3 |||
| --- | --- | --- |
| Position [°2θ] | d (Angstroms) | Intensity [%] |
| 6.0 | 14.7036 | 100 |
| 11.6 | 7.6195 | 10 |
| 12.1 | 7.3357 | 32.3 |
| 13.6 | 6.5115 | 2.1 |
| 14.6 | 6.0801 | 3.1 |
| 15.6 | 5.66 | 2 |
| 16.1 | 5.514 | 0.6 |
| 17.6 | 5.0376 | 4.5 |
| 18.1 | 4.8948 | 12.5 |
| 19.8 | 4.4702 | 1 |
| 20.1 | 4.4033 | 3.3 |
| 20.8 | 4.2687 | 0.2 |
| 21.1 | 4.2034 | 1.3 |
| 21.9 | 4.0542 | 2.2 |
| 22.2 | 4.0022 | 4.2 |
| 22.6 | 3.9386 | 0.5 |
| 23.0 | 3.8694 | 0.3 |
| 23.5 | 3.7822 | 1.2 |
| 24.3 | 3.6649 | 0.3 |
| 25.1 | 3.5465 | 1.8 |
| 26.9 | 3.3177 | 1.9 |
| 27.4 | 3.2583 | 3 |
| 28.3 | 3.1563 | 0.9 |
| 29.4 | 3.0401 | 0.9 |

Figure 12:
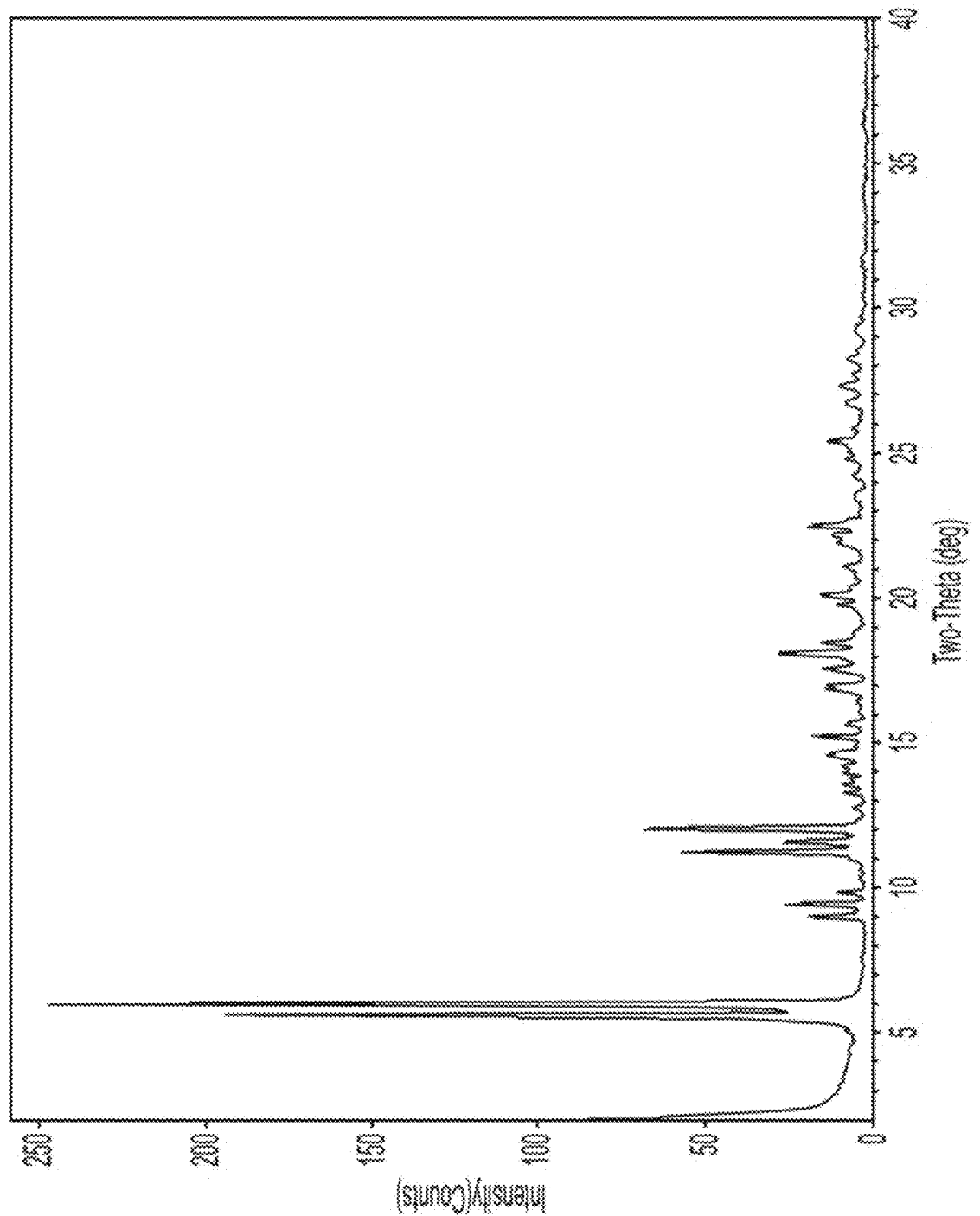
FIG. 12 depicts the XRPD pattern of Compound 3, Form B.

FIG. 12 depicts an XRPD pattern of Form B of compound 3.

FIG. 13 depicts a TG/DTA trace of Form B of compound 3.

Example 5—Preparation of Form A of Compound 4

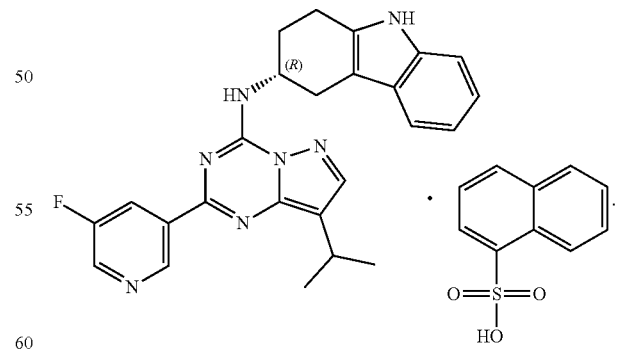

4

Form A of Compound 4

Form A of compound 4 was prepared as described above.
Table 6, supra, is reproduced below and sets forth the X-ray diffraction peaks observed for Form A of compound 4.

TABLE 6

XRPD Peak Positions for Form A of Compound 4

| Position [°2θ] | d (Angstroms) | Intensity [%] |
|---|---|---|
| 6.8 | 13.0644 | 1.1 |
| 7.5 | 11.81 | 100 |
| 7.8 | 11.2555 | 9.4 |
| 8.4 | 10.5306 | 78.5 |
| 9.5 | 9.3437 | 5.7 |
| 9.8 | 9.0463 | 7.2 |
| 9.9 | 8.8891 | 7.5 |
| 11.1 | 7.9975 | 8.2 |
| 11.9 | 7.404 | 5.2 |
| 12.6 | 7.0284 | 1.4 |
| 12.9 | 6.8706 | 1.6 |
| 13.5 | 6.5355 | 5 |
| 13.8 | 6.4284 | 11.9 |
| 14.5 | 6.1263 | 26.4 |
| 14.7 | 6.029 | 1.2 |
| 15.1 | 5.8748 | 8.3 |
| 15.8 | 5.6186 | 10.1 |
| 16.1 | 5.5086 | 4 |
| 16.5 | 5.3844 | 20.1 |
| 16.6 | 5.3221 | 1.8 |
| 16.8 | 5.2691 | 1.7 |
| 17.3 | 5.1223 | 1.3 |
| 18.1 | 4.9044 | 11.6 |
| 19.1 | 4.6279 | 4.7 |
| 19.6 | 4.5254 | 11.4 |
| 19.7 | 4.496 | 9.8 |
| 20.1 | 4.424 | 47.9 |
| 20.6 | 4.2976 | 7.6 |
| 20.9 | 4.2364 | 2.5 |
| 21.5 | 4.1352 | 0.3 |
| 21.8 | 4.0652 | 1.1 |
| 22.0 | 4.0293 | 5.8 |
| 22.4 | 3.9624 | 28.3 |
| 22.9 | 3.8768 | 1.7 |
| 23.7 | 3.745 | 7.5 |
| 24.6 | 3.6159 | 5.8 |
| 24.8 | 3.5884 | 3.8 |
| 25.2 | 3.5259 | 2.9 |

Figure 14:
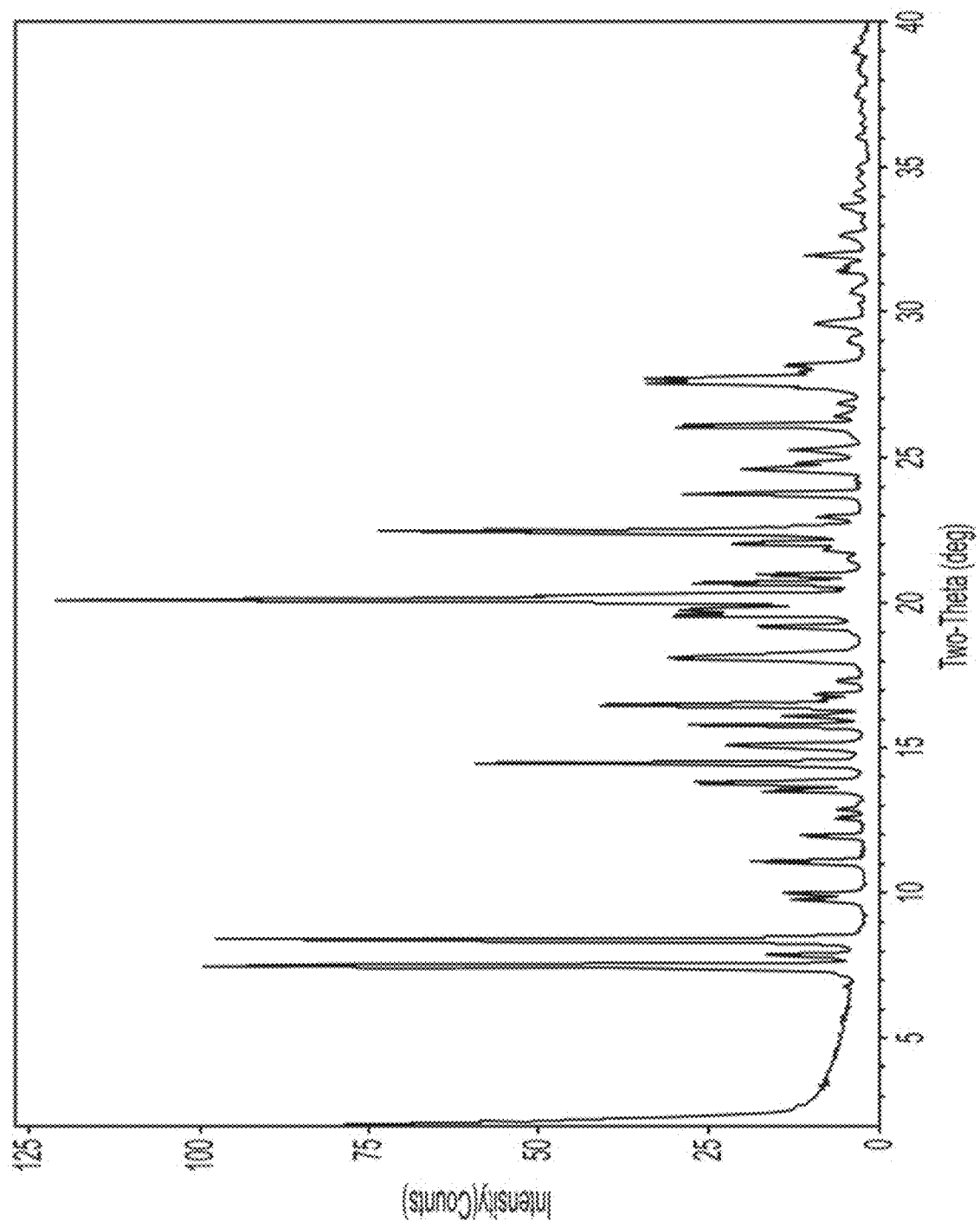
FIG. 14 depicts the XRPD pattern of Compound 4, Form A.

FIG. 14 depicts an XRPD pattern of Form A of compound 4.

FIG. 15 depicts a TG/DTA trace of Form A of compound 4.

Example 6—Preparation of Form A of Compound 5

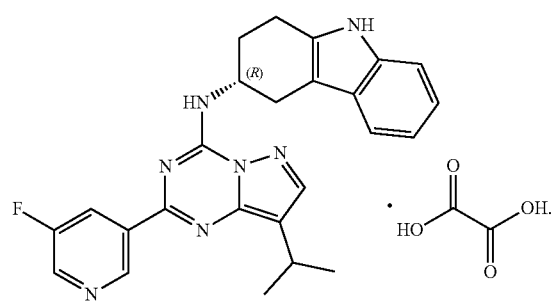

Form A of Compound 5

Form A of compound 5 was prepared as described above.

Table 7, supra, is reproduced below and sets forth the X-ray diffraction peaks observed for Form A of compound 5.

TABLE 7

XRPD Peak Positions for Form A of Compound 5

| Position [°2θ] | d-spacing [Å] | Intensity [%] |
|---|---|---|
| 6.4 | 13.7901 | 100 |
| 7.1 | 12.4378 | 20.2 |
| 11.4 | 7.7871 | 4.9 |
| 12.7 | 6.9614 | 63.9 |
| 14.4 | 6.1639 | 6 |
| 17.5 | 5.0766 | 16.5 |
| 18.3 | 4.8405 | 3.3 |
| 19.2 | 4.6288 | 3.2 |
| 21.1 | 4.2167 | 2.7 |
| 22.3 | 3.9765 | 1.7 |
| 23.1 | 3.8472 | 8.2 |
| 27.3 | 3.2647 | 1.7 |
| 29.0 | 3.0719 | 0.9 |

Figure 16:
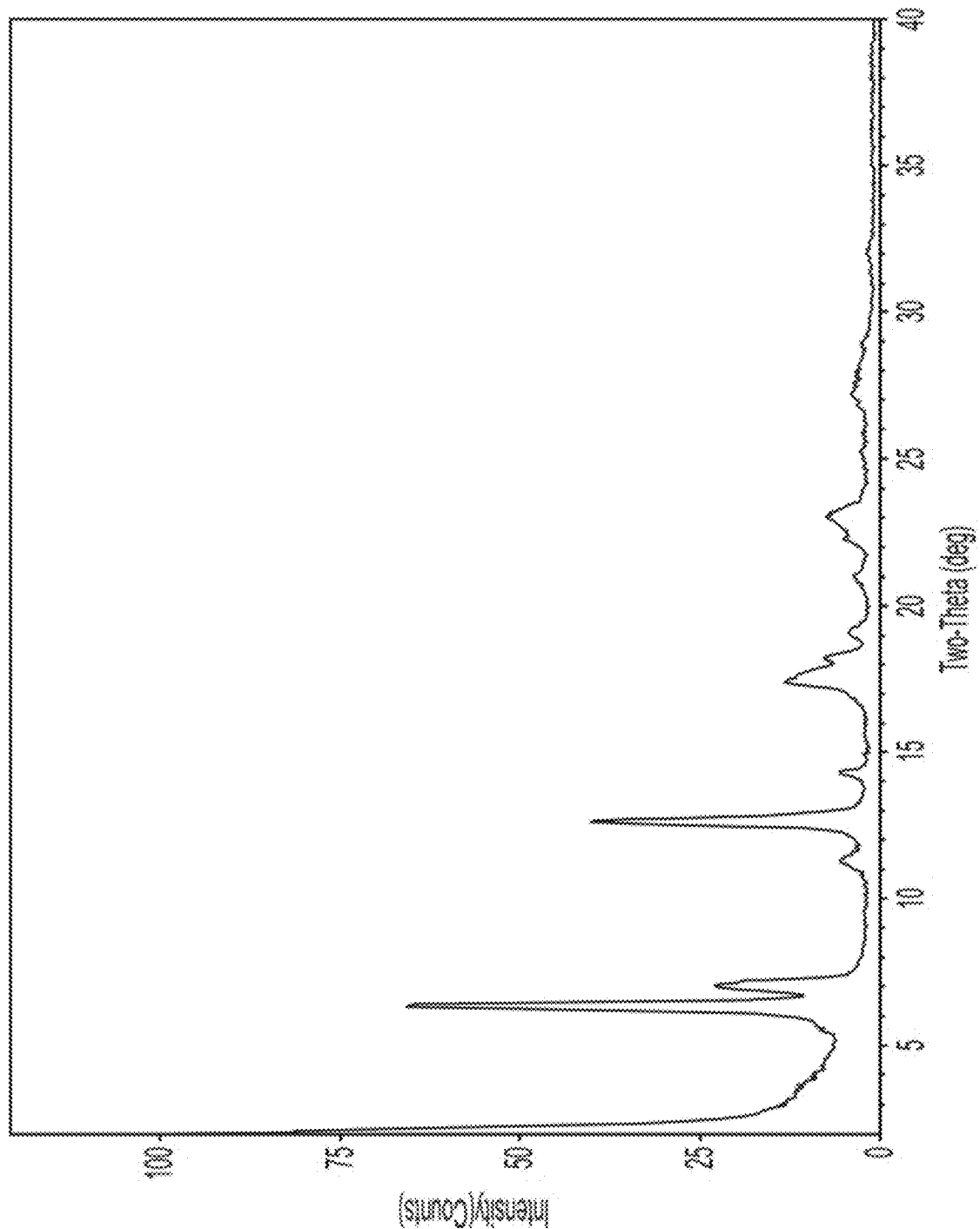
FIG. 16 depicts the XRPD pattern of Compound 5, Form A.

FIG. 16 depicts an XRPD pattern of Form A of compound 5.

FIG. 17 depicts a TG/DTA trace of Form A of compound 5.

Example 7—Preparation of Forms A and B of Compound 6

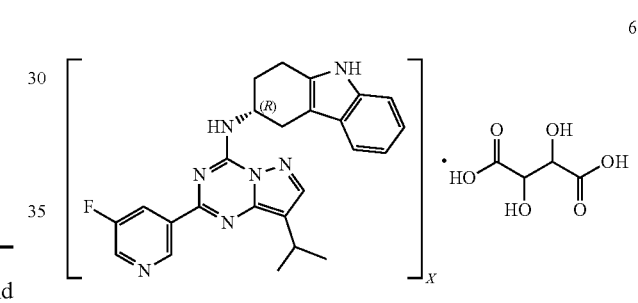

wherein X is about 1 or 2.

Form A of Compound 6

Form A of compound 6 was prepared as described above. Form A of compound 6 was determined to comprise compound A and ethanedisulfonic acid in a ratio of about 1:1.

Table 8, supra, is reproduced below and sets forth the X-ray diffraction peaks observed for Form A of compound 6.

TABLE 8

XRPD Peak Positions for Form A of Compound 6

| Position [°2θ] | d-spacing [Å] | Intensity [%] |
|---|---|---|
| 5.5 | 16.1924 | 100 |
| 7.0 | 12.6864 | 1.4 |
| 8.2 | 10.8305 | 7.5 |
| 8.4 | 10.5158 | 9 |
| 9.1 | 9.6845 | 0.7 |
| 10.3 | 8.5415 | 1.6 |
| 11.1 | 7.9331 | 15.7 |
| 13.4 | 6.6022 | 1.1 |
| 14.5 | 6.1046 | 5 |
| 15.6 | 5.6633 | 4.8 |
| 16.3 | 5.4202 | 4.5 |
| 17.4 | 5.1082 | 13.5 |
| 17.6 | 5.0375 | 6.7 |
| 18.9 | 4.7033 | 17.7 |
| 20.3 | 4.371 | 4 |
| 22.3 | 3.976 | 5.8 |

TABLE 8-continued

XRPD Peak Positions for Form A of Compound 6

| Position [°2θ] | d-spacing [Å] | Intensity [%] |
|---|---|---|
| 23.1 | 3.8469 | 6.6 |
| 24.5 | 3.6371 | 4.1 |
| 26.3 | 3.3865 | 8.3 |
| 26.7 | 3.3422 | 5.9 |
| 27.0 | 3.2941 | 2.6 |
| 29.9 | 2.9861 | 3.4 |

Figure 18:
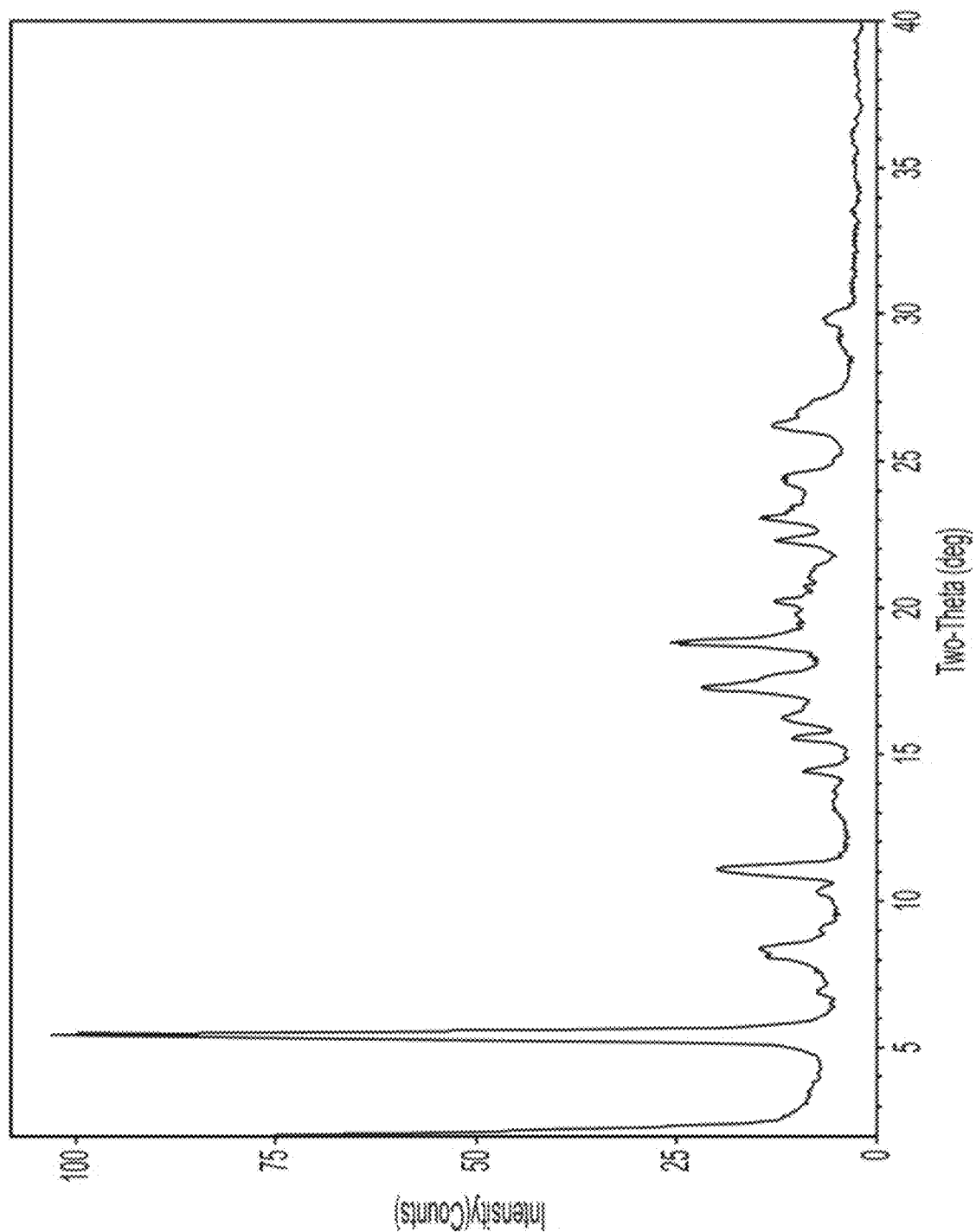
FIG. 18 depicts the XRPD pattern of Compound 6, Form A.

FIG. 18 depicts an XRPD pattern of Form A of compound 6.

FIG. 19 depicts a TG/DTA trace of Form A of compound 6.

Form B of Compound 6

Form B of compound 6 was prepared as described above. Form B of compound 6 was determined to comprise compound A and ethanedisulfonic acid in a ratio of about 2:1.

Table 9, supra, is reproduced below and sets forth the X-ray diffraction peaks observed for Form B of compound 6.

TABLE 9

XRPD Peak Positions for Form B of Compound 6

| Position [°2θ] | d-spacing [Å] | Intensity [%] |
|---|---|---|
| 5.3 | 16.5046 | 1.7 |
| 6.2 | 14.2356 | 74.6 |
| 6.8 | 13.0713 | 100 |
| 7.2 | 12.183 | 2.4 |
| 8.6 | 10.2145 | 5 |
| 9.5 | 9.2819 | 0.6 |
| 10.7 | 8.2682 | 8.2 |
| 11.5 | 7.7192 | 4.5 |
| 12.4 | 7.1588 | 12.4 |
| 13.5 | 6.5301 | 24.8 |
| 14.6 | 6.0796 | 6.9 |
| 16.3 | 5.4162 | 2.1 |
| 17.1 | 5.1667 | 11.2 |
| 17.7 | 5.0058 | 3.2 |
| 18.7 | 4.7289 | 9.7 |
| 19.3 | 4.5962 | 3 |
| 20.6 | 4.3182 | 15.7 |
| 20.9 | 4.2371 | 11.5 |
| 21.8 | 4.0643 | 5.9 |
| 23.2 | 3.8387 | 0.8 |
| 24.3 | 3.6659 | 1.8 |
| 25.3 | 3.5112 | 1 |
| 26.1 | 3.4101 | 1.3 |

Figure 20:
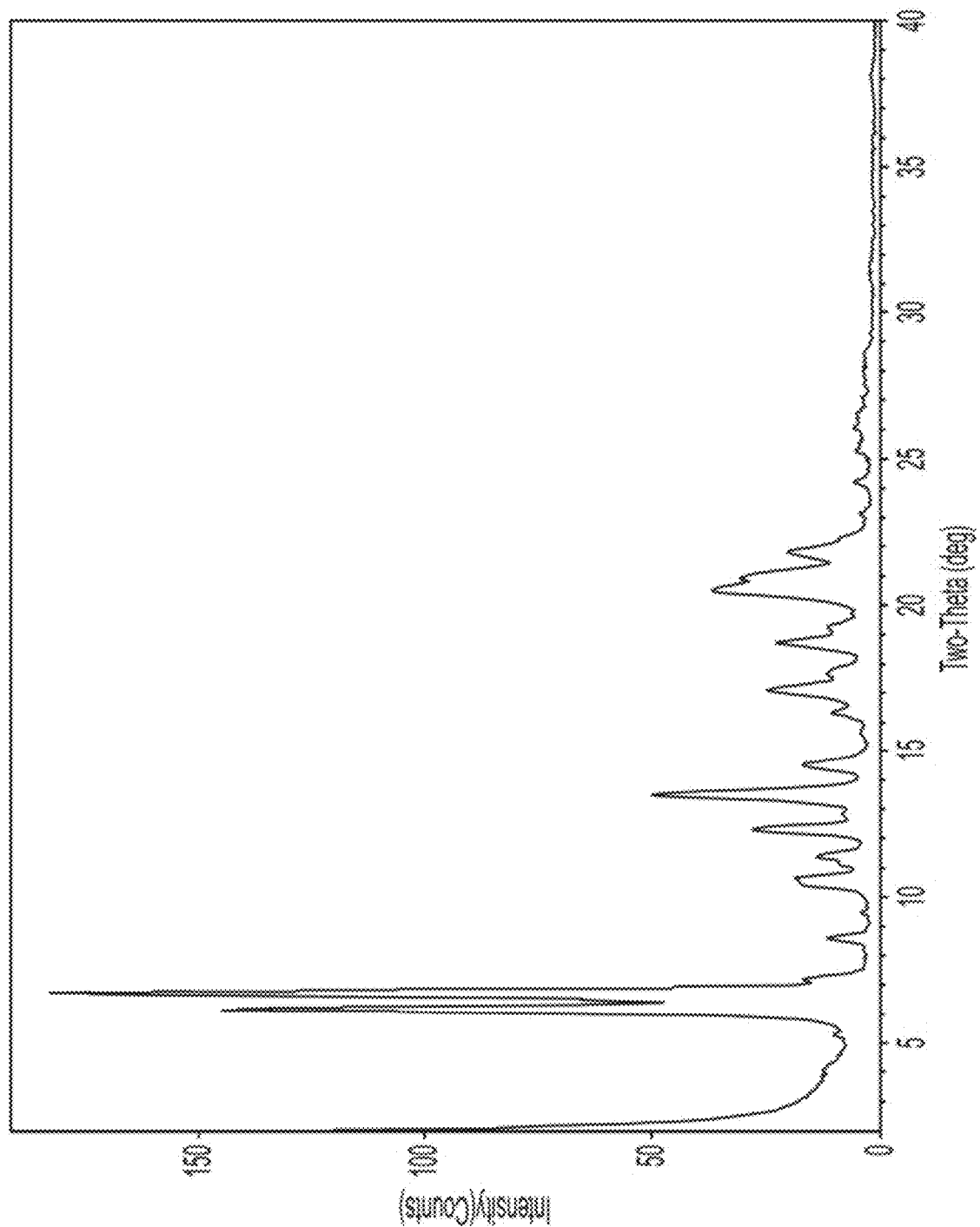
FIG. 20 depicts the XRPD pattern of Compound 6, Form B.

FIG. 20 depicts an XRPD pattern of Form B of compound 6.

FIG. 21 depicts a TG/DTA trace of Form B of compound 6.

Example 8—Preparation of Form A of Compound 7

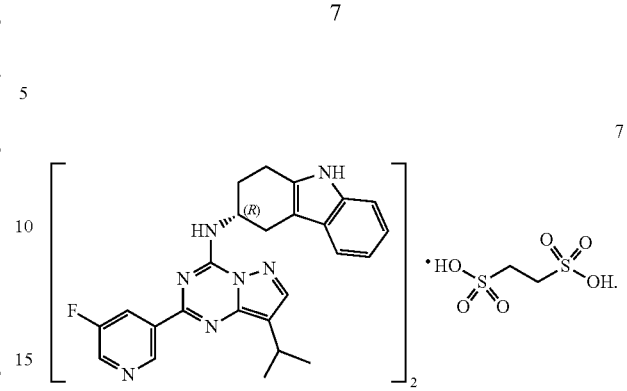

Form A of Compound 7

Form A of compound 7 was prepared as described above.

Table 10, supra, is reproduced below and sets forth the X-ray diffraction peaks observed for Form A of compound 7.

TABLE 10

XRPD Peak Positions for Form A of Compound 7

| Position [°2θ] | d-spacing [Å] | Intensity [%] |
|---|---|---|
| 6.6 | 13.4754 | 100 |
| 8.0 | 11.0262 | 0.7 |
| 10.4 | 8.5378 | 5 |
| 13.2 | 6.7031 | 7.3 |
| 16.0 | 5.5191 | 2.4 |
| 18.2 | 4.871 | 0.8 |
| 19.1 | 4.6422 | 1.8 |
| 19.3 | 4.5954 | 1.7 |
| 20.4 | 4.3516 | 0.7 |
| 22.4 | 3.9584 | 1.5 |
| 26.5 | 3.3549 | 0.6 |

Figure 22:
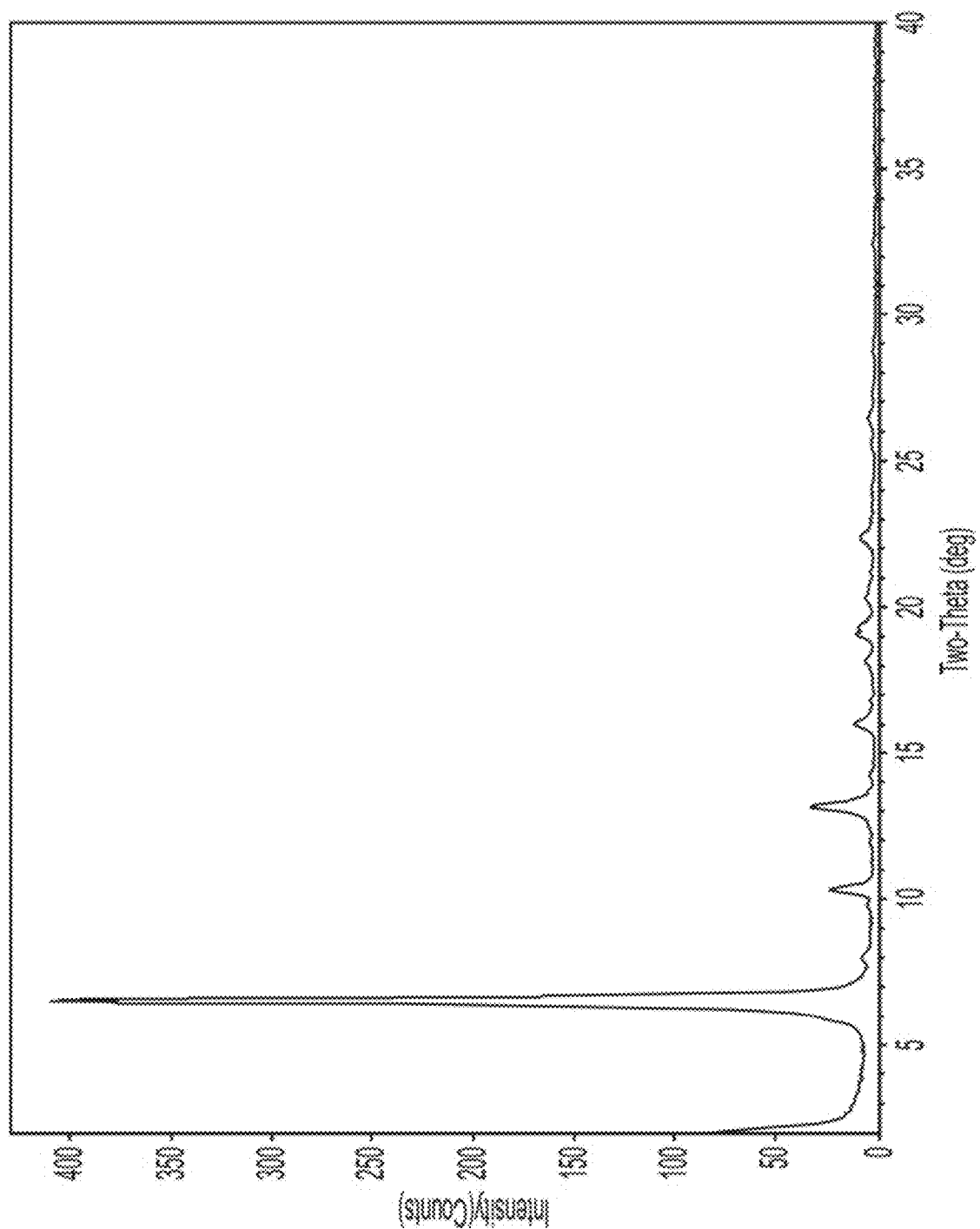
FIG. 22 depicts the XRPD pattern of Compound 7, Form A.

FIG. 22 depicts an XRPD pattern of Form A of compound 7.

FIG. 23 depicts a TG/DTA trace of Form A of compound 7.

Example 9—Solubility Studies

Solubility studies of compound A, Form B, Compound 1, Form B, Compound 2, Form A, Compound 3, Form B, and Compound 4, Form A was determined in water, fasted-state simulated intestinal fluid (FaSSIF), fed-state simulated intestinal fluid (FeSSIF), and fasted-state simulated gastric fluid (FaSSGF). Simulated fluids were sourced from and prepared according to biorelevant.com using their FaSSIF/FeSSIF/FaSSGF Powder (v1, formerly known as SIF Powder). Samples were prepared by adding excess solids to 5 mL of medium at 37° C. Samples were pulled and filtered at 30 minutes, 120 minutes, and 24 hours and tested for solution concentration using the HPLC parameters described below in Table 13.

TABLE 13

| HPLC Parameters | |
|---|---|
| HPLC Method Condition | |
| Parameter | Value |
| Column | Waters XBridge BEH C18 3.5 μm, 3 × 50 mm, p/n = 186003026 |
| Column Temperature | 35° C. |
| Mobile Phase A | 0.1% Formic Acid in Water |
| Mobile Phase B | 0.1% Formic Acid in Acetonitrile |
| Seal Wash Solvent | 10% Acetonitrile in Water |
| Needle Wash Solvent | 50% Tetrahydrofuran in Water |
| Diluent | 1:1 Tetrahydrofuran (unstabilized):Water |
| Injection Volume | 5 μL |
| Detection Wavelength | 345 nm |
| Analytical Concentration | Target 0.5 mg/mL |

TABLE 13-continued

| HPLC Parameters | | | |
|---|---|---|---|
| Gradient Profile | | | |
| Time (min) | Mobile Phase A | Mobile Phase B | Flow (mL/min) |
| 0 | 95 | 5 | 1.00 |
| 7 | 5 | 95 | 1.00 |
| 7.1 | 95 | 5 | 1.00 |
| 10 | 95 | 5 | 1.00 |

The pH of the samples at each timepoint was also measured; pH paper was used at 30 minutes and 120 minutes due to the small sample size, and a pH meter was used at 24 hours. The remaining material from all trials was analyzed by XRPD after 24 hours to determine if any polymorphic form changes had taken place. The remaining material from trials in water was analyzed by NMR after 24 hours to determine if disassociation had taken place. Compound 1, Form B was not analyzed by NMR at 24 hours because of low material availability. The results are shown below in Table 14.

TABLE 14

| | | 30 minutes | | 120 minutes | | 24 hours | |
|---|---|---|---|---|---|---|---|
| Medium | Material | Solubility (mg/mL) | PH | Solubility (mg/mL) | PH | Solubility (mg/mL) | PH |
| FaSSIF | Compound 1 Form B | 0.045 | 6 | 0.034 | 6 | 0.018 | 6.2 |
| | Compound 3 Form B | 0.065 | 6 | 0.034 | 6 | 0.016 | 5.7 |
| | Compound 2 Form A | 0.078 | 6 | 0.040 | 6 | 0.014 | 5.0 |
| | Compound 4 Form A | 0.071 | 6 | 0.038 | 5.5 | 0.025 | 1.9 |
| | Compound A Form B | 0.0049 | 6 | 0.011 | 6 | 0.0095 | 6.4 |
| FeSSIF | Compound 1 Form B | 0.058 | 5 | 0.056 | 5 | 0.063 | 4.8 |
| | Compound 3 Form B | 0.027 | 5 | 0.043 | 5 | 0.16 | 4.4 |
| | Compound 2 Form A | 0.058 | 5 | 0.16 | 5 | 0.12 | 4.7 |
| | Compound 4 Form A | 0.048 | 5 | 0.11 | 4.5 | 0.033 | 4.4 |
| | Compound A Form B | <0.0001 | 5 | 0.027 | 5 | 0.021 | 4.8 |
| FaSSGF | Compound 1 Form B | <0.0001 | 1.5 | <0.0001 | 1.5 | <0.0001 | 1.2 |
| | Compound 3 Form B | <0.0001 | 1.5 | <0.0001 | 1.5 | <0.0001 | 1.2 |
| | Compound 2 Form A | <0.0001 | 1.5 | <0.0001 | 1.5 | <0.0001 | 1.2 |
| | Compound 4 Form A | <0.0001 | 1.5 | <0.0001 | 1.5 | <0.0001 | 1.1 |
| | Compound A Form B | <0.0001 | 1.5 | <0.0001 | 1.5 | <0.0001 | 1.1 |
| Water | Compound 1 Form B | <0.0001 | 4.5 | <0.0001 | 4.5 | <0.0001 | 3.4 |
| | Compound 3 Form B | <0.0001 | 4 | <0.0001 | 4 | <0.0001 | 2.4 |
| | Compound 2 Form A | <0.0001 | 3.5 | <0.0001 | 4 | <0.0001 | 2.9 |
| | Compound 4 Form A | <0.0001 | 4.5 | <0.0001 | 3 | <0.0001 | 1.5 |
| | Compound A Form B | <0.0001 | 4.5 | <0.0001 | 4.5 | <0.0001 | 7.7 |

As can be seen, Compound 2, Form A and Compound 3, Form B showed the highest solubility at 24 hours in FeSSIF.

Example 10—Stability Studies

Stability studies of compound A, Form B, Compound 1, Form B, Compound 2, Form A, Compound 3, Form B, and Compound 4, Form A was carried out at 40° C./75% RH. Samples were stored in loosely capped vials in a chamber containing a saturated NaCl solution to achieve approximately 75% RH within the chamber. The chamber was stored in a 40° C. oven. Samples were analyzed at Time 0, 1 week, 2 weeks, and 4 weeks using the HPLC parameters described above in Table 13. The results are shown below in Table 15.

TABLE 15

Stability Studies

| Material | Timepoint | % Area |
|---|---|---|
| Compound 1 | Time 0 | 99.90 |
| Form B | 1 Week | 99.59 |
|  | 2 Weeks | 99.53 |
|  | 4 Weeks | 99.46 |
| Compound 3 | Time 0 | 99.88 |
| Form B | 1 Week | 91.60 |
|  | 2 Weeks | 69.61 |
|  | 4 Weeks | 16.23 |
| Compound 2 | Time 0 | 99.87 |
| Form A | 1 Week | 99.20 |
|  | 2 Weeks | 98.30 |
|  | 4 Weeks | 98.58 |
| Compound 4 | Time 0 | 99.77 |
| Form A | 1 Week | 94.31 |
|  | 2 Weeks | 94.20 |
|  | 4 Weeks | 99.37 |
| Compound A | Time 0 | 99.62* |
| Form B | 1 Week | 99.22 |
|  | 2 Weeks | 99.05 |
|  | 4 Weeks | 99.58 |

*1 mg/mL

Overall, significant degradation was observed over time for Compound 3 Form B. The solids at the end of the study were confirmed to have lost all crystallinity and became x-ray amorphous. Compound A Form B and Compound 1 Form B appear equally stable at 40° C./75% RH. Compound 4 Form A exhibited degradation at 1 and 2 weeks, but the degradant peaks were no longer present at 4 weeks, which improved the percent area of the main peak. Compound 2 Form A is fairly stable at these accelerated conditions, losing only ~1.5% area over four weeks.

While we have described a number of embodiments of this invention, it is apparent that our basic examples may be altered to provide other embodiments that utilize the compounds and methods of this invention. Therefore, it will be appreciated that the scope of this invention is to be defined by the application and claims rather than by the specific embodiments that have been represented by way of example.

We claim:
1. A compound represented by formula 2:

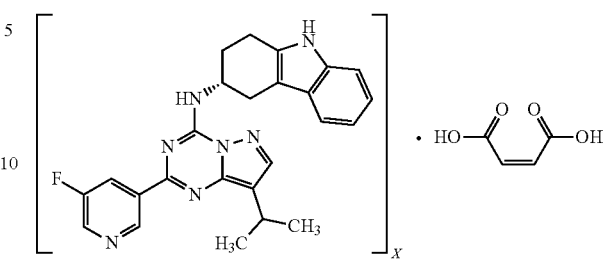

wherein 1≤X≤2.

2. A pharmaceutical composition comprising the compound according to claim 1 and a pharmaceutically acceptable carrier or excipient.

3. A method for inhibiting aryl hydrocarbon receptor (AHR) activity in a biological sample, wherein the method comprises contacting the biological sample with the compound according to claim 1.

4. A method for inhibiting aryl hydrocarbon receptor (AHR) activity in a patient in need thereof, wherein the method comprises administering to the patient a therapeutically effective amount of the compound according to claim 1.

5. The method according to claim 4, wherein the patient has an AHR-mediated disorder selected from the group consisting of a cancer and an inflammatory disorder.

6. The method according to claim 5, wherein the cancer is selected from the group consisting of acute myeloid leukemia, bladder cancer, esophageal cancer, head and neck squamous cell carcinoma, kidney cancer, leukemia, lung cancer, melanoma, ovarian cancer, and stomach cancer.

7. A process for preparing a compound represented by formula 2 according to claim 1:

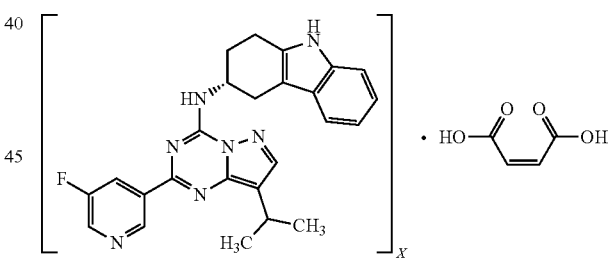

wherein 1≤X≤2;
wherein the process comprises the following step:
combining a compound represented by formula A:

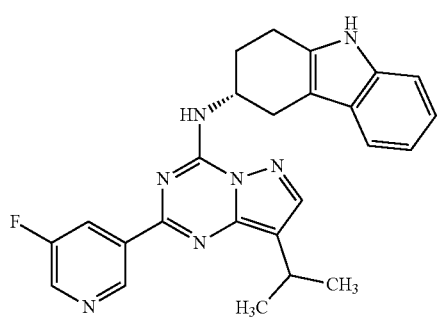

with maleic acid represented by the following formula:

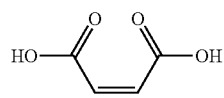

optionally in the presence of a solvent.

8. The process according to claim 7, wherein the process further comprises combining the compound represented by formula A and maleic acid in a stoichiometric ratio of 2:1.

9. A crystal form of a compound represented by formula 2:

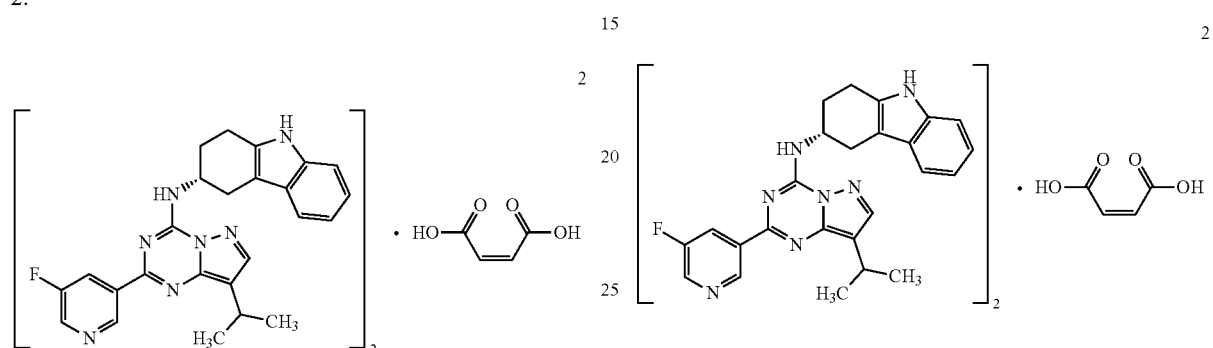

wherein the crystal form is crystal Form A; and
wherein crystal Form A is characterized by an X-ray powder diffraction pattern comprising at least one characteristic peak at an angle (°2θ) selected from the group consisting of 5.3°±0.2°2θ, 11.3°±0.2°2θ, and 16.0°±0.2°2θ.

10. The crystal form according to claim 9, wherein the crystal form is further characterized by an X-ray powder diffraction pattern comprising at least two characteristic peaks at angles (°2θ) selected from the group consisting of 5.3°±0.2°2θ, 11.3°±0.2°2θ, and 16.0°±0.2°2θ.

11. The crystal form according to claim 9, wherein the crystal form is further characterized by an X-ray powder diffraction pattern comprising three characteristic peaks at angles (°2θ) of 5.3°±0.2°2θ, 11.3°±0.2°2θ, and 16.0°±0.2°2θ.

12. The crystal form according to claim 9, wherein the crystal form is further characterized by an X-ray powder diffraction pattern as depicted in FIG. 8.

13. The crystal form according to claim 9, wherein the crystal form is further characterized by a thermogravimetry/differential thermal analysis trace as depicted in FIG. 9.

14. A pharmaceutical composition comprising the crystal form according to claim 9 and a pharmaceutically acceptable carrier or excipient.

15. A method for inhibiting aryl hydrocarbon receptor (AHR) activity in a biological sample, wherein the method comprises contacting the biological sample with the crystal form according to claim 9.

16. A method for inhibiting aryl hydrocarbon receptor (AHR) activity in a patient in need thereof, wherein the method comprises administering to the patient a therapeutically effective amount of the crystal form according to claim 9.

17. The method according to claim 16, wherein the patient has an AHR-mediated disorder selected from the group consisting of a cancer and an inflammatory disorder.

18. The method according to claim 17, wherein the cancer is selected from the group consisting of acute myeloid leukemia, bladder cancer, esophageal cancer, head and neck squamous cell carcinoma, kidney cancer, leukemia, lung cancer, melanoma, ovarian cancer, and stomach cancer.

19. A process for preparing the crystal form of a compound represented by formula 2 according to claim 9:

wherein the crystal form is crystal Form A; and
wherein crystal Form A is characterized by an X-ray powder diffraction pattern comprising at least one characteristic peak at an angle (°2θ) selected from the group consisting of 5.3°±0.2°2θ, 11.3°±0.2°2θ, and 16.0°±0.2°2θ;
wherein the process comprises the following step:
combining a compound represented by formula A:

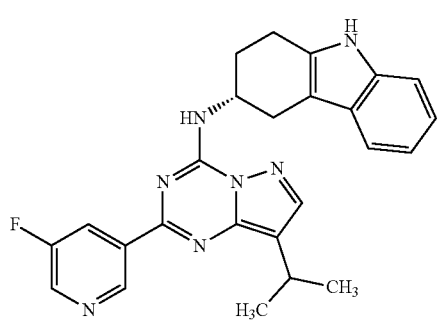

with maleic acid represented by the following formula:

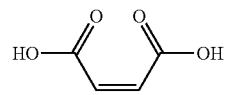

optionally in the presence of a solvent.

* * * * *